US008114964B2

(12) United States Patent
Das et al.

(10) Patent No.: US 8,114,964 B2
(45) Date of Patent: Feb. 14, 2012

(54) ANTI-MCP-1 ANTIBODIES, COMPOSITIONS, METHODS AND USES

(75) Inventors: Anuk Das, Radnor, PA (US); Raymond Sweet, Radnor, PA (US); Ping Tsui, Gaithersburg, MD (US); Michael Bardroff, Lörrach (DE)

(73) Assignee: Centocor, Inc., Malvern, PA (US)

( * ) Notice: Subject to any disclaimer, the term of this patent is extended or adjusted under 35 U.S.C. 154(b) by 366 days.

(21) Appl. No.: 11/942,126

(22) Filed: Nov. 19, 2007

(65) Prior Publication Data

US 2009/0068109 A1 Mar. 12, 2009

Related U.S. Application Data

(63) Continuation of application No. PCT/US2006/019627, filed on May 19, 2006.

(60) Provisional application No. 60/682,654, filed on May 19, 2005.

(51) Int. Cl.
| | |
|---|---|
| C07K 16/00 | (2006.01) |
| C12P 21/08 | (2006.01) |
| A61K 39/395 | (2006.01) |
| A61K 39/40 | (2006.01) |
| A61K 39/00 | (2006.01) |
| C07K 14/00 | (2006.01) |

(52) U.S. Cl. ............... 530/387.1; 530/387.3; 530/388.1; 530/388.23; 424/130.1; 424/133.1; 424/141.1; 424/145.1

(58) Field of Classification Search .................. None
See application file for complete search history.

(56) References Cited

U.S. PATENT DOCUMENTS

| 5,459,128 | A | 10/1995 | Rollins et al. |
| 6,168,791 | B1 | 1/2001 | Larsen et al. |
| 6,869,606 | B1 | 3/2005 | Newman et al. |
| 7,202,343 | B2 | 4/2007 | Gudas et al. |
| 7,342,106 | B2 | 3/2008 | Sugimura et al. |
| 7,405,277 | B2 | 7/2008 | De Fougerolles et al. |
| 7,468,253 | B2 | 12/2008 | Wei |
| 7,482,434 | B2 | 1/2009 | Gudas et al. |
| 2004/0047860 | A1 | 3/2004 | Hiestand et al. |
| 2006/0039913 | A1 | 2/2006 | Das et al. |
| 2006/0171943 | A1 | 8/2006 | Comeau et al. |

FOREIGN PATENT DOCUMENTS

| EP | 1538203 B1 | 1/2010 |
| JP | 05276986 | 10/1993 |
| JP | 9067399 | 3/1997 |
| WO | WO 95/09232 A2 | 4/1995 |
| WO | WO 01/05950 A2 | 1/2001 |
| WO | WO 01/89565 A1 | 11/2001 |
| WO | WO 02/02640 A | 1/2002 |
| WO | WO 03/048083 A1 | 6/2003 |
| WO | WO 2004/016769 A2 | 2/2004 |
| WO | WO 2004/050836 A2 | 6/2004 |
| WO | WO 2006/119942 A1 | 11/2006 |
| WO | WO 2006/125201 | * 11/2006 |

OTHER PUBLICATIONS

Pardridge. Current Opinion in Pharmacology. 2006, 6:494-500.*
Zlotnik, Yoshie 2000. Immunity 12:121-127.
Rauchenberger,R., Borges,E., Thomassen-Wolf,E., Rom,E., Adar,R., Yaniv,Y., Malka,M., Chumakov,I., Kotzer,S., Resnitzky,D., Knappik,A., Reiffert,S., Prassler,J., Jury,K., Waldherr,D., Bauer,S., Kretzschmar,T., Yayon,A., and Rothe,C. (2003). Human combinatorial Fab Library yielding specific and functional antibodies against the human fibroblast growth factor receptor 3. J Biol Chem. 278(40):38194-38205.
Haenel C, Satzger M, Della Ducata D, Ostendorp R and Brocks B (2005) Characterization of High Affinity Antibodies by Electrochemiluminescence-Based Equilibrium Titration (accepted for publication in Analytical Biochemistry), 339: pp. 182-184.
Hemmerich S, Paavola C, Bloom A, Bhakta S, Freedman R, Grunberger D, Krstenansky J, Lee S, McCarley D, Mulkins M, Wong B, Pease J, Mizoue L, Mirzadegan T, Polsky I, Thompson K, Handel TM, Jarnagin K. (1999). Identification of residues in the monocyte chemotactic protein-1 that contact the MCP-1 receptor, CCR2. Biochemistry 38(40):13013-25.
Knappik, A., Ge,L., Honegger,A., Pack,P., Fischer,M., Wellnhofer,G., Hoess,A., Wolle,J., Pluckthun,A., and Virnekas,B. (2000). Fully synthetic human combinatorial antibody libraries (HuCAL) based on modular consensus frameworks and CDRs randomized with trinucleotides. J Mol Biol 296, 57-86.
Leonard EJ, Yoshimura T. (1990). Human monocyte chemoattractant protein-1. Immunol Today., 11: 97-101.
Haringman et al., A Randomized Controlled Trianwith an Anti-CCL2 (Anti-Monocyte Chemotactic Protein 1) Monoclonal Antibody in Patients with Rheumatoid Arthritis, Arthritis & Rheumatism, vol. 54, No. 8 p. 387-2392 (2006).
Salcedo et al., Human endothelial cells express CCR2 and response to MCP-1; direct role of MCP-1 n angiogenesis and tumor progression, Blood, 1, (2000), vol. 96, No. 1, p. 34.
Furukawa et al., Anti-Monocyte Chemoattractant Protein-1/ Monocyte Chemotactic and Activating Factor Antibody Inhibits Neointimal Hyperplasic in Injured Rat Carotid Arteries, Circulation Research, (1998).
Jarnagin et al., Identification of Surface Residues of the Monocyte Chemotactic Protein 1 That Afect Signaling thorugh the Receptor CCR2, Biochemistry, (1999) vol. 38, pp. 16167-16177.
Lukacs et al., Differential Recruitment of Leukocyte Populations and Alternation of Airway Hyperreactivity by C-C Family Chemokinesin Allergic Airway Inflammation, J of Immunology, (1997) 158; p. 4398-4404.
Gordillo et al., A key angiogenic role of monocyte chemoattractant protein-1 in hemangioendotheliioma proliferation, Am J Physiol Cell Physiol 287; p. C866-C873 (2004).
Franciotta et al., Serum and CSF levels of MCP-1 and IP-10 in multiple sclerosis patents with acute and stable disease and undergoing immunomodulatory therapies, J of Neuroimmunology, 115 (2001) p. 192-198.

* cited by examiner

*Primary Examiner* — Chun Dahle
(74) *Attorney, Agent, or Firm* — Brian C. Carey

(57) ABSTRACT

The present invention relates to at least one novel anti-MCP-1 antibody, including isolated nucleic acids that encode at least one anti-MCP-1 antibody, MCP-1, vectors, host cells, transgenic animals or plants, and methods of making and using thereof, including therapeutic compositions, methods and devices.

5 Claims, No Drawings

SEQUENCE LISTING

```
<160> NUMBER OF SEQ ID NOS: 29

<210> SEQ ID NO 1
<211> LENGTH: 76
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa may be Gln, Glu, or pyroglutamic acid
<220> FEATURE:
<221> NAME/KEY: VARIANT
<222> LOCATION: (40)..(40)
<223> OTHER INFORMATION: Xaa may be Ala or Ser
<220> FEATURE:
<221> NAME/KEY: VARIANT
```

```
<222> LOCATION: (41)..(41)
<223> OTHER INFORMATION: Xaa may be Val or Ile
<220> FEATURE:
<221> NAME/KEY: VARIANT
<222> LOCATION: (43)..(43)
<223> OTHER INFORMATION: Xaa may be Phe or Tyr
<220> FEATURE:
<221> NAME/KEY: SITE
<222> LOCATION: (69)..(69)
<220> FEATURE:
<221> NAME/KEY: SITE
<222> LOCATION: (69)..(69)
<223> OTHER INFORMATION: Conjugation site, e.g. biotin or PEG-biotin
<220> FEATURE:
<221> NAME/KEY: SITE
<222> LOCATION: (75)..(75)
<223> OTHER INFORMATION: Conjugate position, e.g. biotin or PEG-biotin

<400> SEQUENCE: 1

Xaa Pro Asp Ala Ile Asn Ala Pro Val Thr Cys Cys Tyr Asn Phe Thr
 1               5                  10                  15

Asn Arg Lys Ile Ser Val Gln Arg Leu Ala Ser Tyr Arg Arg Ile Thr
            20                  25                  30

Ser Ser Lys Cys Pro Lys Glu Xaa Xaa Ile Xaa Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 2
<211> LENGTH: 119
<212> TYPE: PRT
<213> ORGANISM: Homo sapiens
<220> FEATURE:
<221> NAME/KEY: DOMAIN
<222> LOCATION: (1)..(25)
<223> OTHER INFORMATION: FR1
<220> FEATURE:
<221> NAME/KEY: SITE
<222> LOCATION: (26)..(35)
<223> OTHER INFORMATION: CDR1
<220> FEATURE:
<221> NAME/KEY: DOMAIN
<222> LOCATION: (36)..(46)
<223> OTHER INFORMATION: FR2
<220> FEATURE:
<221> NAME/KEY: SITE
<222> LOCATION: (47)..(66)
<223> OTHER INFORMATION: CDR2
<220> FEATURE:
<221> NAME/KEY: VARIANT
<222> LOCATION: (50)..(50)
<223> OTHER INFORMATION: Xaa is Gly or Ala
<220> FEATURE:
<221> NAME/KEY: VARIANT
<222> LOCATION: (52)..(52)
<223> OTHER INFORMATION: Xaa is Ile or Asn
<220> FEATURE:
<221> NAME/KEY: VARIANT
<222> LOCATION: (54)..(54)
<223> OTHER INFORMATION: Xaa is Ile or Leu
<220> FEATURE:
<221> NAME/KEY: VARIANT
<222> LOCATION: (55)..(55)
<223> OTHER INFORMATION: Xaa is Phe or Ala
<220> FEATURE:
<221> NAME/KEY: VARIANT
<222> LOCATION: (57)..(57)
<223> OTHER INFORMATION: Xaa is Thr or His
<220> FEATURE:
<221> NAME/KEY: VARIANT
<222> LOCATION: (58)..(58)
<223> OTHER INFORMATION: Xaa is Ala or Thr
```

```
<220> FEATURE:
<221> NAME/KEY: VARIANT
<222> LOCATION: (59)..(59)
<223> OTHER INFORMATION: Xaa is Asn or His
<220> FEATURE:
<221> NAME/KEY: DOMAIN
<222> LOCATION: (67)..(98)
<223> OTHER INFORMATION: FR3
<220> FEATURE:
<221> NAME/KEY: SITE
<222> LOCATION: (99)..(108)
<223> OTHER INFORMATION: CDR3
<220> FEATURE:
<221> NAME/KEY: DOMAIN
<222> LOCATION: (109)..(119)
<223> OTHER INFORMATION: FR4

<400> SEQUENCE: 2

Gln Val Glu Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Xaa Ile Xaa Pro Xaa Xaa Gly Xaa Xaa Xaa Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Gly Ile Tyr Gly Glu Leu Asp Phe Trp Gly Gln Gly
            100                 105                 110

Thr Leu Val Thr Val Ser Ser
        115

<210> SEQ ID NO 3
<211> LENGTH: 120
<212> TYPE: PRT
<213> ORGANISM: Homo sapiens
<220> FEATURE:
<221> NAME/KEY: DOMAIN
<222> LOCATION: (1)..(25)
<223> OTHER INFORMATION: FR1
<220> FEATURE:
<221> NAME/KEY: SITE
<222> LOCATION: (26)..(35)
<223> OTHER INFORMATION: CDR1
<220> FEATURE:
<221> NAME/KEY: DOMAIN
<222> LOCATION: (36)..(46)
<223> OTHER INFORMATION: FR2
<220> FEATURE:
<221> NAME/KEY: SITE
<222> LOCATION: (47)..(66)
<223> OTHER INFORMATION: CDR2
<220> FEATURE:
<221> NAME/KEY: DOMAIN
<222> LOCATION: (67)..(98)
<223> OTHER INFORMATION: FR3
<220> FEATURE:
<221> NAME/KEY: SITE
<222> LOCATION: (99)..(110)
<223> OTHER INFORMATION: CDR3
<220> FEATURE:
<221> NAME/KEY: DOMAIN
<222> LOCATION: (111)..(120)
<223> OTHER INFORMATION: FR4

<400> SEQUENCE: 3

Gln Val Gln Leu Val Glu Ser Gly Gly Gly Leu Val Gln Pro Gly Gly
```

```
                1               5                      10                     15
Ser Leu Arg Leu Ser Cys Ala Ala Ser Gly Phe Thr Phe Arg Ser Tyr
                        20                     25                     30

Gly Met Ser Trp Val Arg Gln Ala Pro Gly Lys Gly Leu Glu Trp Val
                        35                     40                     45

Ser Asn Ile Arg Ser Asp Gly Ser Tyr Thr Tyr Tyr Ala Asp Ser Val
        50                     55                     60

Lys Gly Arg Phe Thr Ile Ser Arg Asp Asn Ser Lys Asn Thr Leu Tyr
65                     70                     75                     80

Leu Gln Met Asn Ser Leu Arg Ala Glu Asp Thr Ala Val Tyr Tyr Cys
                        85                     90                     95

Ala Arg Phe Glu Phe Thr Pro Trp Thr Tyr Phe Asp Phe Trp Gly Gln
                        100                    105                    110

Gly Thr Leu Val Thr Val Ser Ser
                        115                    120

<210> SEQ ID NO 4
<211> LENGTH: 109
<212> TYPE: PRT
<213> ORGANISM: Homo sapiens
<220> FEATURE:
<221> NAME/KEY: DOMAIN
<222> LOCATION: (1)..(23)
<223> OTHER INFORMATION: FR1
<220> FEATURE:
<221> NAME/KEY: SITE
<222> LOCATION: (24)..(35)
<223> OTHER INFORMATION: CDR1
<220> FEATURE:
<221> NAME/KEY: DOMAIN
<222> LOCATION: (36)..(46)
<223> OTHER INFORMATION: FR2
<220> FEATURE:
<221> NAME/KEY: SITE
<222> LOCATION: (47)..(57)
<223> OTHER INFORMATION: CDR2
<220> FEATURE:
<221> NAME/KEY: DOMAIN
<222> LOCATION: (58)..(89)
<223> OTHER INFORMATION: FR3
<220> FEATURE:
<221> NAME/KEY: VARIANT
<222> LOCATION: (90)..(90)
<223> OTHER INFORMATION: X may be H or Q
<220> FEATURE:
<221> NAME/KEY: SITE
<222> LOCATION: (90)..(97)
<223> OTHER INFORMATION: CDR3
<220> FEATURE:
<221> NAME/KEY: VARIANT
<222> LOCATION: (94)..(94)
<223> OTHER INFORMATION: X may be Glu, Gln, Asp, Ser, Thr, or Phe
<220> FEATURE:
<221> NAME/KEY: VARIANT
<222> LOCATION: (95)..(95)
<223> OTHER INFORMATION: X may be Leu, Ile, His, Tyr, Phe, or Gln
<220> FEATURE:
<221> NAME/KEY: VARIANT
<222> LOCATION: (96)..(96)
<223> OTHER INFORMATION: X may be Trp, His, Ser, Proline
<220> FEATURE:
<221> NAME/KEY: VARIANT
<222> LOCATION: (97)..(97)
<223> OTHER INFORMATION: X may be Ala, Val, Asn, Gln, Ser, or Proline
<220> FEATURE:
<221> NAME/KEY: VARIANT
<222> LOCATION: (98)..(98)
<223> OTHER INFORMATION: X may be absent or Phe or Met
<220> FEATURE:
<221> NAME/KEY: DOMAIN
<222> LOCATION: (99)..(109)
<223> OTHER INFORMATION: FR4
```

-continued

<400> SEQUENCE: 4

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asp Ala
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Xaa Gln Tyr Ile Xaa Xaa Xaa
                85                  90                  95

Xaa Xaa Thr Phe Gly Gln Gly Thr Lys Val Glu Ile Lys
            100                 105

<210> SEQ ID NO 5
<211> LENGTH: 107
<212> TYPE: PRT
<213> ORGANISM: Homo sapiens
<220> FEATURE:
<221> NAME/KEY: DOMAIN
<222> LOCATION: (1)..(22)
<223> OTHER INFORMATION: FR1
<220> FEATURE:
<221> NAME/KEY: SITE
<222> LOCATION: (23)..(33)
<223> OTHER INFORMATION: CDR1
<220> FEATURE:
<221> NAME/KEY: DOMAIN
<222> LOCATION: (34)..(44)
<223> OTHER INFORMATION: FR2
<220> FEATURE:
<221> NAME/KEY: SITE
<222> LOCATION: (45)..(55)
<223> OTHER INFORMATION: CDR2
<220> FEATURE:
<221> NAME/KEY: DOMAIN
<222> LOCATION: (56)..(87)
<223> OTHER INFORMATION: FR3
<220> FEATURE:
<221> NAME/KEY: SITE
<222> LOCATION: (88)..(97)
<223> OTHER INFORMATION: CDR3
<220> FEATURE:
<221> NAME/KEY: VARIANT
<222> LOCATION: (89)..(89)
<223> OTHER INFORMATION: Xaa may be Ser or Thr
<220> FEATURE:
<221> NAME/KEY: VARIANT
<222> LOCATION: (91)..(91)
<223> OTHER INFORMATION: Xaa may be Asp or Thr
<220> FEATURE:
<221> NAME/KEY: VARIANT
<222> LOCATION: (92)..(92)
<223> OTHER INFORMATION: Xaa may be Arg or Ala
<220> FEATURE:
<221> NAME/KEY: VARIANT
<222> LOCATION: (93)..(93)
<223> OTHER INFORMATION: Xaa may be Gln or Phe
<220> FEATURE:
<221> NAME/KEY: VARIANT
<222> LOCATION: (96)..(96)
<223> OTHER INFORMATION: Xaa may be Thr or Ala
<220> FEATURE:
<221> NAME/KEY: VARIANT
<222> LOCATION: (97)..(97)
<223> OTHER INFORMATION: Xaa may be Ala, Gly, or Ser
<220> FEATURE:
<221> NAME/KEY: DOMAIN
<222> LOCATION: (98)..(107)

<223> OTHER INFORMATION: FR4

<400> SEQUENCE: 5

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Lys Lys Tyr Val
            20                  25                  30

Tyr Trp Tyr Gln Gln Lys Pro Gly Gln Ala Pro Val Leu Val Ile Tyr
        35                  40                  45

Asp Asp Asp Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Xaa Tyr Xaa Xaa Xaa Ser Ser Xaa
                85                  90                  95

Xaa Phe Gly Gly Gly Thr Lys Leu Thr Val Leu
            100                 105

<210> SEQ ID NO 6
<211> LENGTH: 10
<212> TYPE: PRT
<213> ORGANISM: Homo sapiens

<400> SEQUENCE: 6

Gly Gly Thr Phe Ser Ser Tyr Gly Ile Ser
1               5                   10

<210> SEQ ID NO 7
<211> LENGTH: 20
<212> TYPE: PRT
<213> ORGANISM: Homo sapiens

<400> SEQUENCE: 7

Trp Met Gly Gly Ile Ile Pro Ile Phe Gly Thr Ala Asn Tyr Ala Gln
1               5                   10                  15

Lys Phe Gln Gly
            20

<210> SEQ ID NO 8
<211> LENGTH: 20
<212> TYPE: PRT
<213> ORGANISM: Homo sapiens

<400> SEQUENCE: 8

Trp Met Gly Ala Ile Asn Pro Leu Ala Gly His Thr His Tyr Ala Gln
1               5                   10                  15

Lys Phe Gln Gly
            20

<210> SEQ ID NO 9
<211> LENGTH: 10
<212> TYPE: PRT
<213> ORGANISM: Homo sapiens

<400> SEQUENCE: 9

Tyr Asp Gly Ile Tyr Gly Glu Leu Asp Phe
1               5                   10

<210> SEQ ID NO 10
<211> LENGTH: 10
<212> TYPE: PRT
<213> ORGANISM: Homo sapiens

```
<400> SEQUENCE: 10

Gly Phe Thr Phe Arg Ser Tyr Gly Met Ser
1               5                   10

<210> SEQ ID NO 11
<211> LENGTH: 20
<212> TYPE: PRT
<213> ORGANISM: Homo sapiens

<400> SEQUENCE: 11

Trp Val Ser Asn Ile Arg Ser Asp Gly Ser Tyr Thr Tyr Tyr Ala Asp
1               5                   10                  15

Ser Val Lys Gly
            20

<210> SEQ ID NO 12
<211> LENGTH: 11
<212> TYPE: PRT
<213> ORGANISM: Homo sapiens

<400> SEQUENCE: 12

Phe Glu Phe Thr Pro Trp Thr Tyr Phe Asp Phe
1               5                   10

<210> SEQ ID NO 13
<211> LENGTH: 12
<212> TYPE: PRT
<213> ORGANISM: Homo sapiens

<400> SEQUENCE: 13

Arg Ala Ser Gln Ser Val Ser Asp Ala Tyr Leu Ala
1               5                   10

<210> SEQ ID NO 14
<211> LENGTH: 11
<212> TYPE: PRT
<213> ORGANISM: Homo sapiens

<400> SEQUENCE: 14

Leu Leu Ile Tyr Asp Ala Ser Ser Arg Ala Thr
1               5                   10

<210> SEQ ID NO 15
<211> LENGTH: 9
<212> TYPE: PRT
<213> ORGANISM: Homo sapiens

<400> SEQUENCE: 15

His Gln Tyr Ile Glu Leu Trp Ser Phe
1               5

<210> SEQ ID NO 16
<211> LENGTH: 9
<212> TYPE: PRT
<213> ORGANISM: Homo sapiens

<400> SEQUENCE: 16

His Gln Tyr Ile Gln Leu His Ser Phe
1               5

<210> SEQ ID NO 17
<211> LENGTH: 8
<212> TYPE: PRT
<213> ORGANISM: Homo sapiens
```

<400> SEQUENCE: 17

His Gln Tyr Ile Phe Tyr Pro Asn
1               5

<210> SEQ ID NO 18
<211> LENGTH: 11
<212> TYPE: PRT
<213> ORGANISM: Homo sapiens

<400> SEQUENCE: 18

Ser Gly Asp Asn Leu Gly Lys Lys Tyr Val Tyr
1               5                   10

<210> SEQ ID NO 19
<211> LENGTH: 11
<212> TYPE: PRT
<213> ORGANISM: Homo sapiens

<400> SEQUENCE: 19

Leu Val Ile Tyr Asp Asp Asn Arg Pro Ser
1               5                   10

<210> SEQ ID NO 20
<211> LENGTH: 10
<212> TYPE: PRT
<213> ORGANISM: Homo sapiens

<400> SEQUENCE: 20

Gln Thr Tyr Asp Arg Phe Ser Ser Thr Ala
1               5                   10

<210> SEQ ID NO 21
<211> LENGTH: 10
<212> TYPE: PRT
<213> ORGANISM: Homo sapiens

<400> SEQUENCE: 21

Gln Ser Tyr Asp Arg Phe Ser Ser Thr Gly
1               5                   10

<210> SEQ ID NO 22
<211> LENGTH: 20
<212> TYPE: PRT
<213> ORGANISM: Homo sapiens
<220> FEATURE:
<221> NAME/KEY: VARIANT
<222> LOCATION: (4)..(4)
<223> OTHER INFORMATION: Xaa may be Gly or Ala
<220> FEATURE:
<221> NAME/KEY: VARIANT
<222> LOCATION: (6)..(6)
<223> OTHER INFORMATION: Xaa may be Ile or Asn
<220> FEATURE:
<221> NAME/KEY: VARIANT
<222> LOCATION: (8)..(8)
<223> OTHER INFORMATION: Xaa may be Ile or Leu
<220> FEATURE:
<221> NAME/KEY: VARIANT
<222> LOCATION: (9)..(9)
<223> OTHER INFORMATION: Xaa may be Phe or Ala
<220> FEATURE:
<221> NAME/KEY: VARIANT
<222> LOCATION: (11)..(11)
<223> OTHER INFORMATION: Xaa may be Thr or His
<220> FEATURE:
<221> NAME/KEY: VARIANT
<222> LOCATION: (12)..(12)
<223> OTHER INFORMATION: Xaa may be Ala or Thr
<220> FEATURE:

```
<221> NAME/KEY: VARIANT
<222> LOCATION: (13)..(13)
<223> OTHER INFORMATION: Xaa may be Asn or His

<400> SEQUENCE: 22

Trp Met Gly Xaa Ile Xaa Pro Xaa Xaa Gly Xaa Xaa Xaa Tyr Ala Gln
1               5                   10                  15

Lys Phe Gln Gly
            20

<210> SEQ ID NO 23
<211> LENGTH: 22
<212> TYPE: PRT
<213> ORGANISM: Homo sapiens
<220> FEATURE:
<221> NAME/KEY: VARIANT
<222> LOCATION: (10)..(10)
<223> OTHER INFORMATION: Xaa may be Ser or Thr
<220> FEATURE:
<221> NAME/KEY: VARIANT
<222> LOCATION: (11)..(11)
<223> OTHER INFORMATION: Xaa may be Gly or Asn
<220> FEATURE:
<221> NAME/KEY: VARIANT
<222> LOCATION: (13)..(13)
<223> OTHER INFORMATION: Xaa may be Ala or Thr
<220> FEATURE:
<221> NAME/KEY: VARIANT
<222> LOCATION: (15)..(15)
<223> OTHER INFORMATION: Xaa may be Gly, Ser, or Thr
<220> FEATURE:
<221> NAME/KEY: VARIANT
<222> LOCATION: (19)..(19)
<223> OTHER INFORMATION: Xaa may be Ser or Gly

<400> SEQUENCE: 23

Trp Val Ser Ser Ile Glu His Lys Trp Xaa Xaa Tyr Xaa Thr Xaa Tyr
1               5                   10                  15

Ala Ala Xaa Val Lys Gly
            20

<210> SEQ ID NO 24
<211> LENGTH: 8
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa may be His or Gln
<220> FEATURE:
<221> NAME/KEY: VARIANT
<222> LOCATION: (5)..(5)
<223> OTHER INFORMATION: Xaa may be Ser or Phe
<220> FEATURE:
<221> NAME/KEY: VARIANT
<222> LOCATION: (6)..(6)
<223> OTHER INFORMATION: Xaa may be Gln, His, Phe, or Tyr
<220> FEATURE:
<221> NAME/KEY: VARIANT
<222> LOCATION: (8)..(8)
<223> OTHER INFORMATION: Xaa may be  Ala, Asn, Gln, or Val

<400> SEQUENCE: 24

Xaa Gln Tyr Ile Xaa Xaa Pro Xaa
1               5

<210> SEQ ID NO 25
<211> LENGTH: 10
<212> TYPE: PRT
<213> ORGANISM: Homo sapiens
<220> FEATURE:
<221> NAME/KEY: VARIANT
```

-continued

```
<222> LOCATION: (2)..(2)
<223> OTHER INFORMATION: Xaa may be Ser or Thr
<220> FEATURE:
<221> NAME/KEY: VARIANT
<222> LOCATION: (4)..(4)
<223> OTHER INFORMATION: Xaa may be Asp or Thr
<220> FEATURE:
<221> NAME/KEY: VARIANT
<222> LOCATION: (5)..(5)
<223> OTHER INFORMATION: Xaa may be Ala or Arg
<220> FEATURE:
<221> NAME/KEY: VARIANT
<222> LOCATION: (6)..(6)
<223> OTHER INFORMATION: Xaa may be Gln or Phe
<220> FEATURE:
<221> NAME/KEY: VARIANT
<222> LOCATION: (9)..(9)
<223> OTHER INFORMATION: Xaa may be Ala or Thr
<220> FEATURE:
<221> NAME/KEY: VARIANT
<222> LOCATION: (10)..(10)
<223> OTHER INFORMATION: Xaa may be Ala, Gly, or Ser

<400> SEQUENCE: 25

Gln Xaa Tyr Xaa Xaa Xaa Ser Ser Xaa Xaa
1               5                  10

<210> SEQ ID NO 26
<211> LENGTH: 10
<212> TYPE: PRT
<213> ORGANISM: Homo sapiens
<220> FEATURE:
<221> NAME/KEY: VARIANT
<222> LOCATION: (2)..(2)
<223> OTHER INFORMATION: Xaa may be Gly or Phe
<220> FEATURE:
<221> NAME/KEY: VARIANT
<222> LOCATION: (5)..(5)
<223> OTHER INFORMATION: Xaa may be Ser or Arg
<220> FEATURE:
<221> NAME/KEY: VARIANT
<222> LOCATION: (9)..(9)
<223> OTHER INFORMATION: Xaa may be Ile or Met

<400> SEQUENCE: 26

Gly Xaa Thr Phe Xaa Ser Tyr Gly Xaa Ser
1               5                  10

<210> SEQ ID NO 27
<211> LENGTH: 119
<212> TYPE: PRT
<213> ORGANISM: Homo sapiens
<220> FEATURE:
<221> NAME/KEY: DOMAIN
<222> LOCATION: (1)..(25)
<223> OTHER INFORMATION: FR1
<220> FEATURE:
<221> NAME/KEY: SITE
<222> LOCATION: (26)..(35)
<223> OTHER INFORMATION: CDR1
<220> FEATURE:
<221> NAME/KEY: DOMAIN
<222> LOCATION: (36)..(46)
<223> OTHER INFORMATION: FR2
<220> FEATURE:
<221> NAME/KEY: SITE
<222> LOCATION: (47)..(66)
<223> OTHER INFORMATION: CDR2
<220> FEATURE:
<221> NAME/KEY: DOMAIN
<222> LOCATION: (67)..(98)
<223> OTHER INFORMATION: FR3
<220> FEATURE:
<221> NAME/KEY: SITE
<222> LOCATION: (99)..(108)
<223> OTHER INFORMATION: CDR3
```

```
<220> FEATURE:
<221> NAME/KEY: DOMAIN
<222> LOCATION: (109)..(119)
<223> OTHER INFORMATION: FR4

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Gly Ile Tyr Gly Glu Leu Asp Phe Trp Gly Gln Gly
            100                 105                 110

Thr Leu Val Thr Val Ser Ser
        115

<210> SEQ ID NO 28
<211> LENGTH: 109
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa may be Asp or Glu
<220> FEATURE:
<221> NAME/KEY: DOMAIN
<222> LOCATION: (1)..(23)
<223> OTHER INFORMATION: FR 1
<220> FEATURE:
<221> NAME/KEY: SITE
<222> LOCATION: (24)..(35)
<220> FEATURE:
<221> NAME/KEY: DOMAIN
<222> LOCATION: (36)..(46)
<223> OTHER INFORMATION: FR2
<220> FEATURE:
<221> NAME/KEY: SITE
<222> LOCATION: (47)..(57)
<223> OTHER INFORMATION: CDR2
<220> FEATURE:
<221> NAME/KEY: DOMAIN
<222> LOCATION: (58)..(89)
<223> OTHER INFORMATION: FR3
<220> FEATURE:
<221> NAME/KEY: SITE
<222> LOCATION: (90)..(98)
<223> OTHER INFORMATION: CDR3
<220> FEATURE:
<221> NAME/KEY: DOMAIN
<222> LOCATION: (99)..(109)
<223> OTHER INFORMATION: FR4

<400> SEQUENCE: 28

Xaa Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asp Ala
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Val Pro Ala Arg Phe Ser
```

-continued

```
                 50                  55                  60
Gly Ser Gly Ser Gly Thr Asp Phe Thr Leu Thr Ile Ser Ser Leu Glu
 65                  70                  75                  80

Pro Glu Asp Phe Ala Val Tyr Tyr Cys His Gln Tyr Ile Gln Leu His
                 85                  90                  95

Ser Phe Thr Phe Gly Gln Gly Thr Lys Val Glu Ile Lys
            100                 105

<210> SEQ ID NO 29
<211> LENGTH: 9
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa may be His or Gln
<220> FEATURE:
<221> NAME/KEY: VARIANT
<222> LOCATION: (5)..(5)
<223> OTHER INFORMATION: Xaa may be Asp, Glu, Gln, or Thr
<220> FEATURE:
<221> NAME/KEY: VARIANT
<222> LOCATION: (6)..(6)
<223> OTHER INFORMATION: Xaa may be Ile, Leu, or Tyr
<220> FEATURE:
<221> NAME/KEY: VARIANT
<222> LOCATION: (7)..(7)
<223> OTHER INFORMATION: Xaa may be Ser, Pro, His, or Tryp
<220> FEATURE:
<221> NAME/KEY: VARIANT
<222> LOCATION: (8)..(8)
<223> OTHER INFORMATION: Xaa may be Ser or Pro
<220> FEATURE:
<221> NAME/KEY: VARIANT
<222> LOCATION: (9)..(9)
<223> OTHER INFORMATION: Xaa may be Met or Phe

<400> SEQUENCE: 29

Xaa Gln Tyr Ile Xaa Xaa Xaa Xaa Xaa
 1               5
```

ANTI-MCP-1 ANTIBODIES, COMPOSITIONS, METHODS AND USES

CROSS REFERENCE TO RELATED APPLICATION

The present application is a continuation of and claims priority to PCT US/06/19627, filed May 19, 2006, which claims priority to U.S. provisional patent application Ser. No. 60/682,654, filed May 19, 2005. The contents of each application are incorporated herein by reference.

BACKGROUND OF THE INVENTION

1. Field of the Invention

The present invention relates to antibodies, including specified portions or variants, specific for at least one human monocyte chemoattractant protein-1 (MCP-1) protein or fragment thereof, as well as anti-idiotype antibodies, and nucleic acids encoding such anti-MCP-1 antibodies, complementary nucleic acids, vectors, host cells, and methods of making and using thereof, including therapeutic formulations, administration and devices.

2. Related Art

The Human Monocyte Chemoattractant Protein-1 (MCP-1) (also called CCL-2), a 8.6 kDa protein containing 76 amino acid residues, is a member of the chemokine-beta (or C—C) family of cytokines. Chemokines are low molecular weight (8-10 kDa), inducible, secreted, pro-inflammatory, chemotactic cytokines that have been shown to play a central role in the peri-vascular transmigration and accumulation of specific subsets of leukocytes at sites of tissue damage. Two major families have been defined depending on the positioning of four conserved cysteines. The CXC or α-chemokines predominantly attract neutrophils, whereas the CC or β-chemokines predominantly attract monocytes and other leukocytes but not neutrophils (Leonard and Yoshimura et al., 1990). Members of the Monocyte Chemotactic Protein-1 (MCP-1) family form a major component of the C—C family of chemokines and are considered the principal chemokines involved in the recruitment of monocytes, macrophages, and activated lymphocytes. Looking at the homology of MCP-1 from different species, the human and the monkey MCP-1 differ in 2 amino acids only, revealing a sequence identity of 97%, while murine MCP-1, a 13.8 kDa protein containing 125 amino acid residues, differs from human MCP-1 in molecular size and extent of glycosylation.

Chemokine receptors belong to the large family of G protein-coupled, seven transmembrane (7 TM) domain receptors (GPCRs, also called serpentine receptors). Based on the receptor nomenclature established at the 1996 Gordon Research Conference on chemotactic cytokines, the chemokine receptors that bind CXC chemokines are designated CXCRs and the receptors that bind CC chemokines are designated CCRs.

MCP-1 is known to bind and signal through the chemokine receptor CCR2. CCR2 is a seven trans-membrane-spanning G-protein-coupled receptor expressed on many cells including monocytes, T-cells, B-cells, and basophils. Two MCP-1 specific receptors, CCR2A and CCR2B, have been cloned which signal in response to nanomolar (nM) concentrations of MCP-1. CCR2A (CC-CKR2A) and CCR2B (CC-CKR2A) represent two cDNAs that encode two MCP-1-specific receptors with alternatively spliced carboxyl tails. MCP-1 binds to both isoforms with high affinity MCP-1 induces calcium flux in cells expressing CCR2B but not in cells expressing CCR2A. 5-fold less MCP-1 induces chemotaxis in cells expressing CCR2B compared to cells expressing CCR2A.

Other proteins with certain functional and sequence homology to human MCP-1 are known. Especially similar to MCP-1 (GenBank NP_002973) are MCP-2 (GenBank NP_005614) and eotaxin (GenBank P_51671); MCP-2 having 61.8 percent and eotaxin-1 having 63.2 percent sequence identity to MCP-1. The range of activities and spectrum of involvement of these proteins in human homeostatic mechanisms and pathology is not as well understood for the homologs of MCP-1. For example, MCP-2 (renamed CCL8) is related closely to MCP-1 and MCP-3 (renamed CCL7, Genbank NP_006264) and uses both CCR1 as well as CCR2B as its functional receptors. MCP-3 binds to a receptor designated D6. MCP-3 also binds to CCR10 and CCR1. The MCP-3 protein (97 amino acids) sequence shows 74 percent identity with MCP-1 and 58 percent homology with MCP-2. Secreted MCP-3 differs from MCP-1 in being N-glycosylated. MCP-4 (renamed CCL13, Genbank NP_005399) shares 56-61 percent sequence identity with the three known monocyte chemotactic proteins and is 60 percent identical with Eotaxin-1. The functions of MCP-4 appear to be highly similar to those of MCP-3 and Eotaxin. Like MCP-3, MCP-4 is a potent chemoattractant for monocytes and T-lymphocytes. It is inactive on neutrophils. On monocytes, MCP-4 binds to receptors that recognize MCP-1, MCP-3, RANTES (CCL5), and eotaxin (the CCR1 and CCR3 receptors) and shows full cross-desensitization with eotaxin-1. MCP-5 is murine CC-chemokine and related most closely to human MCP-1 (66% amino acid identity). The gene symbol for MCP-5 is SCYA12 (renamed CCL12). Cells transfected with the chemokine receptor CCR2 have been shown to respond to MCP-5. For general information on cytokines and chemokines see www._copewithcytokines.de/cope.cgi and for the current classification system, Zlotnik A., Yoshie O. 2000. Chemokines: a new classification system and their role in immunity. Immunity 12: 121-127.

125I-MCP-1 binds to monocytes and Scatchard plot analysis indicated that monocytes had a minimum of ~1700 binding sites per cell with a Kd of ~2 nM (Yoshimura and Leonard, 1990). Later equilibrium binding experiments with human monocytes reveal the presence of approximately 3000 binding sites per cell with a Kd of 0.77 nM (Ernst et al., 1994). 125I-MCP-1 also demonstrated high-affinity binding to dEoL-3 cells expressing CCR2 receptor with a Kd value of 0.4 nM (Sarau et al., 1997) confirming the sub-nanomolar affinity of MCP-1 to its receptor. To identify the regions of MCP-1 that contact its receptor, CCR2, all surface-exposed residues were substituted with alanine. Some residues were also mutated to other amino acids to identify the importance of charge, hydrophobicity, or aromaticity at specific positions. Two clusters of primarily basic residues (R24, K35, K38, K49, and Y13), separated by a 35 A hydrophobic groove, reduced the level of binding by 15-100-fold. Data suggest a model in which a large surface area of MCP-1 contacts the receptor, and the accumulation of a number of weak interactions results in the 35 pM affinity observed for the wild-type (WT) protein (Hemmerich et al., 1999). The range of affinities from 2 nM down to 35 pM in the literature might be due to the assays used and the respective assay limitations.

Other proteins with certain functional and sequence homology to human MCP-1 are known. Especially similar to MCP-1 (GenBank NP_002973) are MCP-2 (GenBank NP_005614) and eotaxin (GenBank P_51671); MCP-2 having 61.8 percent and eotaxin-1 having 63.2 percent sequence identity to MCP-1. The range of activities and spectrum of involvement of these proteins in human homeostatic mechanisms and pathology is not as well understood for the homologs of MCP-1. For example, MCP-2 is related closely to MCP-1 and MCP-3 (Genbank NP_006264) and uses both CCR1 as well as CCR2B as its functional receptors. MCP-3 binds to a receptor designated D6. MCP-3 also binds to CCR10. The MCP-3 protein (97 amino acids) sequence shows 74 percent identity with MCP-1 and 58 percent homology with MCP-2. Secreted MCP-3 differs from MCP-1 in being N-glycosylated. MCP-4 (Genbank NP_005399) shares 56-61 percent sequence identity with the three known monocyte chemotactic proteins and is 60 percent identical with Eotaxin-1. The functions of MCP-4 appear to be highly similar to those of MCP-3 and Eotaxin. Like MCP-3, MCP-4 is a potent chemoattractant for monocytes and T-lymphocytes. It is inactive on neutrophils. On monocytes MCP-4 binds to receptors that recognize MCP-1, MCP-3, and RANTES (CCR2). On eosinophils MCP-4 has similar efficacy and potency as MCP-3, RANTES, and Eotaxin. MCP-4 shares receptors with eotaxin (CCR1 and CCR3) and shows full cross-desensitization with eotaxin-1.

Other antibodies capable of binding MCP-1 have been reported: JP9067399 discloses an antibody obtained from isolated blood cells and JP05276986 discloses a hybridoma secreting an IgM anti-human MCP-1. More recently, antibodies capable of binding a plurality of beta-chemokines including MCP-1 were disclosed (WO03048083) and an MCP-1 binding antibody which also binds eotaxin (US20040047860).

Accordingly, there is a need to provide human antibodies specific for human MCP-1 for use in therapy to diminish or eliminate symptoms of MCP-1-dependent diseases, as well as improvements over known antibodies or fragments thereof.

SUMMARY OF THE INVENTION

The present invention provides isolated human, primate, rodent, mammalian, chimeric, humanized and/or CDR-grafted anti-MCP-1 antibodies and other immunoglobulin derived proteins, fragments, cleavage products and other specified portions and variants thereof, as well as anti-MCP-1 antibody compositions, encoding or complementary nucleic acids, vectors, host cells, compositions, formulations, devices, transgenic animals, transgenic plants, and methods of making and using thereof, as described and enabled herein, in combination with what is known in the art. In addition to the composition of the antibodies of the invention as described herein, the antibody of the present invention is defined by its affinity for human MCP-1, specificity for human MCP-1 and ability to block bioactivity of human MCP-1.

The present invention also provides at least one isolated anti-MCP-1 antibody, such as, but not limited to at least one an antibody, antibody fusion protein or fragment, as described herein. An antibody according to the present invention includes any protein or peptide containing molecule that comprises at least a portion of an immunoglobulin molecule, such as but not limited to, at least one ligand binding domain, such as but not limited to, a heavy chain or light chain variable region, a complementarity determining region (CDR) of a heavy or light chain or a ligand binding portion thereof as provided in Table 4A, B, D and E (SEQ ID NO: 6-26; and, optionally functionally associated with a framework region (e.g., FR1, FR2, FR3, FR4 or fragment thereof as described in Table 4C (SEQ ID NO: 2-5), further optionally comprising at least CH1, hinge, CH2, or CH3 of an human immunoglobulin. The at least one antibody amino acid sequence can further optionally comprise at least one specified substitution, insertion or deletion as described herein or as known in the art.

In an embodiment, the ligand binding portions of the antibody comprise SEQ ID NO: 27 and 28. In one aspect, the present invention provides at least one isolated mammalian anti-MCP-1 antibody, comprising at least one variable region comprising SEQ ID NO: 27 or 28.

In another aspect, the present invention provides at least one isolated mammalian anti-MCP-1 antibody, comprising either (i) all of the heavy chain complementarity determining regions (CDR) amino acid sequences of ID NOS: 6, 7 and 9; or (ii) all of the light chain CDR amino acids sequences of SEQ ID NOS: 13, 14, and 16.

The present invention provides, in one aspect, isolated nucleic acid molecules comprising, complementary, or hybridizing to, a polynucleotide encoding specific anti-MCP-1 antibodies, comprising at least one specified sequence, domain, portion or variant thereof. The present invention further provides recombinant vectors comprising said anti-MCP-1 antibody nucleic acid molecules, host cells containing such nucleic acids and/or recombinant vectors, as well as methods of making and/or using such antibody nucleic acids, vectors and/or host cells.

At least one antibody of the invention binds at least one specified epitope specific to at least one MCP-1 protein or variant or derivative such as those provided in SEQ ID NO: 1. The at least one epitope can comprise at least one antibody binding region that comprises at least one portion of said protein, which epitope is preferably comprised of at least 1-5 amino acids of at least one portion thereof, such as but not limited to, at least one functional, extracellular, soluble, hydrophillic, external or cytoplasmic domain of said protein, or any portion thereof.

The at least one antibody can optionally comprise at least one specified portion of at least one complementarity determining region (CDR) (e.g., CDR1, CDR2 or CDR3 of the heavy or light chain variable region provide as SEQ ID Nos: 27 and 28, respectively) provided as SEQ ID NOS: 6, 7, 9, 13, 14, and 16; and optionally further comprising at least one constant or variable framework region or any portion thereof, wherein the antibody blocks, inhibits or prevents at least one activity, such as, but not limited to MCP-1 binding to receptor on cell surfaces, CCR2 receptor internalization, MCP-1 stimulated Ca2+ mobilization or any other suitable known MCP-1 assay. An anti-MCP-1 antibody can thus be screened for a corresponding activity according to known methods, such as but not limited to, at least one biological activity towards a MCP-1 protein.

The present invention further provides at least one MCP-1 anti-idiotype antibody to at least one MCP-1 antibody of the present invention. The anti-idiotype antibody includes any protein or peptide containing molecule that comprises at least a portion of an immunoglobulin molecule, such as but not limited to at least one ligand binding portion (LBP), such as but not limited to a complementarity determining region (CDR) of a heavy or light chain, or a ligand binding portion thereof, a heavy chain or light chain variable region, a heavy chain or light chain constant region, a framework region, or any portion thereof, that can be incorporated into the anti-idiotype antibody of the present invention. An anti-idiotype antibody of the invention can include or be derived from any mammal, such as but not limited to a human, a mouse, a rabbit, a rat, a rodent, a primate, and the like.

The present invention provides, in one aspect, isolated nucleic acid molecules comprising, complementary, or hybridizing to, a polynucleotide encoding at least one MCP-1 anti-idiotype antibody, comprising at least one specified sequence, domain, portion or variant thereof. The present invention further provides recombinant vectors comprising said MCP-1 anti-idiotype antibody encoding nucleic acid molecules, host cells containing such nucleic acids and/or recombinant vectors, as well as methods of making and/or using such anti-idiotype antibody nucleic acids, vectors and/or host cells.

The present invention also provides at least one method for expressing at least one anti-MCP-1 antibody, or MCP-1 anti-idiotype antibody, in a host cell, comprising culturing a host cell as described herein under conditions wherein at least one anti-MCP-1 antibody is expressed in detectable and/or recoverable amounts.

The present invention also provides at least one composition comprising (a) an isolated anti-MCP-1 antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition.

The present invention further provides at least one anti-MCP-1 antibody method or composition, for administering a therapeutically effective amount to modulate or treat at least one MCP-1 related condition in a cell, tissue, organ, animal or patient and/or, prior to, subsequent to, or during a related condition, as known in the art and/or as described herein.

The present invention also provides at least one composition, device and/or method of delivery of a therapeutically or prophylactically effective amount of at least one anti-MCP-1 antibody, according to the present invention.

The present invention further provides at least one anti-MCP-1 antibody method or composition, for diagnosing at least one MCP-1 related condition in a cell, tissue, organ, animal or patient and/or, prior to, subsequent to, or during a related condition, as known in the art and/or as described herein.

The present invention also provides at least one composition, device and/or method of delivery for diagnosing of at least one anti-MCP-1 antibody, according to the present invention.

In one aspect, the present invention provides at least one isolated mammalian anti-MCP-1 antibody, comprising at least one variable region comprising SEQ ID NO: 27 or 28.

In another aspect, the present invention provides at least one isolated mammalian anti-MCP-1 antibody, comprising either (i) all of the heavy chain complementarity determining regions (CDR) amino acid sequences of SEQ ID NOS: 6, 7 and 8 or 9; or (ii) all of the light chain CDR amino acids sequences of SEQ ID NOS: 13, 14 and 15 or 16.

In another aspect, the present invention provides at least one isolated mammalian anti-MCP-1 antibody, comprising at least one of (i) all of the heavy chain complementarity determining regions (CDR) amino acid sequences of SEQ ID NOS: 6, 7 and 8 or 9; or (ii) all of the light chain CDR amino acids sequences of SEQ ID NOS: 13, 14 and 15 or 16.

The at least one antibody can optionally further at least one of: bind MCP-1 with an affinity of at least one selected from at least $10^{-9}$ M, at least $10^{-10}$ M, at least $10^{-11}$ M, or at least $10^{-12}$ M; substantially neutralize at least one activity of at least one MCP-1 protein. Also provided is an isolated nucleic acid encoding at least one isolated mammalian anti-MCP-1 antibody; an isolated nucleic acid vector comprising the isolated nucleic acid, and/or a prokaryotic or eukaryotic host cell comprising the isolated nucleic acid. The host cell can optionally be at least one selected from NSO, COS-1, COS-7, HEK293, BHK21, CHO, BSC-1, Hep G2, YB2/0, SP2/0, HeLa, myeloma, or lymphoma cells, or any derivative, immortalized or transformed cell thereof. Also provided is a method for producing at least one anti-MCP-1 antibody, comprising translating the antibody encoding nucleic acid under conditions in vitro, in vivo or in situ, such that the MCP-1 antibody is expressed in detectable or recoverable amounts.

Also provided is a composition comprising at least one isolated mammalian anti-MCP-1 antibody and at least one pharmaceutically acceptable carrier or diluent.

Also provided is a method for diagnosing or treating a MCP-1 related condition in a cell, tissue, organ or animal, comprising (a) contacting or administering a composition comprising an effective amount of at least one isolated mammalian anti-MCP-1 antibody of the invention with, or to, the cell, tissue, organ or animal.

Also provided is a medical device, comprising at least one isolated mammalian anti-MCP-1 antibody of the invention, wherein the device is suitable to contacting or administering the at least one anti-MCP-1 antibody by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal.

Also provided is an article of manufacture for human pharmaceutical or diagnostic use, comprising packaging material and a container comprising a solution, particulate, or a lyophilized form of at least one isolated mammalian anti-MCP-1 antibody of the present invention.

Also provided is a method for producing at least one isolated mammalian anti-MCP-1 antibody of the present invention, comprising providing a host cell or transgenic animal or transgenic plant or plant cell capable of expressing in recoverable amounts the antibody. Further provided in the present invention is at least one anti-MCP-1 antibody produced by the above method.

The present invention further provides any invention described herein.

BRIEF DESCRIPTION OF THE SEQUENCE LISTING

| SEQ ID NO: | Description |
| --- | --- |
| 1 | Human MCP-1 (CCL2) and variants used to select anti-MCP-1 binders |
| 2 | VH1A heavy chain variable sequence: FR1, CDR1, FR2, CDR2 variants, FR3, CDR3, FR4 |
| 3 | VH3 Heavy chain variable sequence: FR1, CDR1, FR2, CDR2 variants, FR3, CDR3, FR4 |
| 4 | Kappa3 light chain variable sequence: FR1, CDR1, FR2, CDR2, FR3, CDR3 variants, FR4 |
| 5 | Lambda3 light chain variable sequence: FR1, CDR1, FR2, CDR2, FR3, CDR3 variants, FR4 |
| 6 | VH1A CDR1 All MOR03471 |
| 7 | VH1A CDR2 3781, 3790, CNTO 888 |
| 8 | VH1A CDR2 3899 |
| 9 | VH1A CDR3 All MOR03471 |
| 10 | VH3 CDR1 All MOR03548 |
| 11 | VH3 CDR2 3744, 3747 |
| 12 | VH3 CDR3 All MOR03548 |

-continued

| SEQ ID NO: | Description |
|---|---|
| 13 | Kappa3 CDR1 All MOR03471 |
| 14 | Kappa3 CDR2 All MOR03471 |
| 15 | Kappa3 CDR3 3781 |
| 16 | Kappa3 CDR3 3790, CNTO888 |
| 17 | Kappa3 CDR3 3899 |
| 18 | Lamda3 CDR1 All MOR03548 |
| 19 | Lamda3 CDR2 All MOR03548 |
| 20 | Lamda3 CDR3 3744 |
| 21 | Lamda3 CDR3 3747 |
| 22 | VH1A CDR2 Variants |
| 23 | VH3 CDR2 Variants |
| 24 | Lk CDR3 Variants |
| 25 | Lλ CDR3 Variants |
| 26 | HC CDR1 Variants |
| 27 | CNTO888 Heavy Chain Variable Region |
| 28 | CNTO888 Light Chain Variable Region |

DETAILED DESCRIPTION OF THE INVENTION

The present invention provides at least one purified, isolated, recombinant and/or synthetic anti-MCP-1 human, primate, rodent, mammalian, chimeric, humanized, engineered, or CDR-grafted, antibodies and MCP-1 anti-idiotype antibodies thereto, as well as compositions and encoding nucleic acid molecules comprising at least one polynucleotide encoding at least one anti-MCP-1 antibody or anti-idiotype antibody. The present invention further includes, but is not limited to, methods of making and using such nucleic acids and antibodies and anti-idiotype antibodies, including diagnostic and therapeutic compositions, methods and devices.

Citations: All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2004); Sambrook, et al., Molecular Cloning: A Laboratory Manual, 2$^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2004); Colligan et al., Current Protocols in Protein Science, John Wiley & Sons, NY, N.Y., (1997-2004).

Abbreviations aa: amino acid; BSA: bovine serum albumin; CDR: complementarity-determining regions; ECL: electro-chemiluminescence; HuCAL®: Human Combinatorial Antibody Library; HSA: human serum albumin; MCP-1: Monocyte Chemoattractant Protein-1; Ig: Immunoglobulin; IPTG: isopropyl β-D-thiogalactoside; mAb: monoclonal antibody; PBS: phosphate buffered saline, pH 7.4; SET solution equilibrium titration; VH immunoglobulin heavy chain variable region; VL immunoglobulin light chain variable region;

DEFINITIONS

As used herein, an "anti-CCL2 antibody," "anti-MCP-1 antibody," "anti-MCP-1 antibody portion," or "anti-MCP-1 antibody fragment" and/or "anti-MCP-1 antibody variant" and the like include any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, or at least one portion of an MCP-1 receptor or binding protein, which can be incorporated into an antibody of the present invention. Such antibody optionally further affects a specific ligand, such as but not limited to where such antibody modulates, decreases, increases, antagonizes, agonizes, mitigates, alleviates, blocks, inhibits, abrogates and/or interferes with at least one MCP-1 activity or binding, or with MCP-1 receptor activity or binding, in vitro, in situ and/or in vivo. As a non-limiting example, a suitable anti-MCP-1 antibody, specified portion or variant of the present invention can bind at least one MCP-1, or specified portions, variants or domains thereof.

As used herein, "epitope" means a segment or feature of a protein capable of specific binding to an antibody. Epitopes usually consist of chemically active surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents. Protein epitopes resulting from conformational folding of the MCP-1 molecule which arise when amino acids from differing portions of the linear sequence of the MCP-1 molecule come together in close proximity in 3-dimensional space are included.

By "MCP-1" is meant the 76 amino acid sequence referenced in NCBI record accession No. NP_002973 and variously known as MCP (monocyte chemotactic protein), SMC-CF (smooth muscle cell chemotactic factor), LDCF (lymphocyte-derived chemotactic factor), GDCF (glioma-derived monocyte chemotactic factor), TDCF (tumor-derived chemotactic factors), HC11 (human cytokine 11), MCAF (monocyte chemotactic and activating factor). The gene symbol is SCYA2, the JE gene on human chromosome 17, and the new designation is CCL2 (Zlotnik, Yoshie 2000. Immunity 12:121-127). JE is the mouse homolog of human MCP-1/CCL2.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is derived from recombination events of human germline immunoglobulin gene sequences or from mature human antibody sequences. In addition to antibodies isolated humans, such a human antibody may be obtained by immunizing transgenic mice capable of mounting an immune response with human immunoglobulin germline genes (Lonberg et al., Int Rev Immunol 13(1):65-93 (1995) and Fishwald et al., Nat Biotechnol 14(7):845-851 (1996)) or may be selected from a human antibody repertoire library such as described herein. A source of such human gene sequences may be found in any suitable library such as VBASE, a database of human antibody genes (www._mrc-cpe.ca-m.ac.uk/imt-doc) or translated products thereof or at http://people.cryst.bbk.ac.uk/~ubcg07s/ which gives human antibodies classified into groupings based on their amino acid sequence similarities. With the scope of this definition, are composite antibodies or functional fragments of a human composite antibodies which include framework regions from one or more human antibody sequences and CDR regions from two different human or non-human sources. Within the definition of "human antibody" is a composite antibody or functional fragment of a human composite antibody which contains framework regions from both germline and re-arranged human antibody sequences and CDR regions from two different source antibodies. A human composite antibody or functional fragment of a human composite antibody in accordance with this disclosure includes framework regions from one or more human antibody sequences, and CDR regions derived from a human or non-human antibody sequences or may be entirely synthetic. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

"Humanized" forms of non-human (e.g., murine) antibodies are chimeric antibodies that have substantially replaced sequence portions that were derived from non-human immunoglobulin. For the most part, humanized antibodies are human immunoglobulins (recipient antibody) in which the CDR (the complementarity determining regions which are also known as the hypervariable region) residues of the recipient are replaced by CDR residues from a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human IgG immunoglobulin. For further details, see Jones et al., Nature 321:522-525 (1986); Reichmann et al., Nature 332:323-329 (1988); and Presta, Curr. Op. Struct. Biol. 2:593-596 (1992).

As used herein, Kd of an antibody refers the dissociation constant, $K_D$, the antibody for a predetermined antigen and is a measure of affinity of the antibody for a specific target. High affinity antibodies have a $K_D$ of $10^{-8}$ M or less, more preferably $10^{-9}$ M or less and even more preferably $10^{-10}$ M or less, for a predetermined antigen. The term "$K_{dis}$" or "$K_D$," or "Kd' as used herein, is intended to refer to the dissociation rate of a particular antibody-antigen interaction. The "$K_D$", is the ratio of the rate of dissociation ($k_2$), also called the "off-rate ($k_{off}$)", to the rate of association rate (k1) or "on-rate ($k_{on}$)". Thus, $K_D$ equals $k_2/k_1$ or $k_{off}/k_{on}$ and is expressed as a molar concentration (M). It follows that the smaller the $K_D$, the stronger the binding. So a $K_D$ of $10^{-6}$ M (or 1 microM) indicates weak binding compared to $10^{-9}$ M (or 1 nM).

As used herein, the terms "specificity for" and "specific binding" and "specifically binds" refers to antibody binding to a predetermined antigen with greater affinity than for other antigens or proteins. Typically, the antibody binds with a dissociation constant ($K_D$) of $10^{-7}$ M or less, and binds to the predetermined antigen with a $K_D$ that is at least twofold less than its $K_D$ for binding to a non-specific antigen (e.g., BSA, casein, or any other specified polypeptide) other than the predetermined antigen. The phrases "an antibody recognizing an antigen" and "an antibody specific for an antigen" are used interchangeably herein with the term "an antibody which binds specifically to an antigen" or "an antigen specific antibody" e.g. a MCP-1 specific antibody.

1. Preparation of Antibodies of the Invention

Preparation of human antibodies that are specific for human MCP-1 protein or fragments thereof, such as isolated and/or MCP-1 protein or a portion thereof (including synthetic molecules, such as synthetic peptides) can be performed using any suitable technique known in the art. Human antibodies can be produced using various techniques known in the art. In one embodiment, the human antibody is selected from a phage library, where that phage library expresses human antibodies (Vaughan et lo al. Nature Biotechnology 14:309-314 (1996): Sheets et al. PITAS (USA) 95:6157-6162 (1998)); Hoogenboom and Winter, J. Mol. Biol., 227:381 (1991); Marks et al. J. Mol. Biol., 222:581 (1991)).

Human antibodies can also be made by introducing human immunoglobulin loci into transgenic animals, e.g., mice in which the endogenous immunoglobulin genes have been partially or completely inactivated. For example, a transgenic mouse, comprising a functionally rearranged human immunoglobulin heavy chain transgene and a transgene comprising DNA from a human immunoglobulin light chain locus that can undergo functional rearrangement, can be immunized with human MCP-1 or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

Upon challenge with an appropriate antigen, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huezar, Intern. Rev. Immunol. 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., J. Immunol., 147 (1):86-95 (1991); and U.S. Pat. No. 5,750,373. Antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, or heteromylomas, fusion products thereof, or any cell or fusion cell derived therefrom, or any other suitable cell line as known in the art. See, e.g., www._atcc.org, www._lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Human antibodies that bind to human MCP-1 and that comprise a defined heavy or light chain variable region can be prepared using suitable methods, such as phage display (Katsube, Y., et al, *Int J Mol. Med,* 1(5):863-868 (1998)). Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; Bioinvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260 (May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); WO96/13583, WO97/08320 (MorphoSys); WO95/16027 (Bioinvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763, 192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference.

Specific Embodiment

Applicants exemplified a method of selecting and making human antibodies with the desired affinity, specificity and bioactivity towards human MCP-1 starting from a phage display human Fab library. In summary, from all 10 pannings 17856 clones were screened leading to 1104 primary hits and finally 26 unique Fabs.

In order to provide a unique ligand which exemplified an antigen retaining ability to bind to naturally occurring MCP-1 receptors, human MCP-1 and its analogs or "muteins" were chemically synthesized and modified for specific uses in selection, affinity, and biological assays. Human MCP-1 Ile$^{41}$, and human MCP-1 Tyr$^{43}$ were used in the initial solid phase panning as well as other aspects of antibody selection and affinity maturation assays and described herein as were the biotinylated versions of MCP-1 mutein: Ile41, Lys(Biotin-PEG$_4$)$^{69}$) and (Ile41, Lys(Biotin-PEG$_4$)$^{75}$ (SEQ ID NO: 1).

Because none of the 26 unique Fabs had an affinity measured as $K_D$<0.5 nM or the desired $IC_{50}$ values in specified bio-assays, maturation was essential. Candidates for the affinity maturation were selected as Fabs and the respective IgGs were analyzed in parallel to the maturation process. Selection criteria were 1) the activity in whole cell receptor binding assay, 2) the activity in calcium mobilization assay, 3) the affinity to human MCP-1, 4) the specificity to human MCP-1, and 5) the affinity to cyno MCP-1 and the binding to native MCP-1.

Biacore affinity measurements in the Fab capture mode with MCP-1 in solution worked well for ranking of the maturation candidates and the affinities were in the range of 49 to 406 nM. The best parental Fab showed an affinity of 50 nM, indicating that the affinity had to be optimized at least 100 fold to reach the affinity success criterion. In addition the binding to cynomolgus monkey and native human MCP-1 could be detected in the Fab capture mode, which was an additional pre-requisite for maturation. The affinities to cynomolgus monkey MCP-1 were in the same range as for the human MCP-1. Due to potential modifications, as for example glycosylation, it had to be shown that the antibodies did not only recognize the synthetic or recombinant MCP-1 but also the native MCP-1 which was endogenously expressed and purified from human PANC-1 cell supernatant.

Specificity to MCP-1 was measured in the antibody capture mode in Biacore, adding 100 nM of each chemokine and detecting the binding signal. Most of the candidate Fabs for maturation were specific, while a couple showed some cross-reactivity to homologue chemokines.

A very important feature of the Fab was the neutralizing activity and several different assays were set up to analyze this activity. $^{125}$I MCP-1 THP-1 cell binding assay was the most sensitive assay, which was especially important after the optimization. The parental Fabs showed $IC_{50}$ values from 10-650 nM. Beside the radio ligand binding assay other secondary bioassays were planned to prove the neutralizing activity at different levels of the downstream signaling pathway of MCP-1.

Attraction of monocytes is one of the major functions of MCP-1 but most probably due to missing activity, co-purified factors or endotoxin the parental Fabs did not work in the chemotaxis assay and therefore it was agreed to test the respective IgG1 only, instead of trying to get the Fabs working in this assay. Another downstream signaling event is the calcium release into the cytoplasm. Indeed all Fabs, that showed neutralizing activity in the radio ligand binding assay, inhibited the MCP-1 induced calcium mobilization in THP-1 cells with an a $IC_{50}$ range from 0.1 to 3 µM. It had to be shown that the biological activity of the parental Fabs was completely retained after conversion into the IgG format. As expected all respective IgG showed activity in the radio ligand binding assay, the calcium mobilization assay and even the chemotaxis assay, finally proving that all IgGs retained the activities seen in the Fab format and even inhibited MCP-1 induced chemotaxis.

For affinity maturation, seven different Fabs with $K_D$ in the range of 10-400 nM and $IC_{50}$ values in the range of 10-650 nM in the radio ligand binding assay were selected according to their characteristics. Subsequently they were grouped into 3 groups for the library cloning and the subsequent selection. L-CDR3 and H-CDR2 optimization were performed in parallel. High quality libraries were generated. Solution panning was used for the selection process and the stringency of selection was increased by reduction of antigen, off-rate selection and very long washing steps. For the following screening process a BioVeris screening was used allowing high throughput ranking of the optimized binders. The screening worked very efficiently for identification of improved binders. In addition Fabs optimized in L-CDR3 and H-CDR2 could be identified, making cross-cloning possible for MOR03471 and MOR03548 derivatives. Especially the cross-cloning of MOR03471 derivatives was very successful leading up to a further 100 fold improved affinity compared to the two optimized starting Fabs. Of the 17 optimized Fabs, 16 were selected for detailed characterization and finally the 4 binders, that met all success criteria, derived from parental MOR03471, two were optimized in L-CDR3 only and two came from cross-cloning. The affinity matured candidate analyses and sequences are detailed in Examples 3 and 4, Tables 4-6, and SEQ ID Nos: 2-28.

After maturation, the affinity of the optimized binders could not be analyzed in Biacore mainly as the detection limits were reached. At MorphoSys a very sensitive $K_D$ determination method was used, being solution equilibrium titration (SET) combined with BioVeris technology. Monovalent dissociation constants could be calculated by means of appropriate fit models for Fab and IgG. In addition to affinity measurement, this method was used for cross-reactivity studies. The affinities of the final candidates were in the range of 10 to 320 pM to human and cynomolgus MCP-1 measured in BioVeris and confirmed by KinexA at Centocor. Specificity testing using BioVeris showed no cross-reactivity to human MCP-2 for all tested 16 Fabs and IgGs. Several Fab and IgG showed also no significant cross-reactivity to human Eotaxin. According to the success criteria, the specificity criterion was fixed as no binding to 100 nM homologue human MCP-2, 3, 4 and 100 nM human Eotaxin 1, 2 and 3 in Biacore antibody capture mode. In Biacore Fab capture mode all selected Fabs showed different extent of cross-reactivity with MCP-2 and Eotaxin. The putative slightly increased instability of Fabs compared to IgGs and the general unspecific binding capacity of chemokines might have contributed to unspecific binding. Several of the selected IgG showed no significant binding signal to the homologue chemokines and met the specificity success criteria in Biacore IgG capture mode. In solution equilibrium titration experiments using BioVeris even several Fabs showed no cross-reactivity. To analyze if the Fab binding activity to MCP-2 detected in Biacore translates into neutralizing activity, radio ligand whole cell binding assays were developed at Centocor. Fabs tested in this assay showed no significant inhibition of 125I labeled MCP-2 binding to CCR2 receptor on Thp-1 cells (IC50≧2 μM).

Due to the low amount of 1 ng/ml MCP-1 needed, the radio ligand binding assay was the most sensitive assay in this project with an assay $IC_{50}$ limit of about 100 pM for Fab and even 20 pM for IgG. Beside affinity, the activity in this assay was used for ranking and selection of optimized binders for detailed characterization. The overall improvement in activity during optimization was up to a factor of 1000× and finally one MOR03471 derived Fab, MOR03878, showed the highest affinity at 110 pM. All tested IgG retained the activity in the radio ligand binding assay. $IC_{50}$ values of the 4 final IgG candidates MOR03781, MOR03790, MOR03850 and MOR03878 were in the range of 20-50 pM, being even slightly better compared to the respective activity of the Fabs. One reason for the improved activity is that bivalent IgG neutralize two MCP-1 per molecule (factor 2×). The IgGs came from a pure up-scaled production and therefore another reason might have been the purity, stability or activity of the antibodies. As secondary bio-assay a FACS based assay, measuring the inhibition of MCP-1 induced CCR2 receptor internalization, was successfully developed. Finally the assay even allowed $IC_{50}$ determination and ranking. The final 4 candidate Fabs, MOR03790, MOR03850, MOR03781 and MOR03878 showed $IC_{50}$ values in the range of 3 to 5 nM.

Native MCP-1 was needed to confirm the activities of the MCP-1 antibodies isolated against the synthetic or the recombinant MCP-1. Native MCP-1 was purified from PANC1 supernatant and used for the induction of calcium release. Optimized Fabs showed inhibition of native MCP-1 induced calcium mobilization with higher activity compared to the reference antibody C775. All MOR03548 derived pre-selected Fabs completely inhibited binding of C775 to MCP1 in a competition ELISA. All MOR03471 derived pre-selected Fabs showed partial (~60%) competition in ELISA, indicating that the epitopes are at least overlapping. Finally the four antibodies MOR03781, MOR03790, MOR03850 and MOR03878 fulfilled all success criteria including specificity criterion and the neutralization of native MCP-1.

Other Suitable Methods of Producing Antibodies

Other methods for producing the antibodies of the invention that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source which is non-human, e.g., but not limited to, mouse, rat, rabbit, non-human primate or other mammal. These human amino acid residues are often referred to as "import" residues, which are typically taken from an "import" variable, constant or other domain of a known human sequence. Known human Ig sequences are well known in the art and can any known sequence. Various strategies for optimizing the binding, conformation, and reduced immunogenicity of engineered humanized antibodies have been described in see e.g. Presta et al. J. Immunol. 151:2623-2632, 1993; WO200302019, and WO2005080432.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976, 862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

Transgenic mice that can produce a repertoire of human antibodies that bind to human antigens can be produced by known methods (e.g., but not limited to, U.S. Pat. Nos. 5,770, 428, 5,569,825, 5,545,806, 5,625,126, 5,625,825, 5,633,425, 5,661,016 and 5,789,650 issued to Lonberg et al.; Jakobovits et al WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al GB 2 272 440 A, Lonberg et al. Nature 368:856-859 (1994), Taylor et al., Int. Immunol. 6(4)579-591 (1994), Green et al, Nature Genetics 7:13-21 (1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7): 845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278. Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5,885,793, assigned to Cambridge antibody Technologies; U.S. Pat. No. 5,750,373, assigned to Genentech, U.S. Pat. Nos. 5,618,920, 5,595,898, 5,576,195, 5,698,435, 5,693, 493, 5,698,417, assigned to Xoma, Colligan, supra; Ausubel, supra; or Sambrook, supra, each of the above patents and publications entirely incorporated herein by reference.

2. Nucleic Acids of the Invention.

Using the information provided herein, such as the nucleotide sequences encoding at least 70-100% of the contiguous amino acids of at least one of SEQ ID NOS: 2-5 and 27-28, specified fragments, variants or consensus sequences thereof, a nucleic acid molecule of the present invention encoding at least one anti-MCP-1 antibody can be obtained using methods described herein or as known in the art. Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain (e.g., SEQ ID NOS: 6-12, 22 and 23) or light chain (e.g., SEQ ID NOS: 13-21 and 24-26); nucleic acid molecules comprising the coding sequence for an anti-MCP-1 antibody or variable region (e.g., SEQ ID NOS:2-5, 27 and 28); and nucleic acid molecules which comprise a nucleotide sequence substantially different from those described above but which, due to the degeneracy of the genetic code, still encode at least one anti-MCP-1 antibody as described herein and/or as known in the art. Of course, the genetic code is well known in the art. Thus, it would be routine for one skilled in the art to generate such degenerate nucleic acid variants that code for specific anti-MCP-1 antibodies of the present invention. See, e.g., Ausubel, et al., supra, and such nucleic acid variants are included in the present invention.

As indicated herein, nucleic acid molecules of the present invention which comprise a nucleic acid encoding an anti-MCP-1 antibody can include, but are not limited to, those encoding the amino acid sequence of an antibody fragment, by itself, the coding sequence for the entire antibody or a portion thereof, the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Which Selectively Hybridize to a Polynucleotide as Described Herein: The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids: The isolated nucleic acids of the present invention can be made using (a) recombinant methods, (b) synthetic techniques, (c) purification techniques, or combinations thereof, as well-known in the art.

Recombinant Methods for Constructing Nucleic Acids: The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

Nucleic Acid Screening and Isolation Methods: A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein. Known methods of DNA or RNA amplification include, but are not limited to, polymerase chain reaction (PCR) and related amplification processes (Mullis, et al., U.S. Pat. No. 4,683,202 (1987); and Innis, et al., PCR Protocols A Guide to Methods and Applications, Eds., Academic Press Inc., San Diego, Calif. (1990).

Synthetic Methods for Constructing Nucleic Acids: The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences. A particularly preferred method for chemical synthesis of coding sequences is taught in U.S. Pat. Nos. 6,521, 427 and 6,670,127.

3. Vectors and Expression Systems

The invention provides vectors, preferably, expression vectors, containing a nucleic acid encoding the anti-MCP-1 antibody, or may be used to obtain plasmids containing various antibody HC or LC genes or portions thereof. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. The present invention also relates to vectors that include isolated nucleic acid molecules of the present invention, host cells that are genetically engineered with the recombinant vectors, and the production of at least one anti-MCP-1 antibody by recombinant techniques, as is well known in the art. See, e.g., Sambrook, et al., supra; Ausubel, et al., supra, each entirely incorporated herein by reference.

For expression of the antibodies, or antibody fragments thereof, DNAs encoding partial or full-length light and heavy chains, can be inserted into expression cassettes or vectors such that the genes are operatively linked to transcriptional and translational control sequences. A cassette which encodes an antibody, can be assembled as a construct. A construct can be prepared using methods known in the art. The construct can be prepared as part of a larger plasmid. Such preparation allows the cloning and selection of the correct constructions in an efficient manner. The construct can be located between convenient restriction sites on the plasmid or other vector so that they can be easily isolated from the remaining plasmid sequences.

Generally, a plasmid vector is introduced in a precipitate, such as a calcium phosphate precipitate, or in a complex with a charged lipid of DEAE-dextran. If the vector is a virus, it can be packaged in vitro using an appropriate packaging cell line and then transduced into host cells. Introduction of a vector construct into a host cell can also be effected by electroporation or other known methods. Such methods are described in the art, such as Sambrook, supra, Chapters 1-4 and 16-18; Ausubel, supra, Chapters 1, 9, 13, 15, 16.

In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present).

The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VI, segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

In general, a mammalian expression vector will contain (1) regulatory elements, usually in the form of viral promoter or enhancer sequences and characterized by a broad host and tissue range; (2) a "polylinker" sequence, facilitating the insertion of a DNA fragment which comprises the antibody coding sequence within the plasmid vector; and (3) the sequences responsible for intron splicing and polyadenylation of mRNA transcripts. This contiguous region of the promoter-polylinker-polyadenylation site is commonly referred to as the transcription unit. The vector will likely also contain (4) a selectable marker gene(s) (e.g., the beta-lactamase gene), often conferring resistance to an antibiotic (such as ampicillin), allowing selection of initial positive transformants in E. coli; and (5) sequences facilitating the replication of the vector in both bacterial and mammalian hosts. A plasmid origin of replication are included for propagation of the expression construct in E. coli and for transient expression in Cos cells, the SV40 origin of replication is included in the expression plasmid.

A promoter may be selected from a SV40 promoter, (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art. Also, to avoid high surface expression of heavy chain molecules, it may be necessary to use an expression vector that eliminates transmembrane domain variant splices.

Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRESlneo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRS-Vcat (ATCC 37152), pSV2dhfr (ATCC 37146) and pBC12MI (ATCC 67109).

Alternatively, the nucleic acids encoding the antibody sequence can be expressed in stable cell lines that contain the gene integrated into a chromosome. The co-transfection with a selectable marker such as dhfr, gpt, neomycin, or hygromycin allows the identification and isolation of the transfected cells which express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The DNA constructs used in the production of the antibodies of the invention can optionally include at least one insulator sequence. The terms "insulator", "insulator sequence" and "insulator element" are used interchangeably herein. An insulator element is a control element which insulates the transcription of genes placed within its range of action but which does not perturb gene expression, either negatively or positively. Preferably, an insulator sequence is inserted on either side of the DNA sequence to be transcribed. For example, the insulator can be positioned about 200 bp to about 1 kb, 5' from the promoter, and at least about 1 kb to 5 kb from the promoter, at the 3' end of the gene of interest. The distance of the insulator sequence from the promoter and the 3' end of the gene of interest can be determined by those skilled in the art, depending on the relative sizes of the gene of interest, the promoter and the enhancer used in the construct. In addition, more than one insulator sequence can be positioned 5' from the promoter or at the 3' end of the transgene. For example, two or more insulator sequences can be positioned 5' from the promoter. The insulator or insulators at the 3' end of the transgene can be positioned at the 3' end of the gene of interest, or at the 3' end of a 3' regulatory sequence, e.g., a 3' untranslated region (UTR) or a 3' flanking sequence.

Examples of suitable inducible non-fusion *E. coli* expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident λ prophage harboring a T7 gn1 gene under the transcriptional control of the lacUV 5 promoter.

In another embodiment, the expression vector is a yeast expression vector. Examples of vectors for expression in yeast *S. cerevisiae* include pYepSec1 (Baldari et al. (1987) EMBO J. 6:229-234), pMFa (Kurjan and Herskowitz, (1982) Cell 30:933-943), pJRY88 (Schultz et al. (1987) Gene 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) Mol. Cell. Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells, see chapters 16 and 17 of Sambrook et al., supra.

In another embodiment, the recombinant mammalian expression vector is capable of directing expression of the nucleic acid, preferentially in a particular cell type, such as lymphoma cells (e.g., mouse myeloma cells). In specific cell types, tissue-specific regulatory elements are used to express the nucleic acid. Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular, promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example, by the murine hox promoters (Kessel and Gruss (1990) Science 249:374-379) and the α-fetoprotein promoter (Campes and Tilghman (1989) Genes Dev. 3:537-546).

The invention further provides a recombinant expression vector comprising a DNA molecule cloned into the expression vector in an antisense orientation. That is, the DNA molecule is operably linked to a regulatory sequence in a manner that allows for expression (by transcription of the DNA molecule) of an RNA molecule that is antisense to the mRNA encoding a polypeptide. Regulatory sequences operably linked to a nucleic acid cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub et al. (Reviews—Trends in Genetics, Vol. 1(1) 1986).

Cloning and Expression in Myeloma Cells

A chimeric mouse/human IgG1k monoclonal antibody against human CD4, known as cM-T412 (EP0511308 entirely incorporated by reference), was observed to be expressed at high levels in transfected mouse myeloma cells (Looney et al. 1992. Hum Antibodies Hybridomas 3(4):191-200). Without a large effort at optimizing culture conditions, production levels of >500 mg/L (specific productivity on a pg/cell/day basis not known) were readily obtained at Centocor, Inc. Malvern, Pa. in 1990. Based on the components of these expression vectors antibody-cloning vectors were developed useful for HC and LC cloning which include the gene promoter/transcription initiation nucleic acid sequence, the 5' untranslated sequences and translation initiation nucleic acid sequences, the nucleic acid sequences encoding the signal sequence, the intron/exon splice donor sequences for the signal intron and the J-C intron, and the J-C intron enhancer nucleic acid sequences. Plasmid p139, a pUC19 plasmid, contains a 5.8 kb EcoRI-EcoRI genomic fragment cloned from C123 hybridoma cells secreting the fully mouse M-T412 Ab; the fragment contains the promoter and V region part of the cM-T412 HC gene. The starting material for LC V region vector engineering was plasmid p39, a pUC plasmid that contains a 3 kb HindIII-HindIII genomic fragment cloned from C123 hybridoma cells; this fragment contains the promoter and V region part of the cM-T412 LC gene. The engineered vectors derived from p139 and p39 were designed to enable convenient assembly of HC or LC genes suitable for expression in a mammalian host cell in a two-step process that entails 1) cloning DNA encoding a sequence of interest between specially-prepared restriction sites in a V region vector, whereby the V-region coding sequence is positioned immediately downstream of the vector-encoded signal sequence, as well as downstream of part or all of the gene promoter; and 2) transferring a fragment that spans the inserted sequence from the V region vector to the C region vector in the proper orientation whereby the resulting plasmid constitutes the final expression plasmid suitable for expression in cells (Scallon et al. 1995 Cytokine 7(8):759-769).

Cloning and Expression in CHO Cells

Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990); and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438-447 (1985)) plus a fragment isolated from the enhancer of the immediate early gene of human cytomegalovirus (CMV) (Boshart, et al., Cell 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the MCP-1 antibody in a regulated way in mammalian cells (M. Gossen, and H. Bujard, Proc. Natl. Acad. Sci. USA 89: 5547-5551 (1992)). For the polyadenylation of the mRNA other signals, e.g., from the human growth hormone or globin genes can be used as well.

4. Host Cells for Production of Antibodies

At least one anti-MCP-1 antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2004); Sambrook, et al., Molecular Cloning: A Laboratory Manual, 2$^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2004); Colligan et al., Current Protocols in Protein Science, John Wiley & Sons, NY, N.Y., (1997-2004), each entirely incorporated herein by reference.

In order to produce biopharmaceutical products, a production cell line capable of efficient and reproducible expression of a recombinant polypeptide(s) is required. The cell line is stable and bankable. A variety of host cell lines can be employed for this purpose. As the understanding of the complexities of how the cellular machinery impact the final amount and composition of a biotherapeutic product, the selection of a host cell line which will impart the needed attributes to the production and the composition of the product become more evident.

Unlike most genes that are transcribed from continuous genomic DNA sequences, antibody genes are assembled from gene segments that may be widely separated in the germ line. In particular, heavy chain genes are formed by recombination of three genomic segments encoding the variable (V), diversity (D) and joining (J)/constant (C) regions of the antibody. Functional light chain genes are formed by joining two gene segments; one encodes the V region and the other encodes the J/C region. Both the heavy chain and kappa light chain loci contain many V gene segments (estimates vary between 100 s and 1000 s) estimated to span well over 1000 kb. The lambda locus is, by contrast, much smaller and has been shown to span approximately 300 kb on chromosome 16 in the mouse. It consists of two variable gene segments and four joining/constant (J/C) region gene segments. Formation of a functional gene requires recombination between a V and a J/C element.

In the B-cell in which the antibody is naturally produced, control of transcription of both rearranged heavy and kappa light chain genes depends both on the activity of a tissue specific promoter upstream of the V region and a tissue specific enhancer located in the J-C intron. These elements act synergistically. Also, a second B-cell specific enhancer has been identified in the kappa light chain locus. This further enhancer is located 9 kb downstream of $C_{kappa}$. Thus, the hybridoma method of immortalizing antibody expression genes relies on the endogenous promoter and enhancer sequences of the parent B-cell lineage. Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Cloning of antibody genomic DNA into an artificial vector is another method of creating host cells capable of expressing antibodies. However, expression of monoclonal antibodies behind a strong promoter increases the chances of identifying high-producing cell lines and obtaining higher yields of monoclonal antibodies. Antibodies of the invention can be produced in a host cell transfectoma using, for example, a combination of recombinant DNA techniques and gene transfection methods as is well known in the art (e.g., Morrison, S. (1985) Science 229:1202).

Systems for cloning and expression of a biopharmaceuticals, including antibodies, in a variety of different host cells are well known. Suitable host cells include bacteria, mammalian cells, plant cells, yeast and baculovirus systems and transgenic plants and animals. Mammalian cell lines available in the art for expression of a heterologous polypeptide intact glycosylated proteins include Chinese hamster ovary (CHO) cells, HeLa cells, baby hamster kidney cells (BHK), NSO mouse melanoma cells and derived cell lines, e.g. SP2/0, YB2/0 (ATC CRL-1662) rat myeloma cells, human embryonic kidney cells (HEK), human embryonic retina cells PerC.6 cells, hep G2 cells, BSC-1 (e.g., ATCC CRL-26) and many others available from, for example, American Type Culture Collection, Manassas, Va. (www._atcc.org). A common, preferred bacterial host is *E. coli*.

Mammalian cells such as CHO cells, myeloma cells, HEK293 cells, BHK cells (BHK21, ATCC CRL-10), mouse Ltk-cells, and NIH3T3 cells have been frequently used for stable expression of heterologous genes. In contrast, cell lines such as Cos (COS-1 ATCC CRL 1650; COS-7, ATCC CRL-1651) and HEK293 are routinely used for transient expression of recombinant proteins.

Preferred mammalian host cells for expressing the recombinant antibodies of the invention include myeloma cells such as Sp2/0, YB2/0 (ATC CRL-1662), NSO, and P3×63.Ag8.653 (e.g. SP2/0-Ag14) because of their high rate of expression. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Illustrative of cell cultures useful for the production of the antibodies, specified portions or variants thereof, are mammalian cells. Mammalian cell systems often will be in the form of monolayers of cells although mammalian cell suspensions or bioreactors can also be used.

A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www._atcc.org). Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851).

CHO-K1 and DHFR-CHO cells DG44 and DUK-B11 (G. Urlaub, L. A. Chasin, 1980. Proc. Natl. Acad. Sci. U.S.A. 77, 4216-4220) are used for high-level protein production because the amplification of genes of interest is enabled by the incorporation of a selectable, amplifiable marker, DHFR using e.g. the drug methotrexate (MTX) (R. J. Kaufman, 1990. Methods Enzymol. 185: 537-566). DHFR$^-$ CHO cells can be successfully used to produce recombinant mAbs at a high level. DHFR CHO may produce ant-MCP-1 antibodies at the rate of 80-110 mg $10^6$ cells$^{-1}$ day$^{-1}$ or more than 200 mg $10^6$ cells$^{-1}$ day$^{-1}$. A variety of promoters have been used to obtain expression of H- and L-chains in these CHO cells, for example, the b-actin promoter, the human CMV MIE promoter, the Ad virus major late promoter (MLP), the RSV promoter, and a murine leukemia virus LTR. A number of vectors for mAb expression are described in the literature in which the two Ig chains are carried by two different plasmids with an independent selectable/amplifiable marker. Vectors containing one antibody chain, e.g. the H-chain, linked to a DHFR marker, and an L-chain expression cassette with the Neo$^r$ marker or vice versa to can be used obtain up to 180 mg of a humanized mAb L$^{-1}$ 7 day$^{-1}$ in spinner flasks. The methods used for initial selection and subsequent amplification can be varied and are well known to those skilled in the art. In general, high-level mAb expression can be obtained using the following steps: initial selection and subsequent amplification of candidate clones, coselection (e.g., in cases where both H-chain and L-chain expression vectors carry DHFR expression unit) and amplification, coamplification using different amplifiable markers, and initial selection and amplification in mass culture, followed by dilution cloning to identify individual high-expressing clones. Because integration sites may influence the efficiency of H-chain and L-chain expression and overall mAb expression, single vectors have been created in which the two Ig-chain expression units are placed in tandem. These vectors also carry a dominant selectable marker such as Neo$^r$ and the DHFR expression cassette. For a review see Ganguly, S. and A. Shatzman. Expression Systems, mammalian cells IN: Encyclopedia of Bioprocess Technology: Fermentation, Biocatalysis, and Bioseparation. 1999 by John Wiley & Sons, Inc.

Cockett et al. (1990. Bio/Technology 8, 662-667) developed the GS system for high-level expression of heterologous genes in CHO cells. Transfection of an expression vector containing a cDNA (under the transcriptional control of the hCMV promoter) and a GS mini gene (under the control of the SV40 late promoter) into CHO-K1 cells (followed by selection with 20 mM to 500 mM MSX) can be used to yield clones expressing the antibodies of the invention in yields comparable to that of the DHFR-CHO systems. The GS system is discussed in whole or part in connection with European Patent Nos. 0 216 846, 0 256 055, and 0 323 997 and European Patent Application No. 89303964.4.

As a non-limiting example, transgenic tobacco leaves expressing recombinant proteins have been successfully used to provide large amounts of recombinant proteins, e.g., using an inducible promoter. See, e.g., Cramer et al., Curr. Top. Microbiol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and reference cited therein. Thus, antibodies of the present invention can also be produced using transgenic plants, according to know methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. See, also generally for plant expression of antibodies, but not limited to, U.S. Pat. No. 5,959,177. Each of the above references is entirely incorporated herein by reference.

5. Purification of an Antibody

An anti-MCP-1 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

6. Antibodies of the Invention

Anti-MCP-1 antibodies (also termed anti-CCL-2 antibodies or MCP-1 antibodies) useful in the methods and compositions of the present invention can optionally be characterized by high affinity binding to MCP-1, highly specific binding to MCP-1, ability to inhibit one or more of the biologic activities associated with MCP-1, and optionally and preferably having low toxicity.

The antibodies of the invention can bind human MCP-1 with a wide range of affinities ($K_D$). In a preferred embodiment, at least one human mAb of the present invention can optionally bind human MCP-1 with high affinity. For example, a human mAb can bind human MCP-1 with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the standard solutions and buffers described herein.

The isolated antibodies of the present invention comprise an antibody amino acid sequences disclosed herein encoded by any suitable polynucleotide, or any isolated or prepared antibody. Preferably, the human antibody or antigen-binding fragment binds human MCP-1 and, thereby partially or substantially neutralizes at least one biological activity of the protein. An antibody, or specified portion or variant thereof, that partially or preferably substantially neutralizes at least one biological activity of at least one MCP-1 protein or fragment can bind the protein or fragment and thereby inhibit activities mediated through the binding of MCP-1 to a MCP-1 receptor or through other MCP-1-dependent or mediated mechanisms. As used herein, the term "neutralizing antibody" refers to an antibody that can inhibit an MCP-1-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-MCP-1 antibody to inhibit an MCP-1-dependent activity is preferably assessed by at least one suitable MCP-1 protein or receptor assay, as described herein and/or as known in the art. A human antibody of the invention can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4. Antibodies of this type can be prepared by employing a transgenic mouse or other transgenic non-human mammal comprising at least one human light chain (e.g., IgG, IgA, and IgM (e.g., γ1, γ2, γ3, γ4) transgenes as described herein and/or as known in the art. In another embodiment, the anti-human MCP-1 human antibody comprises an IgG1 heavy chain and an IgG1 light chain.

At least one antibody of the invention binds at least one specified epitope specific to at least one MCP-1 protein, fragment, portion or any combination thereof. The at least one epitope can comprise at least one antibody binding region that comprises at least one portion of the protein, which epitope is preferably comprised of at least 1-3 amino acids to the entire specified portion of contiguous amino acids of the SEQ ID NO: 1.

Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. As a non-limiting example, the antibody or antigen-binding portion or variant can comprise at least one of the heavy chain CDR3 having the amino acid sequence of SEQ ID NO: 90R12, and/or a light chain CDR3 having the amino acid sequence of SEQ ID NO: 15-17, 20 OR 21. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2, and/or 3 (e.g., SEQ ID NOS: 6-12 and/or 22, 23, and 26). In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 (e.g., SEQ ID NOS: 13-21 and/or 24 and 25). In a preferred embodiment the three heavy chain CDRs and the three light chain CDRs of the antibody or antigen-binding fragment an amino acid sequence derived from the corresponding CDR of at least one of Fab MOR0336, MOR03464, MOR03468, MOR03470, MOR03471, MOR03473, MOR03548, as described herein and the heavy chain framework regions derived from a VH3 antibody (SEQ ID NO. 2) and the light chain framework regions derived from the a kappa-type antibody (SEQ ID No. 4). Such antibodies can be prepared by chemically joining together the various portions (the CDRs and frameworks) of the antibody using conventional techniques, by preparing and expressing a nucleic acid molecule that encodes the antibody using conventional techniques of recombinant DNA technology or by using any other suitable method.

The anti-MCP-1 antibody can comprise at least one of a heavy or light chain variable region having a defined amino acid sequence in the framework regions. For example, in a preferred embodiment, the anti-MCP-1 antibody comprises at least one of at least one heavy chain variable region, optionally having the amino acid sequence of SEQ ID NO: 2 or 3 and/or at least one light chain variable region, optionally having the amino acid sequence of SEQ ID NO: 4 or 5.

Antibody class or isotype (IgA, IgD, IgE, IgG, or IgM) is conferred by the constant regions that are encoded by heavy chain constant region genes. Among human IgG class, there are four subclasses or subtypes: IgG1, IgG2, IgG3 and IgG4 named in order of their natural abundance in serum starting from highest to lowest. IgA antibodies are found as two subclasses, IgA1 and IgA2. As used herein, "isotype switching" also refers to a change between IgG subclasses or subtypes.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human MCP-1 with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g, charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

An anti-MCP-1 antibody of the present invention can include one or more amino acid substitutions, deletions or additions, either from natural mutations or human manipulation, as specified herein or as taught in Knappik et al. U.S. Pat. No. 6,828,422 for variable regions derived from human germline gene sequences and categorized by sequence similarities into families designated as VH1A, VH1B, VH2, etc. and by light chains as kappa or lambda subgroups. These sequences and other sequences that can be used in the present invention, include, but are not limited to the configurations presented in Table 1, as further described FIGS. 1-42 of PCT publication WO 05/005604 and U.S. Ser. No. 10/872,932, filed Jun. 21, 2004, entirely incorporated by reference herein, wherein the referenced FIGS. 1-42 show examples of heavy and light chain variable and constant domain sequences, frameworks, subdomains, regions, and substitutions, portions of which can be used in Ig derived proteins of the present invention, as taught herein.

described above. Generally speaking, the number of amino acid substitutions, insertions or deletions for any given anti-MCP-1 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-MCP-1 antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one MCP-1 neutralizing activity. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

Anti-MCP-1 antibodies of the present invention can include, but are not limited to, at least one portion, sequence or combination selected from 5 to all of the contiguous amino acids of at least one of SEQ ID NOS: 2-5 and 27-28.

An anti-MCP-1 antibody can further optionally comprise a polypeptide of at least one of SEQ ID NOS: 27 and 28. In one embodiment, the amino acid sequence of an immunoglobulin chain, or portion thereof has about 100% identity to the amino acid sequence of the corresponding chain of at least one of SEQ ID NOS: 27-28 but for conservative substitutions which do not change the binding specificity of the anti-MCP-1 antibody. For example, the amino acid sequence of a light chain variable region can be compared with the sequence of SEQ ID NO: 4 or 5, or the amino acid sequence of a heavy chain can be compared with SEQ ID NO: 2 or 3. Preferably, the amino acid identity is determined using a suitable computer algorithm, as known in the art.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-1000% of that of the native (non-synthetic), endogenous or related and known antibody. Methods of assaying and quantifying measures of enzymatic activity and substrate specificity, are well known to those of skill in the art and described herein.

In another aspect, the invention relates to human antibodies and antigen-binding fragments, as described herein, which are modified by the covalent attachment of an organic moiety.

TABLE 1

Human Antibody Configurations

| | | | REGIONS | | | | | |
|---|---|---|---|---|---|---|---|---|
| Heavy chain variable region | | FR1 | CDR1 | FR2 | CDR2 | FR3 | CDR3 | FR4 |
| Light chain variable region | | FR1 | CDR1 | FR2 | CDR2 | FR3 | CDR3 | FR4 |
| IgA1, IgA2, IgD, IgG1, IgG2, IgG3, IgG4 | Constant Regions | CH1 | Hinge1-4 | CH2 | CH3 | | | |
| SIgA, IgM | | CH1 | Hinge1-4 | CH2 | CH3 | J-chain | | |
| IgE | | CH1 | | CH2 | CH3 | CH4 | | |

The number of amino acid substitutions a skilled artisan would make depends on many factors, including those Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-$\Delta$9-octadecanoate ($C_{18}$, oleate), all cis-$\Delta$5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acryloyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphoramide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al, *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., Bioconjugate Techniques, Academic Press: San Diego, Calif. (1996).

7. Anti-Idiotype Antibodies to Anti-MCP-1 Antibodies

In addition to monoclonal or chimeric anti-MCP-1 antibodies, the present invention is also directed to an anti-idiotypic (anti-Id) antibody specific for such antibodies of the invention. An anti-Id antibody is an antibody which recognizes unique determinants generally associated with the antigen-binding region of another antibody. The anti-Id can be prepared by immunizing an animal of the same species and genetic type (e.g. mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

8. Antibody Compositions Comprising Further Therapeutically Active Ingredients

The composition can optionally further comprise an effective amount of at least one compound or protein selected from at least one of a dermatological drug, an anti-inflammatory drug, an analgesic, a renal drug (e.g., an angiotensin receptor blocker (ARB) or antagonist), an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see., e.g., Nursing 2001 Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmacotherapy Handbook, Wells et al., ed., Appleton & Lange, Stamford, Conn., each entirely incorporated herein by reference).

Anti-MCP-1 antibody compositions of the present invention can further comprise at least one of any suitable and effective amount of a composition or pharmaceutical composition comprising at least one anti-MCP-1 antibody to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, enteracept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalazine), a muscle relaxant, a narcotic, a nonsteroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), a chronic obstructive pulmonary disease (COPD) agent, an anti-fibrotic agent, an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-29. Suitable dosages are well known in the art. See, e.g., Wells et al., eds., Pharmacotherapy Handbook, 2$^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii*, and *Shigella sonnei*), *Salmonella* species (e.g., *Salmonella typhi, Salmonella choleraSuis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa*, and Streptococci. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., *The Merck Manual*, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Anti-MCP-1 antibody compounds, compositions or combinations of the present invention can further comprise at least one of any suitable auxiliary agent, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences*, 18$^{th}$ Edition, Mack Publishing Co. (Easton, Pa.) 1990. Pharmaceutically acceptable carriers can be routinely selected that are suitable for the mode of administration, solubility and/or stability of the anti-MCP-1 antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-MCP-1 antibody compositions can also include a buffer or a pH-adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, anti-MCP-1 antibody compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as TWEEN 20®), lipids (e.g., phospholipids, fatty acids), steroids (e.g., cholesterol), and chelating agents (e.g., EDTA).

These and additional known pharmaceutical excipients and/or additives suitable for use in the anti-MCP-1 antibody, portion or variant compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

9. Formulations

As noted above, the invention provides for stable formulations suitable for pharmaceutical or veterinary use, comprising at least one anti-MCP-1 antibody in a pharmaceutically acceptable formulation.

As noted above, the invention provides an article of manufacture, comprising packaging material and at least one vial comprising a solution of at least one anti-MCP-1 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-MCP-1 antibody, and a second vial comprising an aqueous diluent of prescribed buffer or preservative, wherein said packaging material comprises a label that instructs a patient to reconstitute the at least one anti-MCP-1 antibody in the aqueous diluent to form a solution that can be held over a period of twenty-four hours or greater.

The range of at least one anti-MCP-1 antibody in the product of the present invention includes amounts yielding upon reconstitution, if in a wet/dry system, concentrations from about 1.0 μg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

The aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g., isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like TWEEN 20® (polyoxyethylene (20) sorbitan monolaurate), TWEEN 40® (polyoxyethylene (20) sorbitan monopalmitate), TWEEN 80® (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block copolymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-MCP-1 antibody and a buffered solution in quantities sufficient to provide the protein at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as solutions or as dual vials comprising a vial of lyophilized at least one anti-MCP-1 antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The claimed products can be provided indirectly to patients by providing to pharmacies, clinics, or other such institutions and facilities, clear solutions or dual vials comprising a vial of lyophilized at least one anti-MCP-1 antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, NovoPen®, B-D® Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickinson (Franklin Lakes, N.J., www._bectondickenson.com), Disetronic (Burgdorf, Switzerland, www._disetronic.com; Bioject, Portland, Oreg. (www._bioject.com); National Medical Products, Weston Medical (Peterborough, UK, www._weston-medical.com), Medi-Ject Corp (Minneapolis, Minn., www._mediject.com). Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one anti-MCP-1 antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

Other formulations or methods of stabilizing the anti-MCP-1 antibody may result in other than a clear solution of lyophilized powder comprising said antibody. Among non-clear solutions are formulations comprising particulate suspensions, said particulates being a composition containing the anti-MCP-1 antibody in a structure of variable dimension and known variously as a microsphere, microparticle, nanoparticle, nanosphere, or liposome. Such relatively homogenous essentially spherical particulate formulations containing an active agent can be formed by contacting an aqueous phase containing the active and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymer selected from the group consisting of gleatin agar, starch, arabinogalactan, albumin, collagen, polyglycolic acid, polylactic aced, glycolide-L(−) lactide poly(epsilon-caprolactone, poly(epsilon-caprolactone-CO-lactic acid), poly(epsilon-caprolactone-CO-glycolic acid), poly(β-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters such as polyglycolic acid, polylactic aced, glycolide-L(−) lactide poly(epsilon-caprolactone, poly (epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

At least one anti-MCP-1 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

10. Therapeutic Applications

The present invention also provides a method for modulating or treating at least one MCP-1 related disease, in a cell, tissue, organ, animal, or patient, as known in the art or as described herein, using at least one MCP-1 antibody of the present invention. The present invention also provides a method for modulating or treating at least one MCP-1 related disease, in a cell, tissue, organ, animal, or patient including, but not limited to, at least one of malignant disease, metabolic disease, an immune or inflammatory related disease, a cardiovascular disease, an infectious disease, or a neurologic disease.

Such conditions are selected from, but not limited to, diseases or conditions mediated by cell adhesion and/or angiogenesis. Such diseases or conditions include an immune disorder or disease, a cardiovascular disorder or disease, an infectious, malignant, and/or neurologic disorder or disease, or other known or specified MCP-1 related conditions. In particular, the antibodies are useful for the treatment of diseases that involve angiogenesis such as disease of the eye and neoplastic disease, tissue remodeling such as restenosis, and proliferation of certain cells types particularly epithelial and squamous cell carcinomas. Particular indications include use in the treatment of atherosclerosis, restenosis, cancer metastasis, rheumatoid arthritis, diabetic retinopathy and macular degeneration. The neutralizing antibodies of the invention are also useful to prevent or treat unwanted bone resorption or degradation, for example as found in osteoporosis or resulting from PTHrP overexpression by some tumors. The antibodies may also be useful in the treatment of various fibrotic diseases such as idiopathic pulmonary fibrosis, diabetic nephropathy, hepatitis, and cirrhosis.

Thus, the present invention provides a method for modulating or treating at least one MCP-1 related disease, in a cell, tissue, organ, animal, or patient, as known in the art or as described herein, using at least one MCP-1 antibody of the present invention. Particular indications are discussed below:

Pulmonary Disease

The present invention also provides a method for modulating or treating at least one malignant disease in a cell, tissue, organ, animal or patient, including, but not limited to, at least one of: pneumonia; lung abscess; occupational lung diseases caused be agents in the form or dusts, gases, or mists; asthma, bronchiolitis fibrosa obliterans, respiratory failure, hypersensitivity diseases of the lungs including hypersensitivity pneumonitis (extrinsic allergic alveolitis), allergic bronchopulmonary aspergillosis, and drug reactions; adult respiratory distress syndrome (ARDS), Goodpasture's Syndrome, chronic obstructive airway disorders (COPD), idiopathic interstitial lung diseases such as idiopathic pulmonary fibrosis and sarcoidosis, desquamative interstitial pneumonia, acute interstitial pneumonia, respiratory bronchiolitis-associated interstitial lung disease, idiopathic bronchiolitis obliterans with organizing pneumonia, lymphocytic interstitial pneumonitis, Langerhans' cell granulomatosis, idiopathic pulmonary hemosiderosis; acute bronchitis, pulmonary alveolar proteinosis, bronchiectasis, pleural disorders, atelectasis, cystic fibrosis, and tumors of the lung, and pulmonary embolism.

Malignant Disease

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodysplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, renal cell carcinoma, breast cancer, nasopharyngeal carcinoma, malignant histiocytosis, paraneoplastic syndrome/hypercalcemia of malignancy, solid tumors, adenocarcinomas, squamous cell carcinomas, sarcomas, malignant melanoma, particularly metastatic melanoma, hemangioma, metastatic disease, cancer related bone resorption, cancer related bone pain, and the like.

Immune Related Disease

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondylitis, gastric ulcer, seronegative arthropathies, osteoarthritis, inflammatory bowel disease, ulcerative colitis, systemic lupus erythematosus, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphylaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemochromatosis, alpha-1-antitrypsin deficiency, diabetic retinopathy, hashimoto's thyroiditis, osteoporosis, hypothalamic-pituitary-adrenal axis evaluation, primary billiary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, OKT3 therapy, anti-CD3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

Cardiovascular Disease

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, restenosis, diabetic arteriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneurysms, aortic dissection, inflammation of the aorta, occlusion of the abdominal aorta and its branches, peripheral vascular disorders, occlusive arterial disorders, peripheral atherosclerotic disease, thromboangiitis obliterans, functional peripheral arterial disorders, Raynaud's phenomenon and disease, acrocyanosis, erythromelalgia, venous diseases, venous thrombosis, varicose veins, arteriovenous fistula, lymphedema, lipedema, unstable angina, reperfusion injury, post pump syndrome, ischemia-reperfusion injury, and the like. Such a method can optionally comprise administering an effective amount of a composition or pharmaceutical composition comprising at least one anti-MCP-1 antibody to a cell, tissue, organ, animal or patient in need of such modulation, treatment or therapy.

Neurologic Disease

The present invention also provides a method for modulating or treating at least one neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi.system disorder); demyelinating core disorders, such as multiple sclerosis, acute transverse myelitis; and disorders of the motor unit such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, $16^{th}$ Edition, Merck & Company, Rahway, N.J. (1992).

Fibrotic Conditions

In addition to the above described conditions and diseases, the present invention also provides a method for modulating or treating fibrotic conditions of various etiologies such as liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular pehpritis, lupus nephritis); dermal fibrosis (including but not limited to scleroderma, hypertrophic and keloid scarring, burns); myelofibrosis; Neurofibromatosis; fibroma; intestinal fibrosis; and fibrotic adhesions resulting from surgical procedures.

The present invention also provides a method for modulating or treating at least one wound, trauma or tissue injury or chronic condition resulting from or related thereto, in a cell, tissue, organ, animal or patient, including, but not limited to, at least one of: bodily injury or a trauma associated with surgery including thoracic, abdominal, cranial, or oral surgery; or wherein the wound is selected from the group consisting of aseptic wounds, contused wounds, incised wounds, lacerated wounds, non-penetrating wounds, open wounds, penetrating wounds, perforating wounds, puncture wounds, septic wounds, infarctions and subcutaneous wounds; or wherein the wound is selected from the group consisting of ischemic ulcers, pressure sores, fistulae, severe bites, thermal burns and donor site wounds; or wherein the wound is anaphthous wound, a traumatic wound or a herpes associated wound. Donor site wounds are wounds which e.g. occur in connection with removal of hard tissue from one part of the body to another part of the body e.g. in connection with transplantation. The wounds resulting from such operations are very painful and an improved healing is therefore most valuable. Wound fibrosis is also amenable to anti-MCP-1 antibody therapy as the first cells to invade the wound area are neutrophils followed by monocytes which are activated by macrophages. Macrophages are believed to be essential for efficient wound healing in that they also are responsible for phagocytosis of pathogenic organisms and a clearing up of tissue debris. Furthermore, they release numerous factors involved in subsequent events of the healing process. The macrophages attract fibroblasts which start the production of collagen. Almost all tissue repair processes include the early connective tissue formation, a stimulation of this and the subsequent processes improve tissue healing, however, overproduction of connective tissue and collagen can lead to a fibrotic tissue characterized as inelastic and hypoxic. The anti-MCP-1 antibodies of the invention can be used in methods for modulating, treating or preventing such sequalae of wound healing.

The present antibodies of the present invention may also be used in methods for modulating or treating at least one symptom of chronic rejection of a transplanted organ, tissue or cell, such as a cardiac transplant.

Other Therapeutic Uses of Anti-MCP-1 Antibodies

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottis, *E. coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitis/epididimitis, *legionella*, lyme disease, influenza a, epstein-barr virus, vital-associated hemaphagocytic syndrome, vital encephalitis/aseptic meningitis, and the like.

Any method of the present invention can comprise administering an effective amount of a composition or pharmaceutical composition comprising at least one anti-MCP-1 antibody to a cell, tissue, organ, animal or patient in need of such modulation, treatment or therapy. Such a method can optionally further at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalazine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod (dexamethasone), an anabolic steroid (testosterone), a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin (rituximab), an immunosuppressive (e.g., basiliximab, cyclosporine, daclizumab), a growth hormone, a hormone antagonist, a reproductive hormone antagonist (flutamide, nilutamide), a hormone release modulator (leuprolide, goserelin), a hormone replacement drug, an estrogen receptor modulator (tamoxifen), a retinoid (tretinoin), a topoisomerase inhibitor (etoposide, irinotecan), a cytoxin (doxorubicin), a mydriatic, a cycloplegic, an alkylating agent (carboplatin), a nitrogen mustard (melphalan, chlorabucil), a nitrosourea (carmustine, estramustine) an antimetabolite (methotrexate, cytarabine, fluorouracil), a mitotic inhibitor (vincristine, taxol), a radiopharmaceutical (Iodine131-tositumomab), a radiosensitizer (misonidazole, tirapazamine) an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine (interferon alpha-2, IL2) or a cytokine antagonist (infliximab). Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Particular combinations for treatment of neoplastic diseases comprise co-administration or combination therapy by administering, before concurrently, and/or after, an antineoplastic agent such as an alkylating agent, a nitrogen mustard, a nitrosurea, an antibiotic, an anti-metabolite, a hormonal agonist or antagonist, an immunomodulator, and the like. For use in metastatic melanoma and other neoplastic diseases, a preferred combination is to co-administer the antibody with dacarbazine, interferon alpha, interleukin-2, temozolomide, cisplatin, vinblastine, Imatinib Mesylate, carmustine, paclitaxel and the like. For metastatic melanoma, dacarbazine is preferred.

11. Dosages and Methods of Administration

A method of the present invention can comprise a method for treating a MCP-1 mediated disorder, comprising administering an effective amount of a composition or pharmaceutical composition comprising at least one anti-MCP-1 antibody to a cell, tissue, organ, animal or patient in need of such modulation, treatment or therapy. Such a method can optionally further comprise co-administration or combination therapy for treating such diseases or disorders, wherein the administering of said at least one anti-MCP-1 antibody, specified portion or variant thereof, further comprises administering, before concurrently, and/or after, at least one selected from a renal drug, a dermatological drug, an anti-angiogenic drug, an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like, at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalazine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Such drugs are well known in the art, including formulations, indications, dosing and administration for each presented herein (see., e.g., Nursing 2001 Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmacotherapy Handbook, Wells et al., ed., Appleton & Lange, Stamford, Conn., each entirely incorporated herein by reference).

Typically, treatment of pathologic conditions is effected by administering an effective amount or dosage of at least one anti-MCP-1 antibody composition that total, on average, a range from at least about 0.01 to 500 milligrams of at least one anti-MCP-1 antibody per kilogram of patient per dose, and preferably from at least about 0.1 to 100 milligrams antibody/ kilogram of patient per single or multiple administration, depending upon the specific activity of contained in the composition. Alternatively, the effective serum concentration can comprise 0.1-5000 µg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques. Suitable pharmaceutical carriers are described in the most recent edition of Remington's Pharmaceutical Sciences, A. Osol, a standard reference text in this field.

Alternative Administration. Many known and developed modes of can be used according to the present invention for administering pharmaceutically effective amounts of at least one anti-MCP-1 antibody according to the present invention. While pulmonary administration is used in the following description, other modes of administration can be used according to the present invention with suitable results. MCP-1 antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration. Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or triglycerides. Parental administration is known in the art and includes, but is not limited to, conventional means of injections, a gas pressured needle-less injection device, or laser perforator devise, as well known in the art (e.g., but not limited to, materials and methods disclosed in U.S. Pat. No. 5,851,198, and U.S. Pat. No. 5,839,446, entirely incorporated herein by reference).

Alternative Delivery. The invention further relates to the administration of at least one anti-MCP-1 antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. At least one anti-MCP-1 antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration. For pulmonary administration, preferably at least one anti-MCP-1 antibody composition is delivered in a particle size effective for reaching the lower airways of the lung or sinuses. According to the invention, at least one anti-MCP-1 antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin® metered dose inhaler, typically use a propellant gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668, 218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one anti-MCP-1 antibody is delivered by a dry powder inhaler or a sprayer. There are a several desirable features of an inhalation device for administering at least one antibody of the present invention. For example, delivery by the inhalation device is advantageously reliable, reproducible, and accurate. The inhalation device can optionally deliver small dry particles, e.g. less than about 10 μm, preferably about 1-5 μm, for good respirability.

Example 1

Generation of MCP-1 Antibodies Specific for MCP-1 Using Phage Display as a Non-Limiting Example Applicants have previously shown desirable therapeutic characteristics of a murine anti-human MCP-1 antibody designated C775 and described in applicants co-pending patent application U.S. Ser. No. 11/170,453 (SEQ ID NO: 7 and 8 of that application for the heavy and light chain variable regions, respectively) and related filings. The objective of the present effort was to identify at least one human antibody from the HuCAL GOLD®, which neutralizes the biological activity of the human chemokine MCP-1 and displays similar attributes. The attributes of the C775 antibody, the thus the desired human anti-MCP-1 antibody, were defined by success criteria outlined below.

Success Criteria for at Least one Therapeutic Antibody:

Binds to human MCP-1 in solid phase format;

Specificity defined as lack of binding at 100 nM to the homologue proteins human MCP-2, 3, 4 and human Eotaxin 1, 2 and 3;

Inhibits human MCP-1 binding to its human receptor CCR2 on Thp-1 cells and the IC50 value is less than for the reference Fab C775;

Inhibits human MCP-1 mediated chemotaxis of THP-1 cells and the IC50 value is less than for the reference Fab C775;

Inhibits human MCP-1 mediated activity in a second bioassay (e.g. Ca2+ mobilization or CCL-2 induced receptor internalization) as a qualitative yes/no criterion, or with potency comparable to reference Fab C775 in a quantitative assay;

Binds to human MCP-1 with $K_d$<0.5 nM;

Binds to cynomolgus monkey MCP-1 with a $K_D$<20 nM, and preferably <10 nM;

Inhibits native human MCP-1 and chemically synthesized human MCP-1 bioactivity with comparable potencies;

Retains criteria 1-8 after reengineering of the Fab as an IgG and based on the fulllength IgG form of C775 as comparator.

Summary of the Selection Process

Ten different pannings were performed using HuCAL GOLD® and 17856 clones were screened resulting in 1104 primary hits. Finally 26 unique Fabs were identified binding synthetic human MCP-1 in ELISA. Out of those, 7 different Fabs were selected for affinity maturation according to affinity, bioactivity, specificity and binding to cynomolgus and native human MCP-1. The affinities of the parental Fabs were in the range of 10 to 400 nM and the $IC_{50}$ values in the radio-ligand binding assay were from 10 to 600 nM.

Materials and Methods

DNA restriction and modification enzymes as well as polymerases were purchased from Invitrogen (Carlsbad, Calif., USA), New England Biolabs (Beverly, Mass., USA), Roche Diagnostics (Mannheim, Germany) and MB1 Fermentas (Vilnius, Lithuania). Goat anti-human IgG F(ab')$_2$ fragment specific POD conjugated was supplied by Jacksons (West Grove, PN, USA), sheep anti-human IgG, Fd fragment specific, antibody by The Binding Site (Birmingham, UK) and streptavidin conjugated to alkaline phosphatase (ZyMAX™ grade) by Zymed Laboratories (San Francisco, Calif., USA). Recombinant human chemokines, hMCP-1, 2, 3, 4 and heotaxin 1, 2 and 3 (R&D systems) Reagents, Ligands and Antibodies: mAb 279, specific for human MCP-1 (R&D systems); synthetic hMCP-1 (Bachem); mAbl mouse anti hCCR2 biotin (R&D systems); human gamma globulin (Jackson Immuno Research); mouse gamma globulin (Jackson Immuno Research); mAb mIgG2b isotype control biotin (R&D systems); streptavidin-PE (BD Pharmingen); Versene (Invitrogen; PBS (Invitrogen). FCS (PAN); V-bottom well plates (Greiner); and U-bottom well plates (Nunc).

Preparation of MCP-1 polypeptide and analogs. Stepwise solid phase peptide synthesis and affinity purification to provide isolated, full length, mature (76 amino acid), and correctly folded and optionally modified human MCP-1 and variants with biological activity as described in applicants co-pending application U.S. Ser. No. 60/682,620 and in Kruszynski et al. 2006, J Peptide Sci. 12:25-32. The variants, designed to exhibit native surface topology and peptide backbone structure, include A40S, V41I, and F43Y. Chemical synthesis also provided a method for the site specific biotinylation of human MCP-1 using the epsilon-amino group of lysine not involved in receptor binding or surface activity at K69 and K75 is disordered in the structure (U.S. Ser. No. 60/682,620 and Kruszynski et al. 2006, J Peptide Sci. 12:354-360). A hydrophilic spacer of four ethyleneoxy units (PEG$_4$) was inserted between the biotin and the $\epsilon$-amino group of lysine residue. The chain length from biotin amide to terminal carbonyl is 19.2 Å. The spacer was chosen to increase solubility and provide sufficient spacer length for binding streptavidin conjugates. The sequence of MCP-1 and variants is given in SEQ ID NO: 1. Variants were determined to retain the ability to induce Ca2+ mobilization in THP-1 cells. Biotin-Lys$^{69}$ and biotin-Lys$^{75}$ MCP-1 were compared side by side in screening, consolidation and affinity determination and no significant differences could be observed. Using Biacore, 35 optimized Fabs were analyzed on MCP-1 Ile$^{41}$, Lys(biotin-PEG$_4$)$^{69}$ and MCP-1 Ile$^{41}$, Lys(biotin-PEG$_4$)$^{75}$ immobilized on streptavidin chips in parallel. In general the measured affinities on MCP-1 K69 and K75 were comparable.

Phage Fab Library. The phagemid library is based on the HuCAL® concept (Knappik et al., 2000) and employs the CysDisplay™ technology for displaying the Fab on the phage surface (Löhning, 2001). The library encodes approximately 10$^{10}$ unique Fabs displayed on M13 bacteriophage as fusions to a minor coat protein, pIII. For the selections HuCAL GOLD® antibody-phages were divided into three pools comprising different VH master genes. In addition the whole library was used in one pool (VH1-6). 2×10$^{13}$ HuCAL GOLD input phages were used for each panning. 4 different panning strategies were applied, including 3 panning rounds on human MCP-1 analog-1 (V41I, Ile$^{41}$) and analog-2 (F43Y, Tyr$^{43}$) respectively, and two alternating pannings on the analogs in the order 1-2-1 and 2-1-2.

Solid phase panning. A 100 µl aliquot of human MCP-1 analog-1 (V41I) or analog-2 (F43Y) at 50 µg/ml in PBS, pH 7.4, were directly coated on Maxisorp® wells (Nalgen Nunc, Rochester, N.Y.) overnight at 4° C. The coated wells were washed and blocked with 5% MPBS (PBS, 5% low fat milk powder). 100 µl blocked HuCAL GOLD® phages per well were added for 2 h at RT. After several washing steps, bound phages were eluted by 100 µl 20 mM DTT in 10 mM Tris/HCl, pH 8.0 incubated at RT for 10 min. The eluate was used to infect mid-phase E. coli TG1 (Stratagene, Amsterdam, The Netherlands) and phagemids were amplified as described (Krebs et al., 2001).

Semi-Solution Panning Against Human MCP-1 Analog-1 (V41I) and Analog-2 (F43Y) Resulting in Neutralizing Fab Molecules. A semi-solution panning was performed by incubating two biotinylated human MCP-1 derivatives, V41I, K69-PEG-biotin or V41I, K75-PEG-biotin (SEQ ID NO: 1) with the HuCAL GOLD® phages in solution followed by capturing of the phage antigen complexes to Reacti-Bind Neutravidin Coated Polystyrene microtiter plate strips (PERBIO). For the panning 1.5 ml Eppendorf tubes were blocked with Chemiblocker (Chemicon International) 1:1 diluted with PBS O/N at 4° C. The next day Reacti-Bind™ NeutrAvidin™ (Pierce, Rockford, Ill., USA) microtiter plate strips (binding capacity: 25 pmoles biotin/well; PERBIO) were rinsed with 2×300 µl PBS, needed for 2 pre-adsorption steps to reduce the number of neutravidin binders. 2×10$^{13}$ phages from the HuCAL GOLD® library in 100 µl 50% Chemiblocker (Chemicon), 0.05% TWEEN 20® (Sigma) were added per well and blocked for 1 h at RT shaking gently. For the second pre-adsorption step the phage solution was transferred to new Reacti-Bind Neutravidin Coated Polystyrene microtiter plate strips and incubated for 1 h at RT shaking gently. Then the pre-adsorbed phages and the biotinylated antigens (3:1 biotin to antigen ratio for biotinylation; 200 nM final conc.) were added to the pre-blocked 1.5 ml Eppendorf tubes and incubated for 1 h at RT on a rotating wheel. In parallel, further Reacti-Bind Neutravidin Coated Polystyrene microtiter plate strips were rinsed with 2×300 µl PBS, blocked with 300 µl Chemiblocker 1:1 diluted with PBS for 1 h and washed 1×300 µl PBS. 100 µl/well of the Biotin-antigen-phage complex were pipetted into the microtiter plate strips and incubate for 1 h at RT shaking gently. After several washing steps, bound phages were eluted by 110 µl 20 mM DTT in 10 mM Tris/HCl, pH 8.0, incubated at RT for 10 min. The eluate was used to infect mid-phase E. coli TG1 (Stratagene, Amsterdam, The Netherlands) and phagemids were amplified as described (Krebs et al., 2001).

Subcloning and Microexpression of Selected Fab Fragments. To facilitate rapid expression of soluble Fab, the Fab encoding inserts of the selected HuCAL GOLD® phages were subcloned via XbaI and EcoRT into the expression vector pMORPH®X9_FH. Fab fragments carry a C-terminal FLAG™ tag (Prickett et al., 1989) and as a second C-terminal tag the 6×His-tag (Chen et al., 1994). After transformation of TG1-F⁻ single clone expression and preparation of periplasmic extracts containing HuCAL®-Fab fragments were performed as described previously (Rauchenberger et al., 2003).

Solid phase format binding assay on human MCP-1 analog-1 (V41I) was performed as described above. After blocking, periplasmic extracts were added. Detection of the Fab-fragments was performed by incubation with goat anti-human IgG, F(ab')$_2$ fragment specific antibody.

Screening on immobilized, biotinylated hMCP-1 V41I was performed using Reacti-Bind™ NeutrAvidin™ 384 well plates (Pierce, Rockford, Ill., USA) coated with 20 µl 0.5 µl/ml biotinylated hMCP-1 analog-1 (V41I) or analog-2 (F43Y) diluted in PBS, pH 7.4, for 16 h at 4° C. After blocking with 1% BSA in TBS, 0.05% TWEEN 20® (Sigma, St. Louis, Mo., USA) for 1 h at RT, periplasmic extracts were added. Detection of the Fab-fragments was performed by incubation with goat anti-human IgG, F(ab')$_2$ fragment specific antibody.

Solution phase screening with biotinylated hMCP-1 Analog-1 (V41I) was performed by coating Maxisorp (Nunc, Rochester, N.Y., USA) 384 well plates with 20 µl sheep anti-human IgG, Fd fragment specific, antibody diluted 1:1000 in PBS, pH 7.4 for 16 h at 4° C. After blocking with 3% BSA in TBS, 0.05% TWEEN 20® (Sigma, St. Louis, Mo., USA) for 2 h at RT, periplasmic extracts were added. Subsequently the captured HuCAL®-Fab fragments were allowed to bind to 0.2 µg/ml biotinylated hMCP-1 analog-1 (V41I) in TBS, which was detected by incubation with streptavidin conjugated to alkaline phosphatase followed by addition of AttoPhos fluorescence substrate (Roche Diagnostics, Mannheim, Germany). Fluorescence emission at 535 nm was recorded with excitation at 430 nm.

Bioactivity Assays

Cell culture. All cells were cultured under standardized conditions at 37° C. and 5% $CO_2$ in a humidified incubator. Cells expressing CCR2 were grown in standard medium. In addition THP-1 cells (human acute monocytic leukemia cells) were cultivated in RPMI containing 2 mM L-glutamine, 1.5 g/L sodium bicarbonate, 4.5 g/L glucose, 10 mM HEPES and 1.0 mM sodium pyruvate, 90%; 10% fetal bovine serum (FBS; Vitacell RPMI 20-2001, ATCC, Manassas, Va.) at 37° C. and 5% $CO_2$ at a density of $4-8 \times 10^5$ cells/mL.

Radioligand Binding Assay. Competition assays were performed in Millipore filter plates (Millipore, Bedford, Mass.). $1 \times 10^6$ THP-1 cells/well were incubated with $^{125}$I-MCP-1 (1 ng/mL; Perkin Elmer Life Science, Boston, Mass.) together with different concentrations of recombinant human (rh) MCP-1 (279-MC, R&D Systems, Minneapolis, Minn.) or synthetic proteins. All reagents were diluted in binding buffer consisting of RPMI Medium 1640 (Invitrogen Corp., Grand Island, N.Y.) and 0.1% BSA. The competition was allowed to proceed for 1 h at RT and the wells were washed 3 times with 150 µL/well wash buffer (binding buffer+1 M NaCl). The radioactivity on the filters were counted using the Wallac Wizard 1470 Automatic Gamma Counter (Perkin Elmer Life Sciences Inc., Boston, Mass.). Percent inhibitions of the binding of $^{125}$I-MCP-1 to CCR2 by the varying doses of either recombinant or synthetic MCP-1 were calculated. The percent inhibition values were then imported into the Graphpad Prism program and plotted using a sigmoid dose-response curve with a variable slope and constants of bottom=0 and top=100.

Calcium Mobilization Assay. The $Ca^{2+}$ mobilization assay was performed in a 96-well format, using the FLEXstation™ $Ca^{2+}$ Plus Assay Kit (Molecular Devices, Sunnyvale, Calif.) following the manufacturer's protocol for non-adherent cells and a FLEXstation™ (Molecular Devices, Sunnyvale, Calif.). The peak RFU values were imported into Graphpad Prism program for analysis. MCP-1 Induced CCR2 Receptor Internalization FACS Assay. After optimization of ligand concentration (EC50 of synthetic MCP-1~100 ng/ml) and incubation time (after 1 h most internalization had occurred) the IC50 was determinated by adding different concentrations of antibodies. Cultured CCR2 expressing cells were washed with PBS and detached with Versene (Invitrogen) for about 10 min at 37° C. All centrifugation steps of the cells were at about 200×g. Cells were washed twice with FACS buffer (PBS/3% FCS), counted and checked for viability (trypan blue). 96 V-bottom well plates (Greiner) were filled with $\sim 2.5 \times 10^5$ cells in 100 µl per well and put on ice. In a 96 U-bottom well plate (Nunc) the antibodies were diluted in cell culture medium (MEME) to give about 200 µg/ml down to 0.001 µg/ml in triplicate samples. The different concentrations of the antibodies were pre-incubate with a final concentration of 100 ng/ml synthetic MCP-1 (Bachem) for 10 min at RT. The cells were re-suspended with the pre-incubated 100 µl MCP-1/antibody mixture and incubated for 1 h at 37° C. in an incubator for receptor internalization. After internalization cells were washed once with 180 µl cold FACS buffer and the plates have to be kept on ice for all subsequent steps to prevent further internalization. Biotinylated mouse anti-hCCR2 mAb (R&D Systems) was diluted 1:10 in FACS buffer. As control mouse IgG2b Isotype Biotin mAb (R&D Systems) was also diluted 1:10 in FACS buffer. 10 µg/ml final concentration of a 1:1 mix of human and mouse gamma globulin (Jackson Immuno Research) were added to both anti-hCCR2 and control mAb to block Fc-receptors. Cells were re-suspended in 50 µl anti-CCR2/gamma globulin mix (or control IgG2b/gamma globulin mix) and incubated for 1 h on ice. Cells were washed twice with 180 µl FACS buffer, re-suspended in 50 µl 1:400 diluted Streptavidin-PE (BD Pharmingen) and incubated for 1 h at 4° C. on ice in the dark. Cells were washed twice with 180 µl FACS buffer, re-suspended in 100 µl 2% PFA/PBS and stored overnight at 4° C. for fixation (alternatively direct measurement without PFA fixation is possible). For FACS measurement the cells were re-suspended with 200 µl FACS buffer and at least 5000 cells were counted each.

Affinity Assays

Solution Equilibrium Titration (SET) Method for $K_D$ Determination and Cross-Reactivity Studies Using BioVeris. Affinity determination in solution was basically performed as described in the literature (Friguet et al., 1985). In order to improve the sensitivity and accuracy of the SET method, it was transferred from classical ELISA to ECL based BioVeris technology (Haenel et al., 2005, accepted for publication in *Analytical Biochemistry*). 1 mg/ml goat-anti-human (Fab)$_2$ or goat-anti-mouse IgG, Fc fragment specific antibodies (Jackson Immuno Research) were labelled with BV-tag™ NHS-Ester (Bioveris Europe, Witney, Oxfordshire, UK) according to manufacturer's instructions. The experiments were carried out in polypropylene microtiter plates and PBS pH 7.4 with 0.5% BSA and 0.02% TWEEN 20® as assay buffer. Unlabeled antigen was diluted in 4″ series: For human and cyno MCP-1 a concentration range of 10 pM to 40 nM and for cross-reactivity controls (Eotaxin and MCP-2) a concentration range of 40 pM to 160 nM was chosen. Wells without antigen were used to determine Smax values. After addition of 100 pM Fab or IgG (final concentration in 75 µL final volume), the mixture was incubated for 2 hours at RT. Subsequently a mixture of 25 µl Dynabeads (0.4 mg/ml M-280 Streptavidin, DYNAL, Hamburg), coated with 0.25 µg/ml biotinylated MCP-1 (K69) and BV-tag labeled detection antibody in a final dilution of 1:4000 for anti-human Fab or 1:2000 for anti-mouse IgG were added per well. After incubation for 30 min on an Eppendorf shaker (700 rpm) at RT, electrochemiluminescence signals were detected using a M-384 SERIES® Workstation (Bioveris Europe) Data were evaluated with Origin 5.0 (Microcal) software applying customized fitting models (for Fab: Haenel et al., 2005, accepted for publication in *Analytical Biochemistry*; for IgG: according to Piehler et al., 1997).

Biacore $K_D$ Determination on Directly Coated Antigen. The kinetic constants $k_{on}$ and $k_{off}$ were determined with serial dilutions of the respective Fab binding to covalently immobilized MCP-1 using the BIAcore 3000 instrument (Biacore, Uppsala, Sweden). For covalent antigen immobilization standard EDC-NHS amine coupling chemistry was used. Kinetic measurements were done in PBS (136 mM NaCl, 2.7 mM KCl, 10 mM $Na_2HPO_4$, 1.76 mM $KH_2PO_4$ pH 7.4) at a flow rate of 20 µl/min using Fab concentration range from 1.5-500 nM. Injection time for each concentration was 1 min, followed by 3 min dissociation phase. For regeneration 5 µl 10 mM HCl was used. All sensograms were fitted using BIA evaluation software 3.1 (Biacore). Biacore $K_D$ Determination on Biotin-K69 Human MCP-1 and Cyno MCP-1. Biotin-K69 human MCP-1 and biotinylated cyno MCP-1 were coated to streptavidin chip surface and cyno-MCP-1 was directly coated to CM5 chips. Binding of the Fabs was tested using the standard methods.

Biacore $K_D$ Determination in the Antibody Capture Mode. Fabs were captured at 500 nM with anti-hFab (s.3.15) on a CM5 chip (flow-rate 5 µl/min), solution of each analog (MCP1, 2, 3, 4 and Eotaxin, Eotaxin-2 and -3) was injected. All cytokines were carrier free and used in a concentration range from 15 to 500 nM (for parental Fabs before optimization) as an analyte for Affinity determination. Sensorgrams were analyzed using the BIAevaluation software. Biacore affinity determination to MCP-1 in the antibody capture mode was not possible for the optimized binders because the detection limits of Biacore were reached.

For the specificity analysis of Fabs, surface plasmone resonance was used (Biacore 3000, Uppsala, Sweden) using the capture assay was used. Fabs were captured and the various proteins (MCP-2, -3, -4 and Eotaxin-1, -2 and -3) were used as analytes. CM5 chips (Biacore, Sweden) were coated with 6500-8000 RU anti-$F(ab)_2$ (Dianova, Affipure $F(ab)_2$ fragment goat anti-human IgG, $F(ab)_2$ fragment specific; 10 mM acetate buffer, pH 4.5) on all 4 flow cells, using standard EDC-NHS amine coupling chemistry. The flow cells 2-4 were captured with specific anti-MCP-1 Fabs (20 µl of 500 nM Fab at a flow rate of 10 µl/ml, resulted capture density 300-400RU). After capturing of Fabs, the chemokines were injected (20 µl, flow rate 20 µl/min, PBS pH 7.4) at a concentration of 100 nM. Chemokines were stored in small aliquots and only freshly thawed material with maximum 1 freeze thaw cycle was used for the measurements. To avoid a combination of off rates aroused by the off rate of MCP-1, Fab specific interaction and the anti-Fab/Fab interaction, buffer was injected, to determine the dissociation of anti-Fab/Fab interaction. The achieved buffer sensorgram was subtracted from the specific one. The response units were normalized to the amount of capture antibody onto the surface.

Binding to Native MCP-1 in the Antibody Capture Mode. The method was used as described above. Native MCP-1 was purified from the PANC1 supernatant and used for binding analysis. Binding to native MCP-1 in the Fab capture mode was well above the detection limit, however, a true affinity measurement was not possible owing to the impurities in the extract obscuring the correct concentration of the native MCP-1.

Conversion to IgG

In order to express full length IgG, variable domain fragments of heavy (VH) and light chains (VL) were subcloned from Fab expression vectors into appropriate pMorph_hIg vectors for human IgG1, human IgG4, chimeric human/mouse IgG1 and IgG2a. Restriction enzymes EcoRI, MfeI, BlpI were used for subcloning of the VH domain fragment into pMorph_hIgG1.1, pMorph_hIgG4.1, pMorph_mIgG1.1 or pMorph_mIgG2a.1 and EcoRV, BsiWI for subcloning of the VL domain fragment into pMorph_hIgκ_1, pMorph_hIgλ_1, pMorph_mIgκ_1 or pMorph_mIgλ_1 vectors respectively. Resulting IgG constructs were expressed at CNTO.

Results

Solid phase panning was performed on hMCP-1 (41I) and hMCP-1 (43Y) directly coated to Maxisorp plates. Four different panning strategies were applied, containing three selection rounds each. After sub-cloning into the expression vector pMORPHx9_Fab_FH the solid phase screening was performed on directly coated hMCP-1 (41I) and on biotinylated hMCP-1. In total 8832 clones were analyzed in primary screening and 983 primary hits were obtained. Finally 5 unique Fabs were identified, but all 5 Fabs did not neutralize MCP-1 in cellular assays, indicating that direct coating to Maxisorp might impair the conformation or at least the accessibility of neutralizing epitopes.

A semi-solution panning was performed incubating the biotinylated human MCP-1 analog-1 (V41I) and analog-2 (F43Y) with the HuCAL GOLD® phages in solution followed by capturing of the phage antigen complexes as described. Two different main panning strategies were applied including 3 rounds of panning on biotinylated human MCP-1 protein analog-1 (V41I) and analog-2 (F43Y) respectively (no alternating panning). In total 9024 clones were analyzed in primary screening and 121 primary hits were obtained, finally revealing 18 unique binders. A Luminex based re-screening of 192 clones from panning on biotinylated human MCP-1 protein analog-1 (V41I) lead to 9 additional primary hits and 3 additional unique binders, showing that Luminex screening is a suitable alternative screening method to the capture screening. In total 21 unique binders were identified from the semi-solution panning and 14 of these binders showed neutralizing activity. All neutralizing Fabs from HuCAL GOLD® derived from this panning.

Characterization of HuCAL GOLD® Fabs. Unique Fabs were expressed and purified for further characterization. hMCP-1 binding affinity was determined by BIAcore and Fabs were characterized in the following assays: 1) inhibition of binding of $^{125}$I-CCL-2 to Thp-1 cells and 2) inhibition of hMCP-2 induced Ca2+ mobilization in Thp-1 cells. Fabs that demonstrated neutralization activity in the cell based assays were further tested for 1) binding to synthetic cynomolgous hMCP-2; 2) binding to hMCP-2 family related human chemokines for binding specificity (i.e. MCP-2, 3, 4 and Eotaxin 1, 2, 3); and 3) binding to native human hMCP-2 to ensure the Fabs selected using the synthetic hMCP-2 peptide, recognize native hMCP-2. Seven Fabs with the most optimal properties were chosen for additional affinity maturation. Properties of the Fabs selected for affinity maturation were summarized in Table 2. The seven Fabs were selected for affinity maturation were assigned to 3 groups for the library cloning and the selection. L-CDR3 and H-CDR2 optimization was performed in parallel. The parallel optimization of the light and the heavy variable chains created the potential for combining improved heavy and light chain via cross cloning to generate even further improved antibodies.

TABLE 2

A summary of Fab candidates selected for affinity maturation.

| Fab Designation | Group | Kd MCP-1 (nM) | Radioligand Binding IC$_{50}$ (nM) | Ca2+ mobilization IC$_{50}$ (nM) | Specificity | Kd Cyno [nM] | Native MCP-1 binding | Sequence group Hc Lc |
|---|---|---|---|---|---|---|---|---|
| MOR 03336 | 1 | 60 ± 33 | 114 | 526 | MCP-1 | 170 ± 42 | yes | VH3/VL-λ3 |
| MOR 03464 | 1 | 75 +/− 50 | 105 | 1340 | MCP-1, 2 | 175 ± 49 | yes | VH3/VL-λ3 |
| MOR 03468 | 1 | ND | 255 | 2000 | MCP-1 | 550 ± 14 | ND | VH1B/VL-λ3 |
| MOR 03470 | 1 | 46 +/− 1 | 645 | 2100 | MCP1 | 145 ± 92 | yes | VH1B/VL-λ3 |
| MOR 03471 | 2 | 94 +/− 6 | 180 | 1256 | MCP-1 | 465 ± 106 | yes | VH1A/VL-κ3 |
| MOR 03473 | 2 | 175 +/− 20 | 184 | 2900 | MCP-1 | 478 ± 95 | yes | VH1A/VL-κ3 |
| MOR 03548 | 3 | 42 | 11 | 124 | MCP-1, Eo | 54 ± 8 | yes | VH3/VL-λ3 |

Example 2

Evaluation of High Affinity, MCP-1 Specific Antibodies from Fabs

As noted, the selection of candidates for the affinity maturation was performed on candidates in the free Fab format. Selection criteria were: activity in radio-ligand binding assay, activity in Ca2+ mobilization assay, affinity to human MCP-1 measured by Biacore, specificity to human MCP-1, affinity to cyno MCP-1 and binding to native MCP-1 detected in Biacore. Additional criteria for grouping the parental Fabs were C775 competition in ELISA and were based on the framework family of the variable heavy and light chain. Characterization of maturation candidates as IgG, especially in chemotaxis assay, was performed in parallel with the maturation selection process.

The seven Fabs selected for maturation fell into 3 different sequence classes. In one class (Group 1, Table 2), Fabs 03336, 03464, 03468 and 03470 had Vλ3 light chain frameworks with one of two different heavy chain frameworks. Fabs 03336 and 03464 had VH3 heavy chain frameworks and Fabs 03468 and 03470 had VH1B heavy chain frameworks. The second class of Fabs (Group 2, Table 2), 03471 and 03473, had VH1A heavy chain frameworks and Vκ3 light chain frameworks. Fab 03548 had the same the heavy and the light chain frameworks as two of the Fabs in the first class (VH3, Vλ3) but was maintained separately (Group 3, Table 2) because it had exceptionally potent biological activity and binding cross reactivity with Eotaxin. For a complete description of the variable region sequence classification used here see U.S. Pat. No. 6,828,422, entirely incorporated by reference. The goal of the latter maturation was to improve affinity of 03548 for CCL-2 while increasing specificity.

Before maturation, only binding to but not affinity to cynomolgus and native human MCP-1 was determined in Biacore Fab capture mode. All 7 parental Fabs showed binding to both, cyno- and native-MCP-1, which was a pre-requisite for maturation.

Binding Specificity of the Parental IgGs. After conversion of all 7 parental Fabs to IgG1, The cross-reactivity studies were repeated for IgG forms. Eotaxin3 bound non-specifically to dextran surface on the sensor chips and this non-specific binding could be competed away by adding carboxyl methyl dextran. As non-specific binding to the dextran surface of other chemokines was also possible, carboxyl methyl dextran was added in all Biacore specificity assays. In contrast to the Fabs, two of the IgGs showed no significant binding to human MCP-1, interestingly all 4 final binders that fulfilled all success criteria came from one parental Fab.

The binding signal of MCP-1 (response units) were normalized by the amount of capture antibody on the surface:

Molar binding ratio=(RU of antigen bound/MW of antigen)×(MW of mAb/RU of mAb captured onto the surface) and molar binding ratio lower than 0.5 was expected to be not significant. Four of the IgGs showed normalized binding ratio to MCP-1>0.5 and to all homologue chemokines <0.5 and were therefore termed specific on the level of IgG. One IgG also showed some binding to MCP-2 and Eotaxin, which was already detected on the level of Fab, but this cross-reactivity was reduced on the level of IgG. Data of MOR03468 IgG are not shown.

Inhibition of I$^{125}$ MCP-1 Binding to THP-1 Cells (CNTO). Neutralizing activity of the parental binders in the IgG1 format was first tested in the radio-ligand binding assay. After blocking of the Fc receptors on the THP-1 cells by addition of unrelated human IgG1, inhibition of MCP-1 binding was detectable for all parental IgGs. Four IgGs showed inhibition of radio-labeled human MCP-1 to THP-1 cells with IC$_{50}$ values in the range of the reference IgG C775.

Inhibition of Calcium Mobilization (CNTO). All parental IgGs inhibited MCP-1 induced calcium mobilization in THP-1 cells. Four IgGs showed inhibition of MCP-1 induced calcium mobilization at higher antibody concentration compared to the reference IgG C775.

Inhibition of MCP-1 Induced Chemotaxis (CNTO). As the parental Fabs could not be tested in the chemotaxis assay, inhibition of MCP-1 induced chemotaxis was tested in the IgG format. All parental IgGs tested were active in the chemotaxis assay, and four IgGs showed inhibition of MCP-1 induced chemotaxis at higher antibody concentrations compared to the reference IgG C775.

Example 3

Affinity Maturation of Selected Fab by Parallel Exchange of L-CDR3/H-CDR2 Cassettes Summary of Affinity Maturation Process In the first maturation round L-CDR3 optimization and H-CDR2 optimization were performed in parallel. DNA from each class of Fabs was pooled for maturation library construction. The original heavy chain CDR2 and light chain CDR3 sequences were replaced by randomized sequences for each DNA pool resulting in 6 new libraries: 3 randomized H-CDR2 and 3 randomized L-CDR3 libraries. The diversity of the each of the 6 libraries was greater than 108 unique Fabs. The synthetic CCL-2 41I-biotin-K69 peptide was used either for solution panning or panning of the biotin-peptide captured on neutravidin coated plastic wells. Each of the 6 libraries were panned under various conditions to enrich for Fabs with slow off-rates (i.e. prolonged washing, reduced antigen concentration). 36 parallel pannings were performed including solution and semi-solution panning. Reduction of antigen concentration, off-rate selection and prolonged washing resulted in stringent panning conditions. The affinity screening was performed with the help of the BioVeris (formerly IGEN) electro-chemiluminescence (ECL) based platform, allowing high throughput affinity ranking and identification of Fab molecules with improved affinity.

Libraries for Affinity Maturation As the heavy chain H-CDR2 libraries of H1A and H1B were cloned separately, 7 different variable region libraries were cloned. The two H1A and H1B libraries were later pooled prior to the selection, giving 6 selection libraries. library sizes ranged from $10^8$ to $8 \times 10^9$. All theoretical diversity was covered for all libraries except the MOR03548 λ3 L-CDR3 library, where still 0.625× of the theoretical diversity was covered. The quality control of the libraries was performed by sequencing of randomly picked clones. 71 out of 75 (95%) of the sequences were correct and diverse, while for 4 out of 75 sequences frame shifts were detected. Derivatives of all parent Fabs were found in their respective libraries.

To increase affinity and biological activity of selected antibody fragments, L-CDR3 and H-CDR2 regions were optimized in parallel by cassette mutagenesis using trinucleotide directed mutagenesis (Virnekäs et al, 1994), while the framework regions were kept constant. Prior to cloning for affinity maturation, all parental Fab fragments were transferred from the corresponding expression vector (pMORPH® X9_FH) into the CysDisplay™ vector pMORPH™ 25_LHC via XbaI/EcoRI. pMORPH® 25_LHC was created from the HuCAL GOLD® display vector pMORPH® 23_LHC by removal of one BssHII site interfering with library cloning for H-CDR2 optimization. For optimizing L-CDR3 of a pool of parental Fab fragments the L-CDR3, framework 4 and the constant region of the light chains (405 bp) of the binder pool were removed by BpI/SphI and replaced by a repertoire of diversified L-CDR3s together with framework 4 and the constant domain. Design, synthesis and cloning of this L-CDR3 cassette will be described elsewhere (manuscript in preparation). 5 μg of the binder pool vector were ligated with a 3 fold molar excess of the insert fragment carrying the diversified L-CDR3s. In a second library set the H-CDR2 (XhoI/BssHII) was diversified, while the connecting framework regions were kept constant. In order to monitor the cloning efficiency the parental H-CDR2 was replaced by a dummy, before the diversified H-CDR2 cassette was cloned in. Ligation mixtures of 7 different libraries were electroporated in 4 ml E. coli TOP10F cells (Invitrogen, Carlsbad, Calif., USA) yielding from $1 \times 10^8$ to $8 \times 10^9$ independent colonies. This library size ensured coverage of the theoretical diversity. Amplification of the library was performed as described before (Rauchenberger et al., 2003). For quality control single clones were randomly picked and sequenced (SequiServe, Vaterstetten, Germany).

Semi-Solution Panning Against Human Biotin-K69 MCP-1 (V41I) for Affinity Maturation. $1 \times 10^{13}$ phages rescued from the optimization libraries were pre-adsorbed twice on Reacti-Bind Neutravidin Coated Polystyrene microtiter plate strips and then blocked with ChemiBLOCKER (Chemicon, Temecula, Calif., USA). The pre-adsorbed phages and different concentrations of biotin-K69 MCP-1 (0.02-50 nM) were incubated for 1.5 h at 22° C. in solution, followed by capturing of the phage-antigen complexes to Reacti-Bind Neutravidin Coated Polystyrene microtiter plate strips (PER-BIO). Washing steps at 22° C. were extended up to 12 h. Elution by 20 mM DTT in 10 mM Tris/HCl, pH 8.0, and phagemid amplification between each panning round were conducted as described above.

Solution Panning Against Human Biotin-K69 MCP-1 (V41I) for Affinity Maturation. $1 \times 10^{13}$ phages, rescued from the affinity maturation library as described above, were blocked with ChemiBLOCKER (Chemicon, Temecula, Calif., USA), 0.05% TWEEN 20® (Sigma, St. Louis, Mo., USA) and pre-adsorbed twice on Dynabeads® M-280 Streptavidin (Dynal Biotech, Oslo, Norway) blocked by ChemiBLOCKER without TWEEN 20®. Reduction of antigen was applied during the three panning rounds and the concentration of biotin-K69 MCP-1 ranged from 0.01 up to 5 nM. Blocked Dynabeads® and a magnetic particle separator, MPC-E (Dynal Biotech, Oslo, Norway), were used to capture phages bound to the biotinylated antigen. Washing steps (Rauchenberger et al., 2003), elution by 20 mM DTT in 10 mM Tris/HCl, pH 8.0, and phagemid amplification between each panning round were conducted as described above. In addition the panning stringency was further increased by off-rate selection (Hawkins et al., 1992) and by extended washing steps (up to 6 h).

3312 clones were screened and 85 optimized Fabs coming from 4 of 7 parental Fabs were identified. Fabs optimized in both, L-CDR3 and H-CDR2, were identified and cross-cloning of improved light and heavy chains was performed for derivatives of 2 different parental clones leading to a further improvement in affinity ($K_D$) of up to 100-fold. The top ranked binders (about 100) with a Kd estimated at ~1-10 nM were sequenced leading to the identification of 41 unique improved Fabs. Most of the improved binders were derived from Group III (03548). An additional screen was performed in Groups I and II to identify more improved Fabs in these maturation groups. Twenty nine additional class I and II binders were identified. Overall, 87 unique Fabs deriving from five of the seven parental Fabs were identified in the maturation process. Table 3 summarizes the maturation panning results.

TABLE 3

Summary of the selection of Fab with improved binding to MCP-1.

| Group | Parental Clone | L-CDR3 Improved | H-CDR2 Improved |
|---|---|---|---|
| 1 | 03336 | — | 14 |
| 1 | 03470 | — | 2 |
| 1 | 03464 | — | 1 |
| 1 | 03468 | — | — |
| 2 | 03471 | 23 | 1 |
| 2 | 03473 | — | — |
| 3 | 03548 | 11 | 35 |
| | Total improved Fabs | 34 | 63 | 87 |

Amino acid changes in the matured Fabs were located in either the H-CDR2 or the L-CDR3 of the parental clones 03741 and 03548. Cross cloning of the best improved heavy chain CDR2 with the best light chain CDR3 of the Fabs was then carried out to try to generate Fabs with even higher affinity. Approximately 36 cross-clones were generated. All unique Fab sequences were also screened for prediction of N-linked glycosylation sites. A few Fabs were identified with the NIS consensus sequence for glycosylation in heavy chain CDR2. These Fabs were excluded from further characterization. A total of 84 Fabs were expressed and purified at Morphosys and transferred to Centocor for biological characterization.

The limit of sensitivity for affinity measurement using Biacore was reached with the optimized Fabs. Therefore affinity values were determined by ECL based solution equilibrium titration (SET) (Haenel et al., 2004, submitted for publication in *Analytical Biochemistry*). After affinity maturation, a $K_D$ of about 10 pM was achieved and the value confirmed using KinexA. Fab binding in radio-ligand assay achieved an $IC_{50}$ of 110 pM. Thus, both MCP-1 affinity and binding kinetics improved up to 1000-fold compared to the parental Fabs. Four optimized Fabs fulfilled all 9 of the success criteria. Two were L-CDR3 optimized Fabs and two were cross-clones composed of L-CDR3 and H-CDR2 optimized chains. All 4 were converted to IgG1 and retained activity in all tested assays with best $K_D$ of 10 pM and best $IC_{50}$ of 20 pM in radio-ligand binding assay. One additional cross-clone MOR03899 fulfilled all success criteria as an IgG1 but not as Fab. All binders fulfilling the success-criteria were derived from MOR03471 parental Fab (SEQ ID Nos. 2, 4). The unique Fab, MOR03790, was chosen for IgG production, scale-up manufacturing development, and in vivo evaluation in animal models based on MOR03471 and comprising heavy and light chain variable regions sequences given in Table 4D and SEQ ID Nos. 6, 7, 9, 13, 14, and 16.

BioVeris Screening During Affinity Maturation. Affinity improved Fab clones were identified by a ECL based high throughput affinity screening BioVeris assay. After hit selection 4 sub-clones were consolidated by the same method.

Panning Strategies for Affinity Maturation. In total 36 different pannings were performed. 18 solution pannings against biotin-K69 MCP-1 (V41I) with capture of phage-antigen complexes to Streptavidin beads. Stringency during selection process was increased by reduction of antigen concentration, off-rate selection and prolonged washing. In addition 18 semi-solution pannings against biotin-K69 MCP-1 were executed, capturing phage-antigen complexes to Neutravidin plates. In these pannings the stringency was increased by reduction of antigen and long washing.

BioVeris Screening for Affinity Maturation. The antigen biotin-K69 MCP-1 41I was used in maturation panning and also for the BioVeris based screening. Screening worked very efficiently for identification of improved binders. For each of the 36 panning conditions 92 clones were screened, resulting in 3312 screened clones. In total, 85 different unique optimized binders were identified. Optimized Fabs from all 3 groups were found. In addition, Fabs optimized in L-CDR3 and H-CDR2 could be identified, making cross-cloning possible for Fabs designated MOR03471 and MOR03548 derivatives. 46 optimized Fabs derived from MOR03548, 35 of the Fabs came from the H-CRD2 optimization showing higher affinity and activity compared to the 11 L-CDR3 optimized Fabs. But also parental MOR03471 was very successfully optimized in this maturation with 23 Fabs optimized in L-CDR3 and one optimized in H-CDR2. Improved Fabs derived from 4 put of 7 parental Fabs, indicating that each parental binder had different potential for being optimized. Finally 4 Fabs fulfilling all success criteria derived from MOR03471, two optimized in L-CDR3 only and two from cross-cloning, optimized in L-CDR3 and H-CDR2.

Cross-Cloning of Optimized Fab molecules. The modular structure of HuCAL® technology allows rapid cross-cloning of optimized light and heavy chains of optimized Fabs derived from the same parental clone, simply by combining the two optimized chains in a cloning step. Cross-cloning is a fast method with the potential to get further improved antibodies without an additional maturation round. On the one hand 2 L-CDR3 optimized MOR03548 derivatives were cross-cloned with 6H-CDR2 optimized MOR03548 leading to 12 cross-clones. On the other hand 22 L-CDR3 optimized MOR03471 were cross-cloned with the one available H-CDR2 optimized MOR03471 clone. In this project the cross-cloning was successful leading to two different MOR03471 derived cross-clones, MOR03850 and MOR03878, which finally met all the success criteria.

Detailed Characterization of 16 Pre-Selected Antibodies 85 optimized Fabs identified from affinity screening and additional 34 cross-clones (see above) resulted in a total of 119 different unique optimized Fabs, which were not all characterized by all available assays. Therefore, the 16 optimized Fabs were pre-selected according to their $IC_{50}$ in radio ligand binding inhibition, the activity in the calcium release assay, the lack of N-glycosylation sites in the CDRs (Table 4A and B) and the affinity. The further detailed characterization included the specificity testing, the binding to and neutralization of native MCP-1, the affinity to human and cyno MCP-1, activity in the chemotaxis assay and the characterization of all converted IgG1.

The clones representing the optimized Fabs are represented by the sequences given in Table 4A-C, where clone MOR03471 parental Fab has VH1A x kappa3 frameworks and MOR03548 has on the VH3 x lambda 3 frameworks. The 17 selected Fabs with desirable physiochemical attributes (no N-glycosylation sites in the CDRs) and optimized properties of affinity and bioactivity, exhibit certain alternate unique CDR sequences and representative consensus sequences among the HC-CDR2 and LC CDR3 sequences within the frameworks used (VH3 and VH1A) as well as, more generally, a consensus among all HC-CDR1. These consensus sequences are shown in Tables 4C-4E and SEQ IN Nos: 2-26.

TABLE 4A

Heavy Chain CDR sequences of 17 selected binders

| Parental | MOR # | VH Type | HCDR1 | HCDR2 | HCDR3 |
|---|---|---|---|---|---|
| MOR03471 derivative (L-CDR3) | 3781 | VH1A | GGTFSSYGIS (SEQ ID NO: 6) | WMGGIIPIFGTANYAQKFQG (SEQ ID NO: 7) | YDGIYGELDF (SEQ ID NO: 9) |
| MOR03471 derivative (L-CDR3) | 3790 | VH1A | GGTFSSYGIS (SEQ ID NO: 6) | WMGGIIPIFGTANYAQKFQG (SEQ ID NO: 7) | YDGIYGELDF (SEQ ID NO: 9) |
| MOR03471 derivative (L-CDR3) | 3791 | VH1A | GGTFSSYGIS (SEQ ID NO: 6) | WMGGIIPIFGTANYAQKFQG (SEQ ID NO: 7) | YDGIYGELDF (SEQ ID NO: 9) |
| MOR03471 x clone (3822x3797) | 3849 | VH1A | GGTFSSYGIS (SEQ ID NO: 6) | WMGAINPLAGHTHYAQKFQG (SEQ ID NO: 8) | YDGIYGELDF (SEQ ID NO: 9) |
| MOR03471 x clone (3822x3819) | 3850 | VH1A | GGTFSSYGIS (SEQ ID NO: 6) | WMGAINPLAGHTHYAQKFQG (SEQ ID NO: 8) | YDGIYGELDF (SEQ ID NO: 9) |

TABLE 4A-continued

Heavy Chain CDR sequences of 17 selected binders

| Parental | MOR # | VH Type | HCDR1 | HCDR2 | HCDR3 |
|---|---|---|---|---|---|
| MOR03471 x clone (3822x3794) | 3878 | VH1A | GGTFSSYGIS (SEQ ID NO: 6) | WMGAINPLAGHTHYAQKFQG (SEQ ID NO: 8) | YDGIYGELDF (SEQ ID NO: 9) |
| MOR03471 x clone (3822x3788) | 3885 | VH1A | GGTFSSYGIS (SEQ ID NO: 6) | WMGAINPLAGHTHYAQKFQG (SEQ ID NO: 8) | YDGIYGELDF (SEQ ID NO: 9) |
| MOR03471 x clone (3822x3876) | 3899 | VH1A | GGTFSSYGIS (SEQ ID NO: 6) | WMGAINPLAGHTHYAQKFQG (SEQ ID NO: 8) | YDGIYGELDF (SEQ ID NO: 9) |
| MOR03548 derivative (L-CDR3) | 3744 | VH3 | GFTFRSYGMS (SEQ ID NO: 10) | WVSNIRSDGSYTYYADSVKG (SEQ ID NO: 11) | FEFTPWTYFDF (SEQ ID NO: 12) |
| MOR03548 derivative (L-CDR3) | 3747 | VH3 | GFTFRSYGMS (SEQ ID NO: 10) | WVSNIRSDGSYTYYADSVKG (SEQ ID NO: 11) | FEFTPWTYFDF (SEQ ID NO: 12) |
| MOR03548 derivative (H-CDR2) | 3753 | VH3 | GFTFRSYGMS (SEQ ID NO: 10) | WVSSIEHKWSGYTTSYAAS-VKG (SEQ ID NO: 23) | FEFTPWTYFDF (SEQ ID NO: 12) |
| MOR03548 derivative (H-CDR2) | 3754 | VH3 | GFTFRSYGMS (SEQ ID NO: 10) | WVSSIEHKWSGYATTYAAS-VKG (SEQ ID NO: 23) | FEFTPWTYFDF (SEQ ID NO: 12) |
| MOR03548 derivative (H-CDR2) | 3755 | VH3 | GFTFRSYGMS (SEQ ID NO: 10) | WVSSIEHKWSGYATGYAAS-VKG (SEQ ID NO: 23) | FEFTPWTYFDF (SEQ ID NO: 12) |
| MOR03548 derivative (H-CDR2) | 3757 | VH3 | GFTFRSYGMS (SEQ ID NO: 10) | WVSSIEHKWTNYATSYAAS-VKG (SEQ ID NO: 23) | FEFTPWTYFDF (SEQ ID NO: 12) |
| MOR03548 derivative (H-CDR2) | 3758 | VH3 | GFTFRSYGMS (SEQ ID NO: 10) | WVSSIEHKWTGYATSYAAS-VKG (SEQ ID NO: 23) | FEFTPWTYFDF (SEQ ID NO: 12) |
| MOR03548 derivative (H-CDR2) | 3832 | VH3 | GFTFRSYGMS (SEQ ID NO: 10) | WVSSIEHKWSNYAT-SYAAGVKG (SEQ ID NO: 23) | FEFTPWTYFDF (SEQ ID NO: 12) |
| MOR03548 derivative (H-CDR2) | 3836 | VH3 | GFTFRSYGMS (SEQ ID NO: 10) | WVSSIEHKWSGYATGYAAS-VKG (SEQ ID NO: 23) | FEFTPWTYFDF (SEQ ID NO: 12) |

TABLE 4B

Light Chain CDR sequences of 17 selected binders

| Parental | MOR # | VL Type | LCDR1 | LCDR2 | LCDR3 |
|---|---|---|---|---|---|
| MOR03471 derivative (L-CDR3) | 3781 | VL-κ3 | RASQSVSDAYLA (SEQ ID NO: 13) | LLIYDASSRAT (SEQ ID NO: 14) | HQYIELWSF (SEQ ID NO: 15) |
| MOR03471 derivative (L-CDR3) | 3790 | VL-κ3 | RASQSVSDAYLA (SEQ ID NO: 13) | LLIYDASSRAT (SEQ ID NO: 14) | HQYIQLHSF (SEQ ID NO: 15) |
| MOR03471 derivative (L-CDR3) | 3791 | VL-κ3 | RASQSVSDAYLA (SEQ ID NO: 13) | LLIYDASSRAT (SEQ ID NO: 14) | QQYIDISPM (SEQ ID NO: 24) |
| MOR03471 x clone (3822x3797) | 3849 | VL-κ3 | RASQSVSDAYLA (SEQ ID NO: 13) | LLIYDASSRAT (SEQ ID NO: 14) | QQYISHPQ (SEQ ID NO: 24) |
| MOR03471 x clone (3822x3819) | 3850 | VL-κ3 | RASQSVSDAYLA (SEQ ID NO: 13) | LLIYDASSRAT (SEQ ID NO: 14) | QQYITYPPF (SEQ ID NO: 24) |
| MOR03471 x clone (3822x3794) | 3878 | VL-κ3 | RASQSVSDAYLA (SEQ ID NO: 13) | LLIYDASSRAT (SEQ ID NO: 14) | QQYISFPA (SEQ ID NO: 24) |
| MOR03471 x clone (3822x3788) | 3885 | VL-κ3 | RASQSVSDAYLA (SEQ ID NO: 13) | LLIYDASSRAT (SEQ ID NO: 14) | QQYISQPV (SEQ ID NO: 24) |

TABLE 4B-continued

Light Chain CDR sequences of 17 selected binders

| Parental | MOR # | VL Type | LCDR1 | LCDR2 | LCDR3 |
|---|---|---|---|---|---|
| MOR03471 x clone (3822x3876) | 3899 | VL-κ3 | RASQSVSDAYLA (SEQ ID NO: 13) | LLIYDASSRAT (SEQ ID NO: 14) | HQYIFYPN (SEQ ID NO: 24) |
| MOR03548 derivative (L-CDR3) | 3744 | VL-λ3 | SGDNLGKKYVY (SEQ ID NO: 18) | LVIYDDDNRPS (SEQ ID NO: 19) | QTYDRFSSTA (SEQ ID NO: 20) |
| MOR03548 derivative (L-CDR3) | 3747 | VL-λ3 | SGDNLGKKYVY (SEQ ID NO: 18) | LVIYDDDNRPS (SEQ ID NO: 19) | QSYDRFSSTG (SEQ ID NO: 21) |
| MOR03548 derivative (H-CDR2) | 3753 | VL-λ3 | SGDNLGKKYVY (SEQ ID NO: 18) | LVIYDDDNRPS (SEQ ID NO: 19) | QSYTAQSSAS (SEQ ID NO: 25) |
| MOR03548 derivative (H-CDR2) | 3754 | VL-λ3 | SGDNLGKKYVY (SEQ ID NO: 18) | LVIYDDDNRPS (SEQ ID NO: 19) | QSYTAQSSAS (SEQ ID NO: 25) |
| MOR03548 derivative (H-CDR2) | 3755 | VL-λ3 | SGDNLGKKYVY (SEQ ID NO: 18) | LVIYDDDNRPS (SEQ ID NO: 19) | QSYTAQSSAS (SEQ ID NO: 25) |
| MOR03548 derivative (H-CDR2) | 3757 | VL-λ3 | SGDNLGKKYVY (SEQ ID NO: 18) | LVIYDDDNRPS (SEQ ID NO: 19) | QSYTAQSSAS (SEQ ID NO: 25) |
| MOR03548 derivative (H-CDR2) | 3758 | VL-λ3 | SGDNLGKKYVY (SEQ ID NO: 18) | LVIYDDDNRPS (SEQ ID NO: 19) | QSYTAQSSAS (SEQ ID NO: 25) |
| MOR03548 derivative (H-CDR2) | 3832 | VL-λ3 | SGDNLGKKYVY (SEQ ID NO: 18) | LVIYDDDNRPS (SEQ ID NO: 19) | QSYTAQSSAS (SEQ ID NO: 25) |
| MOR03548 derivative (H-CDR20) | 3836 | VL-λ3 | SGDNLGKKYVY (SEQ ID NO: 18) | LVIYDDDNRPS (SEQ ID NO: 19) | QSYTAQSSAS (SEQ ID NO: 25) |

TABLE 4C

Consensus Sequences for anti-MCP-1 V-regions

| SEQ ID NO: | wV-Region | FR1 | CDR1 | FR2 | CDR2 | FR3 | CDR3 | FR4 |
|---|---|---|---|---|---|---|---|---|
| 2 | VH1A | QVELVQSGAEVKKPGSSVKVSCKAS | GGTFSSYGIS | WVRQAPGQGLE | WMGXIXPXXGXXXYAQKFQG | RVTITADESTYDGIYGELDFGSTAYMELSSLRSEDTAVYYCAR | YDGIYGELDF | WGQGTLVTVSS |
| 3 | VH3 | QVQLVESGGGLVQPGGSLRLSCAAS | GFTFRSYGMS | WVRQAPGKGLE | WVSNIRSDGSRFTISRDNSKYTYYADSVKGNTLYLQMNSLFEFTPWTYFDRAEDTAVYYCAR | | FEFTPWTYFD | WGQGTLVTVSS |
| 4 | Kappa3 | DIVLTQSPATLSLSPGERATLSC | RASQSVSDAYLA | WYQQKPGQAPR | LLIYDASSRAGVPARFSGSGXQYIXXXXT SGTDFTLTISSLEPEDFAVYYC | | | FTFGQGTKVEIK |
| 5 | Lambda3 | DIELTQPPSVSVAPGQTARISC | SGDNLGKKYVY | WYQQKPGQAPV | LVIYDDDNRPGIPERFSGSNQXYXXXXSSXXFGGGTKLTVLS SGNTATLTISGTQAEDEADYYC | | | FGGGTKLTVL |

TABLE 4D

Anti-MCP-1 Unique CDRs

| V-region | CDR | SEQ ID NO: | Fab Designation | SEQUENCE |
|---|---|---|---|---|
| VH1A | CDR1 | 6 | All MOR03471 | GGTFSSYGIS |
| VH1A | CDR2 | 7 | 3781, 3790, CNTO 888 | WMGGIIPIFGTANYAQKFQG |
| VH1A | CDR2 | 8 | 3899 | WMGAINPLAGHTHYAQKFQG |
| VH1A | CDR3 | 9 | All MOR03471 | YDGIYGELDF |
| VH3 | CDR1 | 10 | All MOR03548 | GFTFRSYGMS |
| VH3 | CDR2 | 11 | 3744, 3747 | WVSNIRSDGSYTYYADSVKG |
| VH3 | CDR3 | 12 | All MOR03548 | FEFTPWTYFD F |
| Kappa3 | CDR1 | 13 | All MOR03471 | RASQSVSDAYLA |
| Kappa3 | CDR2 | 14 | All MOR03471 | LLIYDASSRA T |
| Kappa3 | CDR3 | 15 | 3781 | HQYIELWSF |
| Kappa3 | CDR3 | 16 | 3790, CNTO888 | HQYIQLHSF |
| Kappa3 | CDR3 | 17 | 3899 | HQYIFYPN |
| Lamda3 | CDR1 | 18 | All MOR03548 | SGDNLGKKYV Y |
| Lamda3 | CDR2 | 19 | All MOR03548 | LVIYDDDNRP S |
| Lamda3 | CDR3 | 20 | 3744 | QTYDRFSSTA |
| Lamda3 | CDR3 | 21 | 3747 | QSYDRFSSTG |

TABLE 4E

Anti-MCP-1 CDR Regions Consensus Sequences

| CDR | SEQ ID NO: | SEQUENCE | VARIANTS |
|---|---|---|---|
| VH1A-CDR2 | 22 | WMGXIXPXXG XXXYAQKFQG | X4 = A, G<br>X6 = I, N<br>X8 = I, L<br>X9 = A, F<br>X11 = H, T<br>X12 = A, T<br>X13 = H, N |
| VH3-CDR2 | 23 | WVSSIEHKWX XYXTXYAAXV KG | X10 = S, T<br>X11 = G, N<br>X13 = A, T<br>X15 = G, S, T<br>X19 = G, S |
| Lk-CDR3 | 24 | XQYIXXXX, where X8 may represent an amino acid pair | When length is 8 amino acids:<br>X1 = H, Q<br>X5 = F or S<br>X6 = Q, H, F, Y<br>X7 = P<br>X8 = A, N, Q, or V |
| | 29 | | When length is 9 amino acids:<br>X1 = H, Q<br>X5 = D, E, Q, or T<br>X6 = I, Y, or L<br>X7 = W, H, S, P<br>X8 = P or S<br>X9 = M or F, if X8 is P or is F if X8 is S |
| Lλ-CDR3 | 25 | QXYXXXSSXX | X2 = S, T<br>X4 = D, T<br>X5 = A, R<br>X6 = F, Q<br>X9 = A, T<br>X10 = A, G, S |
| HC-CDR1 | 26 | GXTFXSYGXS | X2 = F, G<br>X5 = S, R<br>X9 = I, M |

TABLE 5

Affinity summary of selected antibodies

| $K_D$ [nM] | MOR3757 | MOR3781 | MOR3790 | MOR3850 | MOR3878 | MOR3899 |
|---|---|---|---|---|---|---|
| Fab BioVeris rh MCP-1 n = 2 | 0.008/0.02 | 0.03 ± 0.01 | 0.12 ± 0.01 | 0.04 ± 0.01 | 0.32 ± 0.14 | 0.81 ± 0.18 |
| Fab BioVeris cyno MCP-1 n = 2 | 0.01/0.07 | 0.004/0.01 | 0.06 ± 0.02 | 0.04 | 0.32 ± 0.04 | 0.49 ± 0.04 |
| Fab KinexA bt-K69 h MCP-1 (CNTO) | 0.0067 | 0.0089 | 0.075 | 0.02 | ND | ND |
| IgG1 BioVeris rh MCP-1 n = 2 | ND | 0.02 | 0.07 ± 0.03 | 0.011 ± 0.005 n = 3 | 0.27 ± 0.06 n = 3 | 0.34 ± 0.05 |
| IgG1 BioVeris cyno MCP-1 n = 2 | ND | 0.016 ± 0.008 | 0.06 ± 0.01 | 0.021 ± 0.015 n = 3 | 0.23 ± 0.02 n = 3 | 0.36 ± 0.06 |

Binding to Native MCP-1 Measured by Biacore. Binding to native MCP-1 was tested in the Biacore Fab capture mode and all selected Fabs showed binding to native MCP-1. Especially as the detection limits for $K_D$ determination in Biacore were reached with the optimized Fabs, alternative methods for affinity determination and verification of specificity had to be used.

IgG Conversions. All optimized Fabs selected for detailed characterization were converted into IgG1 format, in addition 4 Fabs were sub-cloned into IgG4 format. The expression data and the activity in different assays of the tested human IgG4 were as good as of the respective IgG1.

Solution Equilibrium Titration Using BioVeris. As an alternative method for sensitive $K_D$ determinations, the solution equilibrium titration (SET) using BioVeris technology was performed. Monovalent dissociation constants were calculated by means of appropriate fit models for Fab and IgG. This method was suitable for affinity measurement and cross-reactivity studies. All selected 16 binders were analyzed by solution equilibrium titration (SET) using BioVeris (Table 5 and Table 6) and these affinity values were regarded as the final affinity values. Several binders including MOR03757, MOR03781, MOR03790, MOR03850, MOR03878 as Fab and IgG and MOR03899 as IgG fulfilled the affinity success criteria against human MCP-1 being <0.5 nM and cyno MCP-1 being <20 nM. Best affinities to human MCP-1 were 20 to 40 pM on the level of Fab and 10 to 20 pM on the level of IgG (Table 5). Best affinities to cynomolgus MCP-1 were 10 to 40 pM on the level of Fab and 20 pM on the level of IgG (Table 6).

Specificity Testing Using BioVeris. Beside the affinity also the specificity, especially the cross-reactivity to Eotaxin and MCP-2, was analyzed in solution equilibrium titration (SET) using BioVeris. No cross-reactivity to human MCP-2 was detectable for any of the selected 16 Fabs and 15 IgGs tested (one of the 16 selected IgGs was not available). As human MCP-1, human MCP-2 binds mainly to the CCR2 receptor, while human Eotaxin predominantly binds to the CCR3 receptor. No cross-reactivity to human Eotaxin was detectable for MOR03744, MOR03747, MOR03790 and MOR03781 Fab and IgG in BioVeris, while 12 selected binders including MOR03850 showed some cross-reactivity to Eotaxin in the Fab or IgG format (data not shown).

Specificity of Optimized Antibodies in Biacore Antibody Capture Mode (CNTO). Specificity evaluation was performed with selected IgGs. In Biacore 100 nM human MCP-1, human MCP-2, 3, 4 and human Eotaxin 1, 2 and 3 were added to captured optimized antibodies. MOR03790, MOR03791, MOR03747, MOR03850, MOR03744, MOR03849, MOR03878, MOR03885, MOR3899 and MOR03781 IgG showed no significant binding signal to the homologue chemokines and met the specificity success criteria (Table 6).

Fabs Binding to MCP-2 do not Inhibit $I^{125}$ MCP-2 Binding to Thp-1 Cells (CNTO). To analyze if the Fab binding activity to MCP-2 and Eotaxin detected in Biacore translated into neutralizing activity, radio ligand whole cell binding assays were developed at Centocor. $I^{125}$ MCP-2 showed nice binding to Thp-1 cells and the binding was inhibited by the addition of unlabeled MCP-2, but not by the addition of the MCP-1 specific reference antibody C775. The results provided an important functional assay for testing the binding/neutralization specificity. 1 ng/ml MCP-1 was used in receptor binding assay, while about 100 ng/ml MCP-2 were necessary in this assay, as MCP-2 labeling might have caused a loss in activity. MOR03754 showed no significant inhibition of 125I labeled MCP-2 binding to CCR2 receptor on Thp-1 cells ($IC_{50} \geq 2$ µM).

Matured Fabs Potently Inhibit $I^{125}$ MCP-1 Binding to THP-1 Cells (CNTO). Due to the low amount of 1 ng/ml MCP-1 needed, this assay was the most sensitive assay in this project with an assay $IC_{50}$ limit of about 100 pM for Fab and even 20 pM for IgG (Table 5). After optimization the Fabs had to inhibit human MCP-1 binding to its human receptor CCR2 on Thp-1 cells with $IC_{50}$ below reference Fab C775. Parental MOR03471 Fab showed an $IC_{50}$ of 180 nM and optimized MOR03471 Fab derivatives (MOR03781 with 180 pM, MOR03790 with 260 pM, MOR03850 with 160 pM, MOR03878 with 110 pM and MOR03899 with 130 pM) showed an overall improvement in activity during optimization up to a factor of 1000×. Although this assay was the most sensitive bioassay available in this project, even in this assay the optimized binders seemed to have reached the assay limits.

Matured IgGs Potently Inhibit $I^{125}$ MCP-1 Binding to THP-1 Cells (CNTO). Blocking of Fc receptor binding sites by addition of unrelated human IgG1 was important for radioligand binding and calcium mobilization assays. All tested IgG1 retained the activity in the radio-ligand binding assay. The $IC_{50}$ value of optimized MOR03781 was 20 pM, 30 pM for MOR03790, 50 pM for MOR03850, 30 pM for MOR03878 and 50 pM for MOR03899. Inhibition of MCP-1 induced CCR2 Receptor Internalization FACS Assay Development. The receptor internalization assays were performed using cells expressing CCR-2 that showed higher CCR2 expression than THP-1 cells, leading to a better signal to noise ratio. First the synthetic human MCP-1 was titrated in the assay to determine the $EC_{50}$ value. The $EC_{50}$ value for MCP-1 was found to be of 116 ng/ml. Therefore, 100 ng/ml (~11 nM) MCP-1 was chosen for further FACS assays. In addition the optimal incubation time to obtain complete internalization was evaluated at 37° C. Most of the internalization occurred within the first 30 min. Therefore, a 1 h incubation time was used in all subsequent assays. The assay was successfully developed to allow an $IC_{50}$ determination. Activity and ranking of between 0.001 to 200 µg/ml Fab or IgG used to inhibit MCP-1 induced receptor internalization was measured. The selected optimized binders showed good inhibition of MCP-1 induced receptor internalization (data not shown). Two different batches of Fabs were tested in parallel with demonstrated reproducibility.

For the internalization assay using Fabs, an $IC_{50}$ of 5 nM was detected for MOR03790, 4 nM for MOR03850, 7 nM for MOR03781, 5.3 nM for MOR03878 and 3.3 nM for MOR03899 (Table 6). MOR03781 IgG1 also showed 7 nM, indicating that the activity was retained after IgG conversion.

Inhibition of Calcium Mobilization (CNTO). MCP-1 induces calcium mobilization in THP-1 cells which can be detected with the help of a fluorophore. The optimized antibodies showed potent inhibition of calcium mobilization the 4 final candidates MOR03781, MOR03790, MOR03850 and MOR03878 Fab showed $IC_{50}$ values from 18 to 28 nM. The respective IgGs again retained the activity and showed even slightly better $IC_{50}$ values from about 6 to 10 nM due to their ability to neutralize 2 MCP-1 molecules per IgG. Again the assay limits seemed to be reached at about 10 nM.

Inhibition of Native MCP-1 Induced Calcium Mobilization. Native MCP-1 was purified from PANC1 supernatant and used for the induction of calcium release. Optimized Fabs showed inhibition of native MCP-1 induced calcium mobilization with higher activity as compared to the reference antibody C775. Again the assay limit seemed to be reached at about 10 to 20 nM native MCP-1.

Inhibition of Chemotaxis. Due to potential unspecific effects the parental Fabs could not be tested in chemotaxis assay, but after maturation all tested optimized Fabs specifically inhibited chemotaxis, which might be due to the increased activity. All optimized IgGs tested were active in chemotaxis assay. As the assay was semi-quantitative, no proper $IC_{50}$ values could be determined.

Binding Competition with Reference Antibody C775. All MOR03548 derived pre-selected Fabs completely inhibited binding of C775 to MCP1 in a competition solid phase format. All 7 MOR03471 derived pre-selected Fabs showed partial (~60%) competition in this assay.

Summary Data

The N-terminus sequence of mAb 3790 certain variances from the human germline sequences, due to the amino acid changes introduced during cloning. In addition, amino acid codons, (i.e. the DNA sequence) were biased maximum expression in prokaryotic bacterial cells. MAb DNA was re-synthesized to correct the imperfect N-terminus alignment to germline sequence and to change the codon bias to those favored in highly expressed human proteins. The sequence modified 3790 mAb is designated as CNTO 888 comprising heavy and light chain variable region sequences of SEQ ID NO: 27 and 28, respectively, and below (with CDRs underlined), where the N-terminal residues of the heavy chain are QVQ (Gln-Val-Gln) and or the light chain are EIV (Glu-Ile-Val).

TABLE 6

Profiles of the Abs That Met The Success Criteria

| Success Criteria | Reference Fab IgG | MOR3790k Fab IgG | MOR3850k Fab IgG | MOR3781k Fab IgG | MOR3878k Fab IgG | MOR3899k Fab IgG |
|---|---|---|---|---|---|---|
| #1, 6 MCP-1 Kd < 0.5 nM IGEN | 65, — | 0.12, 0.07 | 0.04, 0.01 | 0.03, 0.02 | 0.32 0.27 | (0.81) 0.34 |
| #2 MCP-1 specificity BIAcore (IgG) | None, None | (MCP-2/Eo), None | (MCP-2/Eo), None | (MCP-2/Eo), None | (MCP-2/Eo), None | (MCP-2/Eo), None |
| #3 $^{125}$I MCP-1 inhibition IC50 < C775 | 35.6, 25.6 | 0.26, 0.03 | 0.16, 0.05 | 0.18, 0.02 | 0.11, 0.03 | 0.13, 0.05 |
| #4 Inhibition of chemmotaxis | yes, yes | yes, ND | yes, ND | yes, ND | yes, ND | yes, ND |
| #5 Inhibition of Ca2+ Mobilization IC50 < C775 | 71.5, 62.3 | 25.02, 4.26 | 28.42, 9.47 | 21.8, 10.9 | 20.24, 6.7 | 17.54, 5.85 |
| #7 Cyno MCP-1 Kd < 10 nM | ND, ND | 0.06, 0.06 | 0.04, 0.01 | 0.01, 0.02 | 0.32, 0.23 | 0.49, 0.36 |
| #8 Inhibition of Native MCP-1 Induced Ca2+ | yes, ND | yes, ND | yes, ND | yes, ND | yes, ND | yes, ND |
| extended measurement-1 C775 competition | yes, yes | partial, ND | partial, ND | partial, ND | partial, ND | partial, ND |
| extended measurement-2 Inhibition of CCR2 internalization | 65, ND | 5, ND | 4, ND | 7, 7 | 5.3, ND | 3.3, ND |

Example 4

Selection of Therapeutic Candidates

Selection and Generation of the Final Therapeutic Candidate CNTO888.

Two of the mAbs, 3781 and 3790, which differ only in their light chain CDR3 sequences (Table 4B and D, SEQ ID Nos: 15 and 16) demonstrated almost identical biological activity in the assays. In silico immunogenicity analysis was performed to identify potential HLA class II binding peptides and to determine if the candidates differed significantly in the terms of HLA binding epitopes. The analysis predicted mAb 3790 to present a lower potential for immunogenicity than mAb 3781. Based on this and on the other biochemical and biological analysis shown in Table 6, 3790 comprising the heavy chain VH1A framework regions (SEQ ID NO: 2) and heavy chain CDR regions, SEQ ID NO. 6,7, and 9; and light chain kappa3 framework (SEQ ID NO: 4) and the CDR regions, SEQ ID NO: 13, 14, and 16, was selected as the final therapeutic mAb.

CNTO888 Heavychain variable sequence (SEQ ID NO: 27)
QVQLVQSGAEVKKPGSSVKVSCKASGGTFS

SYGISWVRQAPGQGLEWMGGIIPIFGTAN

YAQKFQGRVTITADESTSTAYMELSSLRSE

DTAVYYCARYDGIYGELDFWGQGTLVTVSS

CNTO888 Light chain variable (SEQ ID NO: 28)
EIVLTQSPATLSLSPGERATLSCRASQSVSDAYLAW

YQQKPGQAPRLLIYDASSRATGVPARFSGSGSGTDF

YYCHQYIQLHSFTFGQGTKVEIK

Biochemical and biophysical characterization of CNTO888. CNTO 888 is a fully human IgG1 kappa antibody. There are no predicted N-linked glycosylation sites in the sequence. The biochemical and biophysical properties of CNTO 888 (transiently expressed in HEK293 cells and purified by protein A affinity chromatography) were characterized in SDS-PAGE, size exclusion chromatography (SEC), mass spectrum (MS) and BIAcore, for binding affinity (Kd) and specificity. In SDS-PAGE, the native CNTO 888 migrates as a single band at approximately 150 kDa. The reduced/alkalyated IgG migrates as two bands at approximately 60 kDa and 33 kDa. Size exclusion chromatography of CNTO 888 demonstrated that the IgG elutes as a single peak at the same elution volume as that measured for the Remicade IgG control (data not shown). Finally, the MS analysis showed CNTO888 has a mass of 147,000 Da (data not shown). BIAcore analysis demonstrated that CNTO 888 binding affinity (Kd) to human and cyno CCL-2 was 30 and 10 pM, respectively. CNTO0888 did not show detectable binding in BIAcore to CCL-2 related chemokines, i.e. MCP-2, 3, 4 and eotaxin 1, 2 and 3.

In vitro characterization of CNTO888. The biological activities of CNTO 888 were evaluated in a variety cell based assays. CNTO 888 expressed transiently evaluated in all of the success criteria assays had activities of which were indistinguishable from the parent mAb 3790 (Table 5).

Example 5

Cloning and Expression of an Anti-MCP-1 Antibody

Aliquots of *E. coli* with the CNTO 888 plasmids, p2844 and p2882, contain the antibody heavy and light chains, respectively. The plasmid p2844 contains the optimized heavy chain coding sequence of CNTO0888 coding regions under the anti-CD4 heavy chain promoter and the plasmid p2882 contains the optimized light chain of CNTO0888 coding regions under the anti-CD4 light chain promoter. Both constructs include the gpt selection gene to confer chemical resistance to MHX (Mycophenolic acid, Hypoxanthine and Xanthine). Each plasmid was purified, characterized, quantified, and sequenced.

Cells from an exponential culture of the C463A host cell line, an Sp2/0 derivative adapted to growth in the chemically defined media (CD-Hybridoma), were co-electroporated with linearized p2844 and p2882. After 48 hours, the cells were exposed to 1×MHX (0.5 mg/L Mycophenolic acid, 2.5 mg/L Hypoxanthine and 50 mg/L Xanthine). Three days after selection, the cell viability had decreased to less than 13%, at which time ~90,000 viable cells were plated in methylcellulose. The cells were incubated undisturbed for eight to thirteen days, then screened and picked into 24-well plates using the Halo procedure. Cultures were expanded and 24-well overgrowth titers were obtained.

The highest parental cell line (1C4) had a 24-well overgrowth titer of 70 mg/L and a titer of 108.5 mg/L in shake flasks (in CD-Hybridoma media). This parental cell line, C1262A, was chosen for further evaluation in shake flasks. C1262A was submitted to the Cell Banking Group for generation of a Development Cell Bank (DCB). Cells from the DCB, designated C1262A:DCB; 02SEP04, tested negative for mycoplasma and sterility. Production of CNTO 888 to support further research studies from the C1262A cells in shake flasks (with addition of soy peptone) reached a titer of 230 mg/L and yielded 366 mg of purified CNTO 888 from 2 L culture. In parallel, an additional 9-L culture of C1262A cells produced ~2 g of crude CNTO 888 material for early purification and formulation development.

The parental cell line, C1262A, was subcloned using the Halo procedure and yielded five high-producing subclone cell lines. The best subclone cell line (4D5) had a 24-well overgrowth titer of 150.5 mg/L and a titer of 167 mg/L in shake flasks (in CD-Hybridoma). This subclone cell line was coded C1262B.

Example 6

Treatment of Human Pancreatic Tumors with CNTO0888

This study investigates whether blockade of tumor MCP-1 (produced by human tumor derived cells) suppress tumor growth in a murine xenografts. In order to gauge the tumor, as well as the host MCP-1 homolog, JE, role in the growth and progression of malignant disease, both anti-human MCP-1 and anti-mouse JE antibodies were tested for the ability to suppress the growth of human pancreatic tumors in vivo.

Mice bearing BxPC-3 pancreatic tumors were treated with the human anti-human MCP-1 antibody designated CNTO0888 which comprises the variable region sequences (SEQ ID Nos: 27 and 28) fused to human IgG1 constant regions. In order to compare the in vivo activity of CNTO0888 with the previously tested murine antibody in which it was found most effective inhibit the host effects, both the CNTO0888 and murine anti-human MCP-1 (C775) were administered in combination with anti-muJE (C1142). Based on the final tumor weight measurement, both the human (CNTO0888) and murine (C775) anti-human MCP-1 Mabs significantly inhibited tumor growth.

Materials and Methods

BxPC-3 are human pancreatic cancer derived cells. Matrigel™ prepared from the Engelbreth-Holm-Swarm (EHS) tumor was obtained from Becton Dickinson (0.2 EU/mg, Bedford, Mass.).

C775 is a mouse anti-human MCP-1 Mab and C1142 is a rat/murine chimeric anti-mouse JE antibody, with rat variable and mouse constant region both described in applicants co-pending patent application U.S. Ser. No. 11/170,453 and related filings. Control antibody cVaM is a rat/murine chimeric IgG$_{2a}$k consisting of a rat variable and mouse constant region which serves as an isotype control for C1142 and C775. Clinical grade human IgG was obtained from Beckett Apothecary and Home Health Care, Inc, Sharon Hill, Pa. and serves as a control for CNTO888.

Female SCID mice (6-8 weeks of age) obtained from Charles River (Raleigh, N.C.) were used in the study. Mice were group-housed in filter topped plastic cages and supplied with autoclaved food and water.

BxPC-3 cells were cultured in RPMI 1640 medium containing 10% FBS (complete medium). Cells were split 1:3 forty-eight hours before the start of the study. On the day of the study, cells were trypsinized to generate a single cell suspension and the cell suspension was washed with 10 volumes of the complete medium to neutralize the trypsin. Cells were spun down and resuspended in serum-free RPMI. Matrigel™ was thawed at 4° C. overnight. Matrigel™-tumor cell suspension was prepared by mixing equal volumes of Matrigel™ solution and BxPC-3 cells. The final concentration of the cancer cell suspension was 5×10$^6$ cells/mL in 5 mg/ml Matrigel™.

On day 0, 80 female SCID mice were implanted s.c. with 0.2 ml of BxPC-3 cell suspension. The 0.2 ml cell suspension contained 1×10$^6$ BxPC-3 cells and 1.0 mg of Matrigel™. Cold syringes were used to avoid polymerization of the Matrigel™.

TABLE 7

Anti-tumor study design.

| Group Number | Animals per Group | Treatment (i.p.) |
|---|---|---|
| 1 | 10 | PBS |
| 2 | 10 | cVaM + huIgG (20 mg/kg each antibody) |
| 3 | 10 | C775 + C1142 (20 mg/kg each antibody) |
| 4 | 10 | CNTO888 + C1142 (2 mg/kg each antibody) |
| 5 | 10 | CNTO888 + C1142 (20 mg/kg each antibody) |

All animals were weighed at the start of the study and once a week during the course of the study. Once tumor growth was observed (3.0 mm$^3$), tumors were measured with calipers in two dimensions (length and width) in millimeters (mm). Mice were monitored for tumor growth and the tumor volume (mm$^3$) was calculated based on the formula [length×width×width]/2.

On day 14 post implantation of the tumor cells, mice with a mean tumor volume of about 50 mm$^3$ were randomized into five groups (n=10/group). Treatment (Table 7) began on day 14, and treatments were administered twice a week for the remainder of the study (52 days after treatment start on day 14). Tumors were measured once a week for the remainder of the study. At the end of the study, mice were euthanized by $CO_2$ asphyxiation. Tumors were dissected, weighed on a digital balance, and fixed. Tumors were photographed using a digital camera. On Day 50, one mouse in Group 3 had tumor exceeding the limit acceptable under the study guidelines and was sacrificed. The volume and weight of this animal are included in the final analysis.

For tumor weights, the data were analyzed via standard linear model and analysis of variance (ANOVA). P-values less than 0.05 for all tests and comparisons were deemed significant unless otherwise indicated. The logarithmic scale was used since underlying assumptions of equal variance and normal distribution shape were better satisfied. The half-dozen zero values, for mice that were free of tumor, were replaced with a small spline-interpolated value (0.007240538) that facilitated statistical analysis in the logarithmic scale without corruption of the data structure.

For the tumor volume, a repeated measures model was fit to the data assuming a first-order autocorrelation covariance structure. Natural splines were used to flexibly model the curvature of trends in the time profiles. Pairwise comparisons amongst the groups were made at each of the timepoints. Calculations were performed by the R software environment.

Results

Both the PBS and cVam/huIgG negative control groups showed similar tumor growth, reaching ~350 mm$^3$ after 51 days. This indicates that antibody treatment with irrelevant antibodies does not inhibit tumor growth. Tumor growth in the three test groups (C775/C1142 and CNTO0888/C1142) was slower than in the negative control groups, indicating that the anti-CCL2/anti-JE treatments had an impact on tumor growth. The C775/C1142 and CNTO0888/C1142 (2 mg/kg) groups showed significant tumor inhibition compared to the PBS control group, as measured by tumor volume from Day 18 to the end of the study. The CNTO0888/C1142 (20 mg/kg) group showed significant inhibition from Day 18 to Day 39, as compared to the PBS control group.

Tumor weights were obtained at the end of the study on Day 51 (Table 8). There were tumor-free mice in PBS Group 1 (1 mouse), C775/C1142 Group 3 (3 mice), and CNTO0888/C1142 Group 4 (2 mice). When tumor weights were compared, the CNTO0888 test groups each showed a significant reduction in tumor weights compared to the PBS control group (Table 8). The percent inhibition in the CNTO0888/C1142 group dosed at 2 mg/kg was 80% (P=0.006), while for the CNTO0888/C1142 group dosed at 20 mg/kg the inhibition was 68% (P=0.046). The C775/C1142 group also showed a significant inhibition of tumor growth (P=0.004). The differences seen in statistical interpretation of the tumor volume vs tumor weight results is most likely due to imprecision in measuring tumor volume with calipers, as compared to the precision of weighing tumors excised from the animal.

TABLE 8

Final Tumor Weights

| Animal # | PBS | cVaM + Hu IgG | C775 + C1142 | CNTO888 + C1142* | CNTO888 + C1142 |
|---|---|---|---|---|---|
| 1 | 0 | 0.142 | 0 | 0.089 | 0.116 |
| 2 | 0.34 | 0.349 | 0.075 | 0 | 0.13 |
| 3 | 0.368 | 0.302 | 0 | 0.04 | 0.028 |
| 4 | 0.239 | 0.667 | 0.032 | 0.123 | 0.13 |
| 5 | 0.386 | 0.268 | 0.273 | 0.198 | 0.453 |
| 6 | 0.222 | 0.178 | 0.018 | 0.065 | 0.059 |
| 7 | 0.926 | 0.531 | 0.044 | 0.196 | 0.058 |
| 8 | 0.484 | 0.485 | 0.307 | 0.128 | 0.029 |
| 9 | 0.564 | 0.302 | 0 | 0 | 0.024 |
| 10 | 0.459 | 0.28 | 1.328 | 0.031 | 0.356 |
| Mean Tumor Weight (g) | 0.399 | 0.350 | 0.208 | 0.087 | 0.138 |
| SD | 0.244 | 0.163 | 0.410 | 0.073 | 0.148 |

Collectively, these results indicate that in the established BxPC-3 model, blockade of MCP-1 and mouse JE significantly inhibits tumor growth, and that CNTO0888 has anti-tumor activity.

It will be clear that the invention can be practiced otherwise than as particularly described in the foregoing description and examples.

Numerous modifications and variations of the present invention are possible in light of the above teachings and, therefore, are within the scope of the appended claims.

REFERENCES

Abraham R., Buxbaum, S. Link, J., Smith, R., Venti, C., Darsley, M. (1996). Determination of Binding Constants of Diabodies directed against Prostate-specific Antigen using Electrochemiluminescence-based Immunoassays. J. Mol. Recognit., 9(5-6):456-61.

Ausubel, F. M., Brent, R., Kingston, R. E., Moore, D. D., Seidman, J. G., Smith, J. A., Struhl, K., (1998) Current Protocols in Molecular Biology, Wiley, New York, USA Belperio J A, Keane M P, Burdick M D, Lynch J P 3rd, Xue Y Y, Berlin A, Ross D J, Kunkel S L, Charo I F, Stricter R M. (2001). Critical role for the chemokine MCP-1/CCR2 in the pathogenesis of bronchiolitis obliterans syndrome. J Clin Invest. 108(4):547-56.

Boder, E. T., Midelfort, K. S., Wittrup, K. D. (2000). Directed evolution of antibody fragments with monovalent femtomolar antigen-binding affinity. PNAS 97, 20, 10701-10705

Carnevale K A, Cathcart M K. (2003). Protein kinase C beta is required for human monocyte chemotaxis to MCP-1. J Biol. Chem. 278(28):25317-22.

Chen Y, Hallenbeck J M, Ruetzler C, Bol D, Thomas K, Berman N E, Vogel S N. (2003). Overexpression of monocyte chemoattractant protein 1 in the brain exacerbates ischemic brain injury and is associated with recruitment of inflammatory cells. J Cereb Blood Flow Metab. 23(6):748-55.

Chen, B. P., Hai, T. Expression vectors for affinity purification and radiolabeling of proteins using *Escherichia coli* as host. Gene 139, 73-75, 1994

Chen, Y., Wiesmann, C., Fuh, G., Li, B., Christinger, H. W., McKay, P., de Vos, A. M., Lowman, H. B. (1999). Selection and analysis of an optimized anti-VEGF antibody: crystal structure of an affinity-matured Fab in complex with antigen. J. Mol. Biol. 293, 865-881

Conti P, DiGioacchino M. (2001). MCP-1 and RANTES are mediators of acute and chronic inflammation. Allergy Asthma Proc. 22(3):133-7.

Dawson J, Miltz W, Mir A K, Wiessner C. (2003). Targeting monocyte chemoattractant protein-1 signalling in disease. Expert Opin Ther Targets. 7(1):35-48.

Ernst C A, Zhang Y J, Hancock P R, Rutledge B J, Corless C L, Rollins B J. (1994). Biochemical and biologic characterization of murine monocyte chemoattractant protein-1. Identification of two functional domains. J Immunol. 152 (7):3541-9.

Friguet B., Chaffotte A. F., Djavadi-Ohaniance L., & Goldberg M. E. (1985). Measurements of the true affinity constant in solution of antigen-antibody complexes by enzyme-linked immunosorbent assay. J. Immunol. Meth. 77, 305-319.

Frisch, C., Brocks, B., Ostendorp, R., Hoess, A., von Ruden, T., and Kretzschmar, T. (2003). From EST to IHC: human antibody pipeline for target research. J Immunol Methods 275, 203-212.

Gosling J, Slaymaker S, Gu L, Tseng S, Zlot C H, Young S G, Rollins B J, Charo I F. (1999). MCP-1 deficiency reduces susceptibility to atherosclerosis in mice that overexpress human apolipoprotein B. J Clin Invest. 103(6):773-8.

Haenel C, Satzger M, Della Ducata D, Ostendorp R and Brocks B (2005) Chraterization of High Affinity Antibodies by Electrochemiluminescence-Based Equilibrium Titration (accepted for publication in Analytical Biochemistry)

Hemmerich S, Paavola C, Bloom A, Bhakta S, Freedman R, Grunberger D, Krstenansky J, Lee S, McCarley D, Mulkins M, Wong B, Pease J, Mizoue L, Mirzadegan T, Polsky I, Thompson K, Handel T M, Jamagin K. (1999). Identification of residues in the monocyte chemotactic protein-1 that contact the MCP-1 receptor, CCR2. Biochemistry 38(40): 13013-25.

Hughes P M, Allegrini P R, Rudin M, Perry V H, Mir A K, Wiessner C. (2002). Monocyte chemoattractant protein-1 deficiency is protective in a murine stroke model. J Cereb Blood Flow Metab. 22(3):308-17.

Jamagin K, Grunberger D, Mulkins M, Wong B, Hemmerich S, Paavola C, Bloom A, Bhakta S, Diehl F, Freedman R, McCarley D, Polsky I, Ping-Tsou A, Kosaka A, Handel T M. (1999). Identification of surface residues of the monocyte chemotactic protein 1 that affect signaling through the receptor CCR2. Biochemistry. 38(49):16167-77.

Jimenez-Sainz M C, Fast B, Mayor F Jr, Aragay A M. (2003). Signaling pathways for monocyte chemoattractant protein 1-mediated extracellular signal-regulated kinase activation. Mol. Pharmacol. 64(3):773-82.

Knappik, A., Ge, L., Honegger, A., Pack, P., Fischer, M., Wellnhofer, G., Hoess, A., Wolle, J., Plückthun, A., and Vimekas, B. (2000). Fully synthetic human combinatorial antibody libraries (HuCAL) based on modular consensus frameworks and CDRs randomized with trinucleotides. J Mol Biol 296, 57-86.

Krebs, B., Rauchenberger, R., Reiffert, S., Rothe, C., Tesar, M., Thomassen, E., Cao, M., Dreier, T., Fischer, D., Hoss, A., Inge, L., Knappik, A., Marget, M., Pack, P., Meng, X. Q., Schier, R., Sohlemann, P., Winter, J., Wolle, J., and Kretzschmar, T. (2001). High-throughput generation and engineering of recombinant human antibodies. J Immunol Methods 254, 67-84.

Kretzschmar, T. and von Rüden, T. (2002). Antibody discovery: phage display. Curr Opin Biotechnol 13:598-602.

Leonard E J, Yoshimura T. (1990). Human monocyte chemoattractant protein-1. Immunol Today., 11: 97-101.

Löhning, C. (2001). Novel methods for displaying (poly) peptides/proteins on bacteriophage particles via disulfide bonds. WO 01/05950.

Losy J, Zaremba J. (2001). Monocyte chemoattractant protein-1 is increased in the cerebrospinal fluid of patients with ischemic stroke. Stroke. 32(11):2695-6.

Low, N. M., Holliger, P., Winter, G. (1996). Mimicking somatic hypermutation: affinity maturation of antibodies displayed on bacteriophage using a bacterial mutator strain. J. Mol. Biol. 260, 359-368

Mahad D J, Ransohoff R M. (2003). The role of MCP-1 (CCL2) and CCR2 in multiple sclerosis and experimental autoimmune encephalomyelitis (EAE). Semin Immunol. 15(1):23-32.

McManus C, Berman J W, Brett F M, Staunton H, Farrell M, Brosnan C F. (1998). MCP-1, MCP-2 and MCP-3 expression in multiple sclerosis lesions: an immunohistochemical and in situ hybridization study. J Neuroimmunol. 86(1): 20-9.

Nagy Z A, Hubner B, Lohning C, Rauchenberger R, Reiffert S, Thomassen-Wolf E, Zahn S, Leyer S, Schier E M, Zahradnik A, Brunner C, Lobenwein K, Rattel B, Stanglmaier M, Hallek M, Wing M, Anderson S, Dunn M, Kretzschmar T, Tesar M. (2002). Fully human, HLA-DR-specific monoclonal antibodies efficiently induce programmed death of malignant lymphoid cells. Nat. Med. 8(8):801-7.

Nakamura M, Kyo S, Kanaya T, Yatabe N, Maida Y, Tanaka M, Ishida Y, Fujii C, Kondo T, Inoue M, Mukaida N. (2004). hTERT-promoter-based tumor-specific expression of MCP-1 effectively sensitizes cervical cancer cells to a low dose of cisplatin. Cancer Gene Ther. 11(1):1-7.

Neumark E, Sagi-Assif O, Shalmon B, Ben-Baruch A, Witz I P. (2003). Progression of mouse mammary tumors: MCP-1-TNFalpha cross-regulatory pathway and clonal expression of promalignancy and antimalignancy factors. Int J Cancer. 106(6):879-86.

Ni W, Kitamoto S, Ishibashi M, Usui M, Inoue S, Hiasa K, Zhao Q, Nishida K, Takeshita A, Egashira K. (2004). Monocyte chemoattractant protein-1 is an essential inflammatory mediator in angiotensin II-induced progression of established atherosclerosis in hypercholesterolemic mice. Arterioscler Thromb Vasc Biol. 24(3):534-9.

Nokihara H, Yanagawa H, Nishioka Y, Yano S, Mukaida N, Matsushima K, Sone S. (2000). Natural killer cell-dependent suppression of systemic spread of human lung adenocarcinoma cells by monocyte chemoattractant protein-1 gene transfection in severe combined immunodeficient mice. Cancer Res. 15; 60(24):7002-7.

Ohta M, Kitadai Y, Tanaka S, Yoshihara M, Yasui W, Mukaida N, Haruma K, Chayama K. (2003). Monocyte chemoattractant protein-1 expression correlates with macrophage infiltration and tumor vascularity in human gastric carcinomas. Int J Oncol. 22(4):773-8.

Pichler, J, Brecht, A., Giersch, T., Hock, B., Gauglitz. G (1997). Assessment of affinity constants by rapid solid phase detection of equilibrium binding in a flow system. J. Immunol. Meth. 201, 189-206.

Pricket, K S, Amberg D C, Hopp T P (1989). A calcium-dependent antibody for identification and purification of recombinant proteins. Biotechniques. 7(6):580-9

Rauchenberger, R., Borges, E., Thomassen-Wolf, E., Rom, E., Adar, R., Yaniv, Y., Malka, M., Chumakov, I., Kotzer, S., Resnitzky, D., Knappik, A., Reiffert, S., Prassler, J., Jury, K., Waldherr, D., Bauer, S., Kretzschmar, T., Yayon, A., and Rothe, C. (2003). Human combinatorial Fab Library yielding specific and functional antibodies against the human fibroblast growth factor receptor 3. J Biol Chem. 278(40): 38194-38205

Ren G, Dewald O, Frangogiannis N G. (2003). Inflammatory mechanisms in myocardial infarction. Curr Drug Targets Inflamm Allergy. 2(3):242-56.

Rose C E Jr, Sung S S, Fu S M. (2003). Significant involvement of CCL2 (MCP-1) in inflammatory disorders of the lung. Microcirculation. 10(3-4):273-88.

Salcedo R, Ponce M L, Young H A, Wasserman K, Ward J M, Kleinman H K, Oppenheim J J, Murphy W J. (2000). Human endothelial cells express CCR2 and respond to MCP-1: direct role of MCP-1 in angiogenesis and tumor progression. Blood. 96(1):34-40.

Sarau H M, Rush J A, Foley J J, Brawner M E, Schmidt D B, White J R, Barnette M S. (1997). Characterization of functional chemokine receptors (CCR1 and CCR2) on EoL-3 cells: a model system to examine the role of chemokines in cell function. J Pharmacol Exp Ther. 283(1):411-8.

Sartipy P, Loskutoff D J. (2003). Monocyte chemoattractant protein 1 in obesity and insulin resistance. Proc Natl Acad Sci USA. 100(12):7265-70.

Schier, R., Bye, J., Apell, G., Mc Call, A., Adams, G. P., Malmqvist, M., Weiner, L. M. Weiner, Marks, J. D. (1996a). Isolation of high-affinity monomeric human anti-c-erbB-2 single chain Fv using affinity-driven selection. J. Mol. Biol. 255, 28-43

Schier, R., McCall, A., Adams, G. P., Marshall, K. W., Merritt, H., Yim, M., Crawford, R. S., Weiner, L. M., Marks, C., Marks, J. D. (1996b). Isolation of picomolar affinity anti-c-erbB-2 single-chain Fv by molecular evolution of the complementarity determining regions in the center of the antibody binding site. J. Mol. Biol. 263, 551-567

Schmidt, T. G. M., Koepke, J., Frank, R. and Skerra, A. (1996). Molecular interaction between the Strep-tag affinity peptide and its cognate target streptavidin. J. Mol. Biol. 255, 753-766

Seli E, Selam B, Mor G, Kayisli U A, Pehlivan T, Arici A. (2001). Estradiol regulates monocyte chemotactic protein-1 in human coronary artery smooth muscle cells: a mechanism for its antiatherogenic effect. Menopause. 8(4):296-301.

Sung F L, Zhu T Y, Au-Yeung K K, Siow Y L, O K. (2002). Enhanced MCP-1 expression during ischemia/reperfusion injury is mediated by oxidative stress and NF-kappaB. Kidney Int. 62(4): 1160-70.

Szalai C, Kozma G T, Nagy A, Bojszko A, Krikovszky D, Szabo T, Falus A. (2001). Polymorphism in the gene regulatory region of MCP-1 is associated with asthma susceptibility and severity. J Allergy Clin Immunol. 108(3):375-81.

Takahashi K, Mizuarai S, Araki H, Mashiko S, Ishihara A, Kanatani A, Itadani H, Kotani H. (2003). Adiposity elevates plasma MCP-1 levels leading to the increased CD11b-positive monocytes in mice. J Biol Chem. 278(47): 46654-60.

Tonouchi H, Miki C, Ohmori Y, Kobayashi M, Mohri Y, Tanaka K, Konishi N, Kusunoki M. (2004). Serum monocyte chemoattractant protein-1 in patients with postoperative infectious complications from gastrointestinal surgery for cancer. World J Surg. 28(2):130-6.

Van Der Voom P, Tekstra J, Beelen R H, Tensen C P, Van Der Valk P, De Groot C J. (1999). Expression of MCP-1 by reactive astrocytes in demyelinating multiple sclerosis lesions. Am J Pathol. 154(1):45-51.

Voss, S. and Skerra, A. (1997). Mutagenesis of a flexible loop in streptavidin leads to higher affinity for the Strep-tag II peptide and improved performance in recombinant protein purification. Protein Eng. 10, 975-982

Yamada M, Kim S, Egashira K, Takeya M, Ikeda T, Mimura O, Iwao H. (2003). Molecular mechanism and role of endothelial monocyte chemoattractant protein-1 induction by vascular endothelial growth factor. Arterioscler Thromb Vasc Biol. 23(11):1996-2001.

Yang, W., Green, K., Pinz-Sweeney, S., Briones, A. T., Burton, D. R., Barbas III, C. F. (1995). CDR walking mutagenesis for the affinity maturation of a potent human anti-HIV-1 antibody into the picomolar range. J. Mol. Biol. 254, 392-403

Yoshimura T, Leonard E J. (1999). Identification of high affinity receptors for human monocyte chemoattractant protein-1 on human monocytes. J Immunol., 145(1):292-7.

Zhu B Q, Heeschen C, Sievers R E, Karliner J S, Parmley W W, Glantz S A, Cooke J P. (2003). Second hand smoke stimulates tumor angiogenesis and growth. Cancer Cell. 4(3): 191-6.

What is claimed is:

1. An isolated antibody that binds monocyte chemoattractant protein-1 (MCP-1), wherein the antibody comprises the heavy chain variable sequence of SEQ ID NO: 27 and the light chain variable sequence of SEQ ID NO: 28.

2. An isolated antibody that binds MCP-1, wherein the antibody comprises a heavy chain variable region and a light chain variable region, wherein said heavy chain variable region comprises the heavy chain complementarity determining region (CDR) amino acid sequences of SEQ ID NOS: 6, 7, and 9 and the light chain CDR amino acid sequences of SEQ ID NOS: 13, 14, and 16.

3. An MCP-1 antibody according to claim 1 or 2, wherein said antibody binds MCP-1 with an affinity of between $10^{-9}$ M and $10^{-12}$ M.

4. A pharmaceutical composition comprising an isolated mammalian MCP-1 antibody according to claim 1 comprising a pharmaceutically acceptable carrier or diluent.

5. An article of manufacture for, comprising packaging material and a container comprising the antibody according to claim 1 in solution or lyophilized form.

* * * * *